US005972634A

United States Patent [19]
Tanzi et al.

[11] Patent Number: 5,972,634
[45] Date of Patent: Oct. 26, 1999

[54] DIAGNOSTIC ASSAY FOR ALZHEIMER'S DISEASE: ASSESSMENT OF Aβ ABNORMALITIES

[75] Inventors: Rudolph E. Tanzi, Canton; Ashley I. Bush, Somerville; Robert D. Moir, Boston, all of Mass.

[73] Assignee: The General Hospital Corporation, Boston, Mass.

[21] Appl. No.: 08/817,423

[22] PCT Filed: Oct. 19, 1994

[86] PCT No.: PCT/US94/11895

§ 371 Date: Aug. 4, 1997

§ 102(e) Date: Aug. 4, 1997

[87] PCT Pub. No.: WO96/12544

PCT Pub. Date: May 2, 1996

[51] Int. Cl.$^6$ ................................................. G01N 33/53
[52] U.S. Cl. ........................... 435/7.94; 435/7.1; 435/7.9; 435/7.92; 435/7.95; 435/975; 436/525; 436/164; 436/172
[58] Field of Search ..................................... 435/7.1, 7.92, 435/7.94, 7.95, 975, 7.9; 436/525, 164, 172, 63

[56] References Cited

U.S. PATENT DOCUMENTS

| | | |
|---|---|---|
| 4,504,585 | 3/1985 | Reynolds . |
| 4,666,829 | 5/1987 | Glenner et al. . |
| 5,164,295 | 11/1992 | Kisilevsky et al. . |
| 5,231,000 | 7/1993 | Majocha et al. . |
| 5,242,932 | 9/1993 | Gandy et al. . |
| 5,262,332 | 11/1993 | Selkoe . |
| 5,276,059 | 1/1994 | Caughey et al. . |
| 5,434,050 | 7/1995 | Maggio et al. . |

FOREIGN PATENT DOCUMENTS

WO 94/17197  8/1994  WIPO .

OTHER PUBLICATIONS

Assaf, S.Y. and Chung, S.H., "Release of endogenous $Zn^{2+}$ from brain tissue during activity," *Nature* 308:734–736 (1984).

Backstrom, J.R. et al., "Characterization of Neutral Proteinases from Alzheimer–Affected and Control Brain Specimens: Identification of Calcium–Dependent Metalloproteinases from the Hippocampus," *J. Neurochem.* 58(3):983–992 (1992).

Baker, R.J. et al., "Platelet Metal Levels in Normal Subjects Determined by Atomic Absorption Spectrophotometry," *Thrombos. Haemostas.* (Stuttg.)39:360–365 (1978).

Björkstén, B. et al., "Zinc and Immune Function in Down's Syndrome," *Acta Paediatr. Scand.* 69:183–187 (1980).

Bush, A.I. et al., "The Amyloid Precursor Protein of Alzheimer's Disease Is Released by Human Platelets," *J. Biol. Chem.* 265(26):15977–15983 (1990).

Bush, A.I. et al., "An Abnormality of Plasma Amyloid Protein Precursor in Alzheimer's Disease," *Ann. Neurol.* 32(1):57–65 (1992).

Bush, A.I. et al., "A Novel Zinc(II) Binding Site Modulates the Function of the βA4 Amyloid Protein Precursor of Alzheimer's Disease," *J. Biol. Chem.* 268(22):16109–16112 (Aug. 1993).

Bush, A.I. et al., "Modulation of Aβ Adhesiveness and Secretase Site Cleavage by Zinc," *J. Biol. Chem.* 269(16):12152–12158 (1994).

Candy, J.M. et al., "Aluminosilicates and Senile Plaque Formation in Alzheimer's Disease," *Lancet*:354–357 (Feb. 15, 1986).

Candy, J.M. et al., "Amorphous aluminosilicates promote nucleation of amyloid β protein and tachykinins," *Biochem. Soc. Trans.* 21:53S (1992).

Constantinidis, J., "Maladie d'Alzheimer et al théorie du zinc," *L'Encéphale XVI*:231–239 (1990), Abstract only.

Corrigan, F.M. et al., "Hippocampal tin, aluminum and zinc in Alzheimer's disease," *BioMetals* 6(3):149–154 (Jul. 1993).

Crapper McLachlan et al., "Intramuscular desferrioxamine in patients with Alzheimer's disease," *Lancet* 337:1304–1308 (1991).

Davies, I.J.T., et al., "Measurements of plasma zinc," *J. Clin. Path.* 21:359–365 (1968).

Duncan, M.W. et al., "Zinc, a Neurotoxin to Cultured Neurons, Contaminates Cycad Flour Prepared Traditional Guamanian Methods," *J. Neuroscience* 12(4):1523–1537 (1992).

Esch, F.S. et al., "Cleavage of Amyloid β Peptide During Constitutive Processing of Its Precursor," *Science* 248:1122–1124 (1990).

Fitzgerald, D.J. et al., "Zinc and Alzheimer's Disease," *Science* 268:1920–1923 (1995).

Folstein, M.F. et al., "'Mini–Mental State' A Practical Method for Grading the Cognitive State of Patients for the Clinician," *J. Psychiat. Res.* 12:189–198 (1975).

Franceschi, C. et al., "Oral zinc supplementation in Down's syndrome: restoration of thymic endocrine activity and of some immune defects," *J. Ment. Def. Res.* 32:169–181 (1988).

Frederickson, C.J. et al., "Cytoarchitectronic Distribution of Zinc in the Hippocampus of Man and the Rat," *Brain Res.* 273:335–339 (1983).

(List continued on next page.)

*Primary Examiner*—Patricia A. Duffy
*Attorney, Agent, or Firm*—Sterne, Kessler, Goldstein & Fox P.L.L.C.

[57] ABSTRACT

The disclosed invention relates to assays for detecting and quantifying Aβ peptide, using solid supports that are coated with heavy metal cations, such as zinc (II) or copper (II) form of a nitriloacetic acid. Further, diagnostic kits are described which are used to carry out the assays of the present invention. An improvement in an assay for detection of Aβ peptide is suggested which comprises forming a heavy metal cation/solid support complex. The preferred heavy metal cations for this improvement are zinc (II) or copper (II) form of a nitriloacetic acid. Finally, methods and kits for bulk purification of Aβ peptides from biological fluids are taught.

30 Claims, 26 Drawing Sheets

OTHER PUBLICATIONS

Frederickson, C.J. et al., "Zinc–containing 7S–NGF Complex. Evidence From Zinc Histochemistry fo Localization in Salivary Secretory Granules," *J. Hist. Cytochem.* 35(5):579–583 (1987).

Frederickson, C.J., "Neurobiology of Zinc and Zinc–Containing Neurons," *Intl. Rev. Neurobiol.* 31:145–238 (1989).

Fredericq, E., "The Association of Insulin Molecular Units in Aqueous Solutions," *Arch. Biochem. Biophys.* 65:218–228 (1956).

Galasko, D. et al., "Monitoring Progression in Alzheimer's Disease," *JAGS* 39:932–941 (1991).

Garruto, R.M. et al., "Imaging of calcium and aluminum in neurofibrillary tangle–bearing neurons in parkinsonism–dementia of Guam," *Proc. Natl. Acad. Sci. USA* 81:1875–1879 (1984).

Glenner, G.G. and Wong, C.W., "Alzheimer's Disease: Initial Report of the Purification and Characterization of a Novel Cerebrovascular Amyloid Protein," *Biochem. Biophys. Res. Comm.* 120(3):885–890 (1984).

Guiroy, D.C. et al., "Amyloid of neurofibrillary tangles of Guamanian parkinsonism–dementia and Alzheimer disease share identical amino acid sequence," *Proc. Natl. Acad. Sci. USA* 84:2073–2077 (1987).

Haass, C. et al., "Amyloid β–peptide is produced by cultured cells during normal metabolism," *Nature* 359:322–325 (1992).

Hershey, C.O. et al., "Cerebrospinal fluid trace element content in dementia: Clinical, radiologic, and pathologic correlations," *Neurology* 33:1350–1353 (1983).

Hilbich, C. et al., "Aggregation and Secondary Structure of Synthetic Amyloid βA4 Peptides of Alzheimer's Disease," *J. Mol. Biol.* 218:149–163 (1991).

Hilbich, C. et al., "Substitutions of Hydrophobic Amino Acids Reduce the Amyloidogenicity of Alzheimer's Disease βA4 Peptides," *J. Mol. Biol.* 228(2):460–473 (1992).

Howell, G.A. et al., "Stimulation–induced uptake and release of zinc in hippocampal slices," *Nature* 308:736–738 (1984).

Hyman, B.T. et al., "Perforant Pathway Changes and the Memory Impairment of Alzheimer's Disease," *Ann. Neurol.* 20:472–481 (1986).

Jarrett, J.T. et al., "The Carboxy Terminus of the β Amyloid Protein Is Critical for the Seeding of Amyloid Formation: Implications for the Pathogenesis of Alzheimer's Disease," *Biochemistry* 32(18):4693–4697 (May 1993).

Johnstone, E.M. et al., "Conservation of the sequence of the Alzheimer's disease amyloid peptide in dog, polar bear and five other mammals by cross–species polymerase chain reaction analysis," *Molec. Brain Res.* 10:299–305 (1991).

Kim, K.S. et al., "Detection and Quantitation of Amyloid B–Peptide with 2 Monoclonal Antibodies," *Neurosci. Res. Comm.* 7(2):113–122 (1990).

Koh, J.Y. et al., "β–Amyloid protein increases the vulnerability of cultured cortical neurons to excitotoxic damage," *Brain Res.* 533:315–320 (1990).

Koo, E.H. et al., "Amyloid β–protein as a substrate interacts with extracellular matrix to promot neurite outgrowth," *Proc. Natl. Acad. Sci. USA* 90:4748–4752 (May 1993).

Lindbladh, C. et al., "Use of genetically prepared enzyme conjugates in enzyme immunoassay," *TI* 18:279–283 (Aug. 1993).

Lui, E. et al., "Metals and the Liver in Alzheimer's Disease: An Investigation of Hepatic Zinc, Copper, Cadmium, and Metallothionein," *JAGS* 38:633–639 (1990).

Mantyh, P.W. et al., "Aluminum, Iron, and Zinc Ions Promote Aggregation of Physiological Concentrations of β–Amyloid Peptide," *J. Neurochem.* 61(3):1171–1174 (Sep. 1993).

Masters, C.L. et al., "Amyloid plaque core protein in Alzheimer disease and Down syndrome," *Proc. Natl. Acad. Sci. USA* 82:4245–4249 (1985).

Masters, C.L. et al., "Neuronal origin of a cerebral amyloid: neurofibrillary tangles of Alzheimer's disease contain the same protein as the amyloid of plaque cores and blood vessels," *EMBO J.* 4(11):2757–2763 (1985).

Milward, E.A. et al., "The Amyloid Protein Precursor of Alzheimer's Disease Is a Mediator of the Effects of Nerve Growth Factor on Neurite Outgrowth," *Neuron* 9:129–137 (1992).

Pérez–Clausell, J. and Danscher, G., "Intravesicular Localization of Zinc in Rat Telencephalic Boutons. A Histochemical Study," *Brain Res.* 337:91–98 (1985).

Perl, D.P. and Brody, A.R., "Alzheimer's Disease: X–ray Spectrometric Evidence of Aluminum Accumulation in Neurofibrillary Tangle–Bearing Neurons," *Science* 208:297–299 (1980).

Perl, D.P. et al., "Intraneuronal Aluminum Accumulation in Amyotrophic Lateral Sclerosis and Parkinsonism–Dementia of Guam," *Science* 217:1053–1055 (1982).

Rumble, B. et al., "Amyloid A4 Protein and its Precursor in Down's Syndrome and Alzheimer's Disease," *New Eng. J. Med.* 320(22):1446–1452 (1989).

Schubert, W. et al., "Localization of Alzheimer βA4 amyloid precursor protein at central and peripheral synaptic sites," *Brain Res.* 563:184–194 (1991).

Seubert, P. et al., "Isolation and quantification of soluble Alzheimer's β–peptide from biological fluids," *Nature* 359:325–327 (1992).

Shivers, B.D. et al., "Alzheimer's disease amyloidogenic glycoprotein: expression pattern in rat brain suggests a role in cell contact," *EMBO J.* 7(5):1365–1370 (1988).

Shoji, M. et al., "Production of the Alzheimer Amyloid β Protein by Normal Proteolytic Processing," *Science* 258:126–129 (1992).

Sisodia, S.S. et al., "Evidence That β–Amyloid Protein in Alzheimer's Disease Is Not Derived by Normal Processing," *Science* 248:492–495 (1990).

Stewart, G.R. et al., "Cholinergic Denervation–Induced Increase of Chelatable Zinc in Mossy–Fiber Region of the Hippocampal Formation," *Brain Res.* 290:43–51 (1984).

Suzuki, N. et al., "High Tissue Content of Soluble β1–40 is Linked to Cerebral Amyloid Angiopathy," *Am. J. Path.* 145(2):452–460 (1994).

Tomski, S.J. and Murphy, R.M., "Kinetics of Aggregation of Synthetic β–Amyloid Peptide," *Arch. Biochem. Biophys.* 294(2):630–638 (1992).

Uchida, Y. et al., "The Growth Inhibitory Factor That Is Deficient in the Alzheimer's Disease Brain Is a 68 Amino Acid Metallothionein–Like Protein," *Neuron* 7:337–347 (1991).

Vaughan, D.W. and Peters, A., "The Structure of Neuritic Plaques in the Cerebral Cortex of Aged Rats," *J. Neuropathol. Exp. Neurol.* 40(4):472–487 (1981).

Weiss, J.H. et al., "Zinc and LTP," *Nature* 338:212 (1989).

Wenstrup, D. et al., "Trace element imbalances in isolated subcellular fractions of Alzheimer's disease brains," *Brain Res.* 533:125–131 (1990).

Wolf, G. et al., "Uptake and Subcellular Distribution of $^{65}$Zinc in Brain Structures During the Postnatal Development of the Rat," *Neurosci. Lett.* 51:277–280 (1984).

Xie, X. and Smart, T.G., "A physiological role for endogenous zinc in rat hippocampal synaptic neurotransmission," *Nature* 349:521–524 (1991).

Yankner, B.A. et al., "Neurotrophic and Neurotoxic Effects of Amyloid β Protein: Reversal by Tachykinin Neuropeptides," *Science* 250:279–282 (1990).

Volles et al., Alternative Immunoassays, Ed. W. P. Collins, 1985 John Wiley & Sons Ltd. pp. 77–86.

Campbell, A.M., Laboratory Techniques in Biochemistry and Molecular Biology, vol. 23, 1991, Elsevier pp. 1–6.

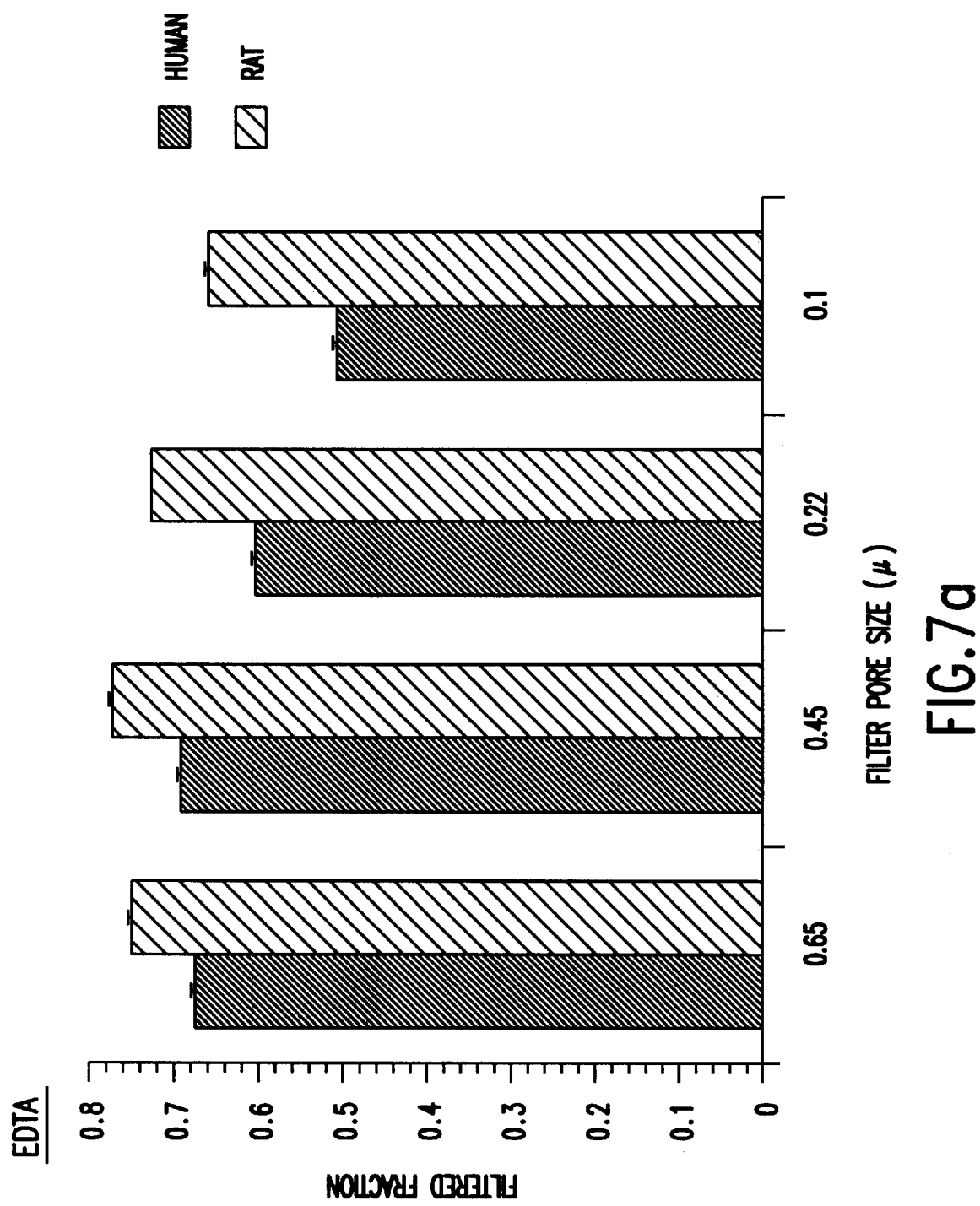

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
       (A) LENGTH: 43 amino acids
       (B) TYPE: amino acid
       (C) STRANDEDNESS: single
       (D) TOPOLOGY: Not Relevant (ii) MOLECULE TYPE: peptide (xi) SEQUENCE DESCRIPTION: SEQ ID NO:1:

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
                20                  25                  30

Gly Leu Met Val Gly Gly Val Val Ile Ala Thr
            35                  40

DIAGNOSTIC ASSAY FOR ALZHEIMER'S DISEASE: ASSESSMENT OF Aβ ABNORMALITIES

STATEMENT AS TO RIGHTS TO INVENTIONS MADE UNDER FEDERALLY-SPONSORED RESEARCH AND DEVELOPMENT

Part of the work performed during the development of this invention utilized U.S. Government Funds under Grants Nos. RO1 NS3048-03 and RO1 AG11899-01 from The National Institutes of Health (NIH). The government may have certain rights in this invention.

BACKGROUND OF THE INVENTION

1. Field of the Invention

The purpose of this invention is to assay the quantity and quality of Aβ peptide in Alzheimer's disease (AD) and Aβ amyloidotic disorders related to Alzheimer's disease. Specifically, the invention proposes to achieve this end by enriching the peptide by capturing it from biological fluids such as plasma, serum, cerebrospinal fluid or urine with a zinc- or copper-chelated microwell plate, and then measuring the amounts of captured Aβ with specific anti-Aβ antibodies in an ELISA.

2. Related Art

Alzheimer's disease is characterized pathologically by the accumulation in the brain of Aβ protein. The Aβ protein is a small peptide that is also found in cerebrospinal fluid and plasma. Much evidence implicates the accumulation of Aβ in the pathogenesis of the disease, either as the neurotoxic agent itself or as a hallmark which accompanies neurotoxicity in the disorder. Aβ accumulates as a highly insoluble deposit within neuronal tissues. It is desirable to discover a treatment which would reverse the deposition and relieve or arrest clinical deterioration.

Aggregation of Aβ in the brain is believed to contribute to the progressive dementia, characteristic of Alzheimer's disease (AD) and to the premature AD observed among Down's syndrome patients. Aβ, a 4.3-kDa peptide, is the principal constituent of the cerebral amyloid deposits, a pathological hallmark of Alzheimer's disease (AD) (Masters et al., Proc. Natl. Acad. Sci. USA 82:4245–4249 (1985); Glenner & Wong, Biochem. Biophys. Rev. Commun. 120:885–890 (1984)). Aβ is derived from the much larger amyloid protein precursor (APP) (Kang et al., Nature 325:733–736 (1987); Tanzi et al., Science 235:880–884 (1987); Robakis et al., Proc. Natl. Acad. Sci. USA 84:4190–4194 (1987); Goldgaber et al., Science 235:877–880 (1987)), whose physiological function remains unclear. The cause of Alzheimer's disease remains elusive; however, the discovery of mutations of APP close to or within the Aβ domain (Goate et al., Nature 349:704–706 (1991); Levy et al., Science 248:1124–1126 (1990); Murrell et al., Science 254:97–99 (1991); Hendricks et al., Nature Genet. 1:218–221 (1992), linked to familial AD (FAD) (E. Levy et al., Science 248:1124 (1990); Aβ Goate et al., Nature 349:704 (1991); M. Chartier-Harlin et al., Nature 353:844 (1991); J. Murrell, M. Farlow, B. Ghetti, M. D. Benson, Science 254:97 (1991); L. Hendricks et al., Nature Genet. 1:218 (1992); M. Mullan et al., Nature Genet. 1:345 (1992)), indicates that the metabolism of Aβ and APP is likely to be intimately involved with the pathophysiology of this disorder.

Alzheimer's disease affects 10% of individuals over the age of 60, however, the existence of Aβ deposits in 40% of the brains of normal individuals in their forties suggests an even larger subclinical prevalence. Hence, the disease process is likely to be very common, with individual thresholds of neuronal and functional reserve being responsible for the varying onset of clinical symptoms. The disease is debilitating, chronic, incurable and very expensive to treat and an effective prevention or therapy would have an enormous commercial market. However, there are no reliable biochemical markers for AD.

FAD patients with the "Swedish" APP mutation overproduce the soluble, secreted form of Aβ and suffer from early onset (<60 years) AD (Citron et al., Nature 360:672–674 (1992)). A potential neuropathogenic mechanism has been reported by Younkin and colleagues (Society for Neuroscience, Mol. Genet. Med. 3:95–137 (1993)) for the APP 717 mutations which account for 90% of the APP mutations causing FAD. These mutations apparently lead to an increase in the ratio of "long" Aβ (1–42) to Ad (1-40). Aβ (1-40) is the predominant species in the cerebrospinal fluid (CSF), and is a relatively soluble peptide. Aβ (1-42) is significantly more amyloidogenic, and its overproduction relative to the 1-40 species appears to lead to early-onset AD in these patients. Therefore, levels of Aβ (1-40) and Aβ (1-42) in the cerebrospinal fluid (CSF), plasma, serum or urine may be expected to correlate with cerebral pathology in sporadic AD cases, the predominant clinical form of the disorder.

Two protocols currently exist for the estimation of Aβ levels in biological fluids. The first involves the immunoprecipitation of Aβ with specific anti-Aβ antibodies (e.g. Haass et al., Nature 359:322–325 (1992); Citron et al., Nature 360:672–674 (1992)), a technique which is, at best, semiquantitative. This technique was used in combination with western blotting to measure Aβ levels in CSF (Shoji et al., Science 258:126–129 (1992)) but found no gross differences between AD and control specimens. A double antibody capture ELISA using monoclonal antibodies raised against Aβ appears to give specific Aβ quantification with a sensitivity limit at about 0.6 nM (Seubert et al., Nature 359:325–327 (1992)).

The double antibody ELISA is more widely used and is the only described means of accurately quantifying Aβ. It has two important limitations. It requires an abundance of expensive antibody to coat the wells of microwell plates in order to capture the Aβ from the biological fluid. A second anti-Aβ antibody, at a higher dilution, is used to detect captured Aβ. The second limitation of the double-antibody capture ELISA technique for Aβ assay is that it requires a fluorescence-generating enzyme-conjugated detection antibody and a fluorescence microwell plate reader for the final step of the assay.

Fluorescence plate readers are highly specialized and expensive (about $30,000, Millipore Cytofluor), which limits the accessibility of the technique. Fluorescence has been preferred over more versatile, and cheaper, chromogenic assays (e.g., horse radish peroxidase-conjugated detection antibody acting on a chromogenic substrate), because it lowers the limit of sensitivity allowing the measurement of Aβ at the levels found in biological fluids. No Aβ assay has been described where the development of a chromogenic substrate was measured by a visible-light microwell plate reader, a far less expensive instrument (e.g., $8,000).

The Aβ species assay of the present invention will provide a rational basis to monitor response to putative treatments for AD, as well as providing early diagnostic information if clinical outcome studies validate the correlation of the Aβ levels in the blood or CSF with disease progression.

SUMMARY OF THE INVENTION

It has now been found that Aβ strongly and specifically binds zinc and copper in a pH dependent manner. These binding properties of Aβ have been exploited in this invention to create a novel means of capturing Aβ from biological fluids with a zinc- or copper-treated microwell plate, as well as a novel means for the bulk chromatographic purification of Aβ from biological fluids.

An advantage of this new ELISA technique over the previously described double antibody capture ELISA is that it obviates the need for a capture antibody (saving reagents and expense) and, because zinc- and copper-mediated capture appears to be more efficient than immobilized antibody capture, it is over an order of magnitude more sensitive than the reported sensitivity of double antibody capture ELISA. Hence, the assay results with biological fluids can be achieved using cheaper chromogenic substrates, in conjunction with a visible-light microwell plate reader.

In the present invention, an assay is designed to quantify the amount of Aβ peptide present in a solution such as a biological fluid. To do so, a solid substrate is used to which a zinc (II) and/or copper (II) complex is immobilized. Preferably, the metal is complexed with immobilized nitriloacetic acid. The substrate is then contacted with the biological fluid. The free coordination sites on the zinc or copper atom act as a capture trap for Aβ peptide which can then be detected and quantified in a number of different ways.

The levels of Aβ are believed to correlate with the cerebral pathology of AD. However, the more highly amyloidogenic 1-42 species of Aβ may be more important in AD pathology than other species such as the 1-40 form. The present invention allows levels of the different species of Aβ to be measured by use of antibodies that are specific to 1-42 species and do not recognize the 1-40 form. Such antibodies are produced preferrably from mice (although they may be produced from Guinea pigs, rabbits, rats, goats, sheep, horses,et cetera.) by injection with peptides containing the unique 40-42 region of the 1-42 species (peptides comprising the Aβ sequence from residue 42 to any residue less than 38 are suitable immunogens). A monoclonal antibody that is specific to the 1-42 species of Aβ may be selected by testing for imrunoreactivity to different Aβ species that have been immobilized on a zinc or copper treated microwell plate.

Therefore, the first aspect of the invention relates to a diagnostic assay for detecting and/or quantifying Aβ peptide which may be present in a candidate solution, comprising:

(a) contacting the candidate solution with a solid support with a heavy metal cation immobilized thereon to capture Aβ peptide on the surface of the solid support, thereby forming a first complex which comprises solid support/heavy metal cation/Aβ peptide;

(b) blocking all exposed metal binding sites remaining after Aβ capture with a blocker;

(c) contacting the first complex, which has been passed through step (b), with an antibody specific for Aβ peptide to form a second complex which comprises solid support/heavy metal cation/Aβ peptide/antibody specific for Aβ peptide;

(d) labelling the second complex to form a detectable third complex which comprises solid support/heavy metal cation/Aβ peptide/antibody specific for Aβ peptide/label; and (e) detecting the third complex, and quantifying Aβ peptide which may be present in the candidate solution.

A second aspect of the invention relates to a diagnostic assay for detecting and/or quantifying Aβ peptide which may be present in a candidate solution, comprising:

(a) contacting the candidate solution with a solid support with a heavy metal cation immobilized thereon to capture Aβ peptide on the surface of the solid support, thereby forming a first complex which comprises solid support/heavy metal cation/Aβ peptide;

(b) blocking all exposed metal binding sites remaining after Aβ capture with a blocker;

(c) contacting the first complex, which has been passed through step (b), with an antibody specific for Aβ peptide, called Aβ antibody, to form a second complex which comprises solid support/heavy metal cation/Aβ peptide/Aβ antibody;

(d) contacting said second complex with one or more anti-antibodies specific to the Aβ antibody to form a third complex which comprises solid support/heavy metal cation/Aβ peptide/Aβ antibody/one or more anti-antibodies;

(e) labelling said third complex to form a detectable fourth complex which comprises solid support/heavy metal cation/Aβ peptide/Aβ antibody/one or more anti-antibodies/label; and (f) detecting the fourth complex, thereby quantifying Aβ peptide which may be present in the candidate solution.

The preferred heavy metal cations used in the practice of the present invention are zinc (II) or copper (II) complexed to nitriloacetic acid. Other organic ligands which may be used to complex the heavy metal, e.g. copper and zinc, are, but not limited to, iminodiacetic acid, tris(carboxymethyl) ethylenediamine,N,N,N,N,N-carboxy(methyl) tetraethylenepentamine, and methionine-polyethyleneglycol (for other such compounds, see F. H. Arnold, *Biotechnology* 9:151–156 (1991), e.g., at page 154).

The preferred antibodies used in the practice of the invention are those that are either specific to $A\beta_{1-42}$ which do not cross react with $A\beta_{1-40}$ or specific to $A\beta_{1-40}$ which do not cross react with $A\beta_{1-42}$.

In the preferred embodiments of the invention, the antibodies specific to Aβ protein are labelled with a radioisotope (radioactive isotope), which can then be determined by such means as the use of a gamma counter or a scintillation counter. Isotopes which are particularly useful for the purpose of the present invention are: $^3H$, $^{125}I$, $^{131}I$, $^{32}P$, $^{35}S$, $^{14}C$, $^{51}Cr$, $^{36}Cl$, $^{57}Co$, $^{58}Co$ $^{59}Fe$ and $^{75}Se$. In other prefered embodiments of the invention, the antibodies specific to Aβ protein are labelled by conjugating them to enzymes which can be detected when conjugated to said antibody, such as, but not limited to, fluorescence-generating enzymes, as well as chromogenic enzymes like alkaline phosphatase, urease, and horseradish peroxidase.

The body fluids that are assayed by the diagnostic assays of the present invention, are preferably pretreated as described in the Examples.

Another aspect of the invention relates to kits for carrying out the aforementioned assays which comprise a carrier means, compartmentalized in close confinement therein to receive one or more container means, which comprises a first container means containing a solid support having a heavy metal cation immobilized thereon and a second container means containing an antibody specific for Aβ peptide.

A further aspect of the invention relates to kits for carrying out the above-mentioned assays, which comprise a carrier means, compartmentalized in close confinement therein to receive one or more container means, which comprises a first container means containing a solid support having a heavy metal cation immobilized thereon, a second container means containing an antibody specific for Aβ protein, and a third container means containing an anti-antibody which is specific for the antibody in the second container means. Preferably, the anti-antibody is detectably labeled.

A further aspect of the invention relates to kits preferably used for carrying out the above-mentioned assays with biological fluids, which comprise a carrier means, compartmentalized in close confinement therein to receive one or more container means, which comprises a first container means containing a solid support having a heavy metal cation immobilized thereon, a second container means containing an antibody specific for Aβ protein, a third container means containing an anti-antibody which is specific for the antibody in the second container means, and a fourth container means containing a methylating compound.

Another aspect of the invention relates to kits preferably used for carrying out the above-mentioned assays with biological fluids, which comprise a carrier means, compartmentalized in close confinement therein to receive one or more container means, which comprises a first container means containing a solid support having a heavy metal cation immobilized thereon, a second container means containing an antibody specific for Aβ protein, a third container means containing an anti-antibody which is specific for the antibody in the second container means, a fourth container means containing a methylating compound, and a fifth container means containing magnesium chloride.

Another aspect of the invention relates to kits preferably used for carrying out the above-mentioned assays with biological fluids, which comprise a carrier means, compartmentalized in close confinement therein to receive one or more container means, which comprises a first container means containing a solid support having a heavy metal cation immobilized thereon, a second container means containing an antibody specific for Aβ protein, a third container means containing an anti-antibody which is specific for the antibody in the second container means, a fourth container means containing a methylating compound, a fifth container means containing magnesium chloride, and a sixth container means containing a blocker.

Yet, another aspect of the invention relates to kits for carrying out the assays of the present invention which comprises a carrier means, compartmentalized in close confinement therein to receive one or more container means, which comprises a first container means containing a solid support having a heavy metal cation immobilized thereon and a second container means containing a labelled antibody specific for Aβ protein.

Another aspect of the invention relates to kits preferably used for carrying out the assays of the present invention with biological fluids which comprises a carrier means, compartmentalized in close confinement therein to receive one or more container means, which comprises a first container means containing a solid support having a heavy metal cation immobilized thereon, a second container means containing a labelled antibody specific for Aβ protein, and a third container means containing a methylating compound.

A further aspect of the invention relates to kits preferably used for carrying out the assays of the present invention with biological fluids which comprises a carrier means, compartmentalized in close confinement therein to receive one or more container means, which comprises a first container means containing a solid support having a heavy metal cation immobilized thereon, a second container means containing a labelled antibody specific for Aβ protein, a third container means containing a methylating compound, and a fourth container means containing magnesium chloride.

Another aspect of the invention relates to kits preferably used for carrying out the assays of the present invention with biological fluids which comprises a carrier means, compartmentalized in close confinement therein to receive one or more container means, which comprises a first container means containing a solid support having a heavy metal cation immobilized thereon, a second container means containing a labelled antibody specific for Aβ protein, a third container means containing a methylating compound, a fourth container means containing magnesium chloride, and a fifth container means containing a blocker.

The next aspect of the invention relates to kits for carrying out the aforementioned assays which comprise a carrier means, compartmentalized in close confinement therein to receive one or more container means, which comprises a first container means containing a solid support having a heavy metal cation immobilized thereon and a second container means containing an antibody specific for Aβ protein bound to a labelled anti-antibody.

Another aspect of the invention relates to kits preferably used for carrying out the aforementioned assays with biological fluids which comprise a carrier means, compartmentalized in close confinement therein to receive one or more container means, which comprises a first container means containing a solid support having a heavy metal cation immobilized thereon, a second container means containing an antibody specific for Aβ protein bound to a labelled anti-antibody, and a third container means containing a methylating compound.

A further aspect of the invention relates to kits preferably used for carrying out the aforementioned assays with biological fluids which comprise a carrier means, compartmentalized in close confinement therein to receive one or more container means, which comprises a first container means containing a solid support having a heavy metal cation immobilized thereon, a second container means containing an antibody specific for Aβ protein bound to a labelled anti-antibody, a third container means containing a methylating compound, and a fourth container means containing magnesium chloride.

A further aspect of the invention relates to kits preferably used for carrying out the aforementioned assays with biological fluids which comprise a carrier means, compartmentalized in close confinement therein to receive one or more container means, which comprises a first container means containing a solid support having a heavy metal cation immobilized thereon, a second container means containing an antibody specific for Aβ protein bound to a labelled anti-antibody, a third container means containing a methylating compound, a fourth container means containing magnisium chloride and a fifth container means containing a blocker.

Another aspect of the invention relates to a method for purification of Aβ peptide from biological fluids containing one or more proteins which comprises:

(a) methylating cysteine groups of the proteins in the biological fluid;
(b) acidifying the biological fluid obtained from step (a);
(c) applying the biological fluid obtained from step (b) to a copper-charged chelating-Sepharose column;
(d) washing the column with equilibration buffer to obtain an eluate solution; and
(e) collecting the eluate solution, thereby obtaining purified Aβ peptide.

Another aspect of the invention relates to a method for purification of Aβ peptide from biological fluids containing one or more proteins which comprises:

(a) methylating cysteine groups of the proteins in the biological fluid;

(b) acidifying the biological fluid obtained from step (a);

(c) adding to the biological fluid obtained from step (b), a free copper-charged chelating slurry to form a mixture;

(d) centrifuging the mixture obtained from step (c) to obtain a pellet;

(e) washing the pellet obtained from step (d) with equilibration buffer, thereby obtaining purified Aβ peptide.

A further aspect of the invention relates to a kit for carrying out the method for bulk purification of Aβ peptide in biological fluids which comprises a carrier means compartmentalized in close confinement therein to receive one or more container means which comprises a first container means containing a copper charged chelating-Sepharose column and a second container means containing an antibody specific for Aβ peptide which may be used to confirm presence of purified β peptide.

Finally, another aspect of the invention relates to a kit for carrying out the method of purifying Aβ peptide from biological fluids which comprises a carrier means compartmentalized in close confinement therein to receive one or more container means which comprises a first container means containing free copper-charged chelating-Sepharose and a second container means containing an antibody specific for Aβ peptide which may be used to confirm presence of purified Aβ peptide.

Neurochem 61:1171 (1993) (15,000 CPM, the kind gift of Dr. John Maggio, Harvard Medical School) was added to unlabeled A$\beta_{1-40}$ (1.6 μM) as a tracer, incubated and filtered as described above. The CPM in the filtrate and retained on the excised filter were measured by a γ-counter. (6c) A bar graph showing the proportion of A$\beta_{1-40}$ (1.6 μM) filtered through 0.2μ following incubation with various metal ions (3 μM). The atomic number of the metal species is indicated. (6d) A graph showing the effects of $Zn^{2+}$ (25 μM) or EDTA (50 μM) upon kinetics of human A$\beta_{1-40}$ aggregation measured by 0.2μ filtration. Data points are in duplicate.

FIGS. 7a, 7b, 7c and 7d depict bar graphs showing the size estimation of zinc-induced Aβ aggregates. (7a and 7b) Bar graphs showing the proportion of A$\beta_{1-40}$ (1.6 μM in 100 mM NaCl, 20 mM Tris-HCl, pH 7.4 (buffer 1), incubated±$Zn^{2+}$ (25 μM) or EDTA (50 μM) and then filtered through filters of indicated pore sizes (Durapore filters (Ultrafree-MC, Millipore) were used for this study, hence there is a slight discrepancy between the values obtained with the 0.22μ filters in this study compared to values obtained in FIG. 6 using 0.2μ Costar filters). (7c) A bar graph showing $^{65}ZnCl_2$ (130,000 CPM, 74 nM) used as a tracer of the assembly of the zinc-induced aggregates of human A$\beta_{1-40}$ produced in FIGS. 7a and 7b. By determining the amounts of A$\beta_{1-40}$ and $^{65}Zn$ in the filtrate, the quantities retarded by the filters could be determined, and the stoichiometry of the zinc: Aβ assemblies estimated. (7d) Bar graph. Following this procedure, the filters, retaining Zn: Aβ assemblies, were washed with buffer 1 (100 mM NaCl, 20 mM Tris-HCl, pH 7.4)+EDTA (50 μM×300 μl, 700 g, 4 minutes). The amounts of zinc-precipitated A$\beta_{1-40}$ resolubilized in the filtrate fraction were determined by $OD_{214}$, and expressed as a percentage of the amount originally retained by the respective filters. $^{65}Zn$ released into the filtrate was measured by γ-counting.

Figure 8A:
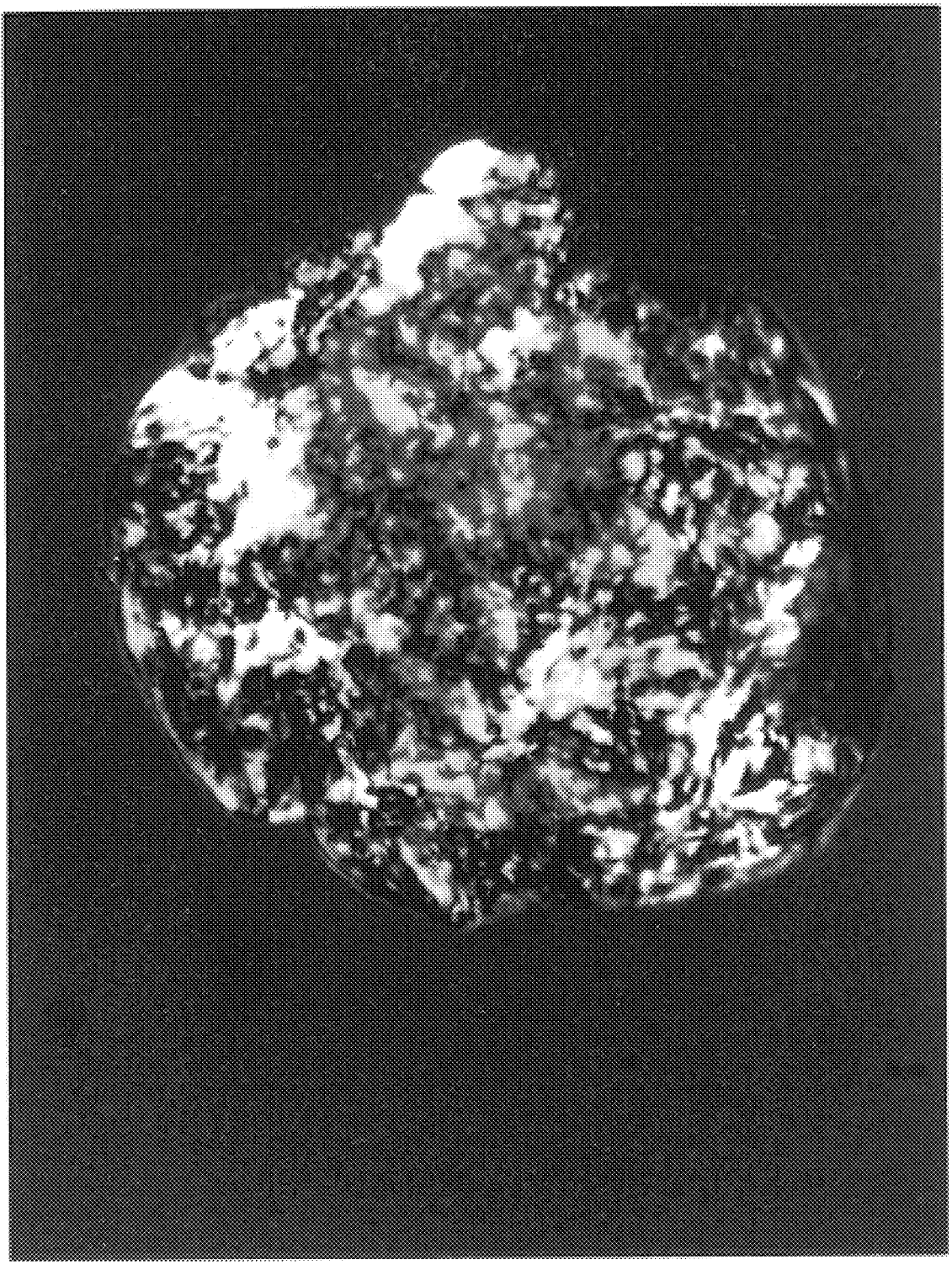
Figure 8B:
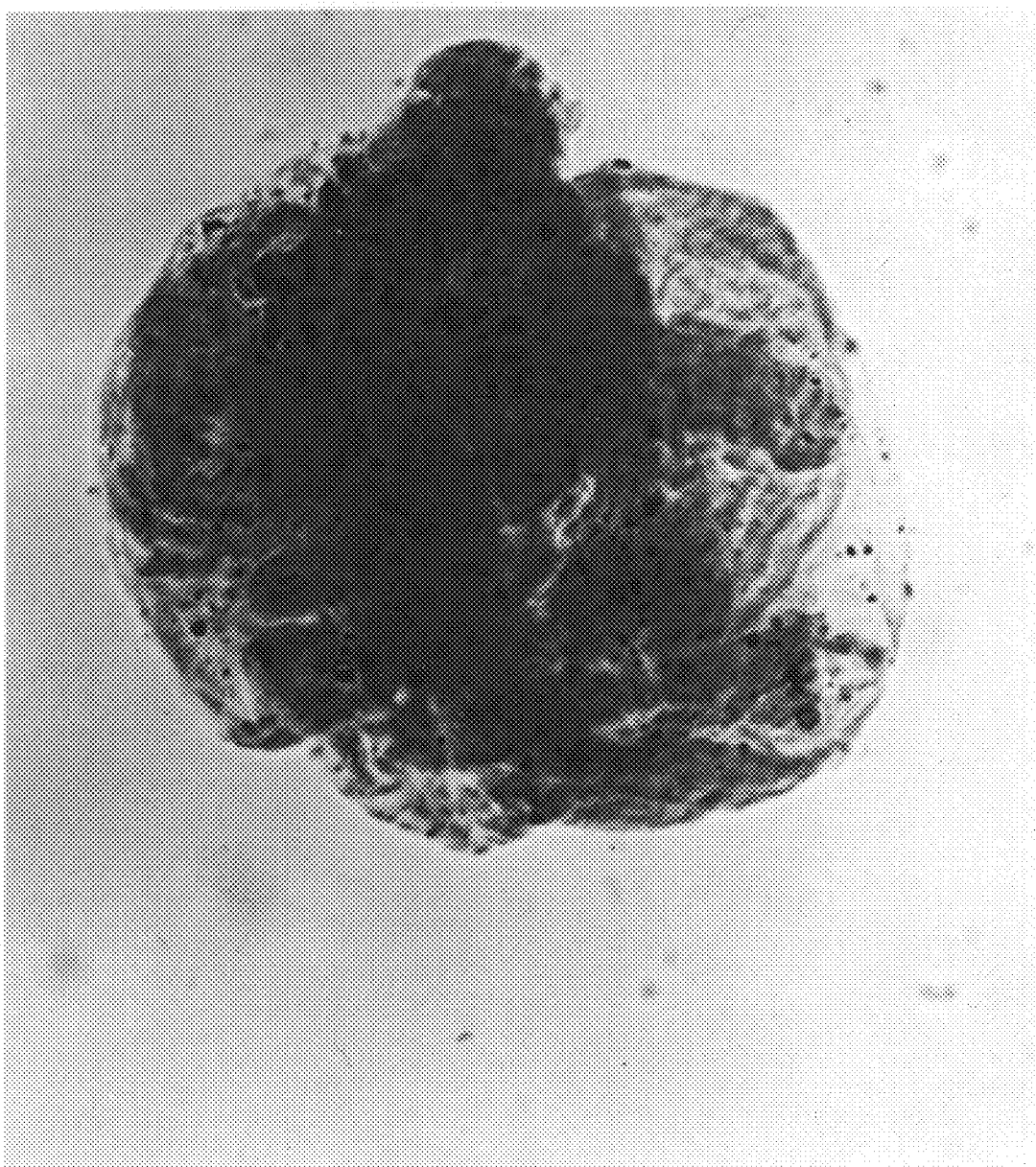

FIGS. 8a and 8b are photographs showing zinc-induced tinctorial amyloid formation. (8a) Zinc-induced human A$\beta_{1-40}$ precipitate stained with Congo Red. The particle diameter is 40μ. A$\beta_{1-40}$ (200 μl×25 μM in buffer 1 (100 mM NaCl, 20 mM Tris-HCl, pH 7.4)) was incubated (30 minutes, 37° C.) in the presence of 25 μM $Zn^{2+}$. The mixture was then centrifuged (16,000 g×15 minutes), the pellet washed in buffer 1 (100 mM NaCl, 20 mM Tris-HCl, pH 7.4)+EDTA (50 μM), pelleted again and resuspended in Congo Red (1% in 50% ethanol, 5 minutes). Unbound dye was removed, the pellet washed with buffer 1 (100 mM NaCl, 20 mM Tris-HCl, pH 7.4) and mounted for microscopy. (8b) The same aggregate visualized under polarized light, manifesting green birefringence. The experiment was repeated with EDTA (50 μM) substituted for $Zn^{2+}$ and yielded no visible material.

Figure 9:
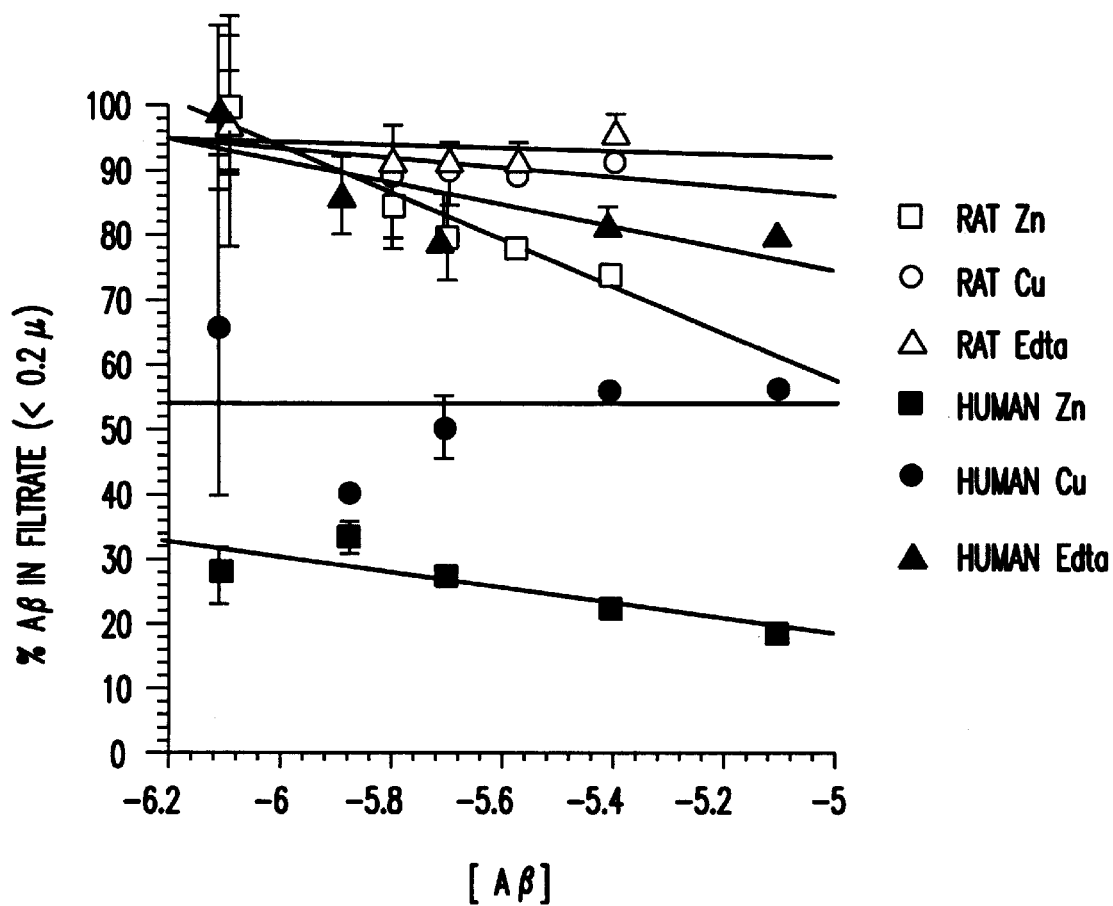

FIG. 9 depicts a graph showing the effect of zinc and copper upon human, $^{125}I$-human and rat A$\beta_{1-40}$ aggregation into >0.2μ particles. Stock human and rat A$\beta_{1-40}$ peptide solutions (16 μM) in water were pre-filtered (Spin-X, Costar, 0.2μ cellulose acetate, 700 g), brought to 100 MM NaCl, 20 mM Tris-HCl, pH 7.4 (buffer 1)±EDTA (50 μM) or metal chloride salts, incubated (30 minutes, 37° C.) and then filtered again (700 g, 4 minutes). The fraction of the A$\beta_{1-40}$ in the filtrate was calculated by the ratio of the filtrate $OD_{214}$ (the response of the $OD_{214}$, titrated against human and rat A$\beta_{1-40}$ concentrations (up to 20 μM in the buffers used in these experiments), was determined to be linear) relative to the $OD_{214}$ of the unfiltered sample. All data points are in triplicate, unless indicated. (FIG. 9) The graph shows the proportions of A$\beta_{1-40}$, incubated±$Zn^{2+}$ (25 μM) or $Cu^{2+}$ or EDTA (50 μM) and then filtered through 0.2μ, titrated against peptide concentration.

FIG. 10 depicts the amino acid sequence of human Aβ peptide. The amino acid sequence of human Aβ peptide (SEQ ID NO:1) is depicted and amino acid positions are numbered.

Figure 11:
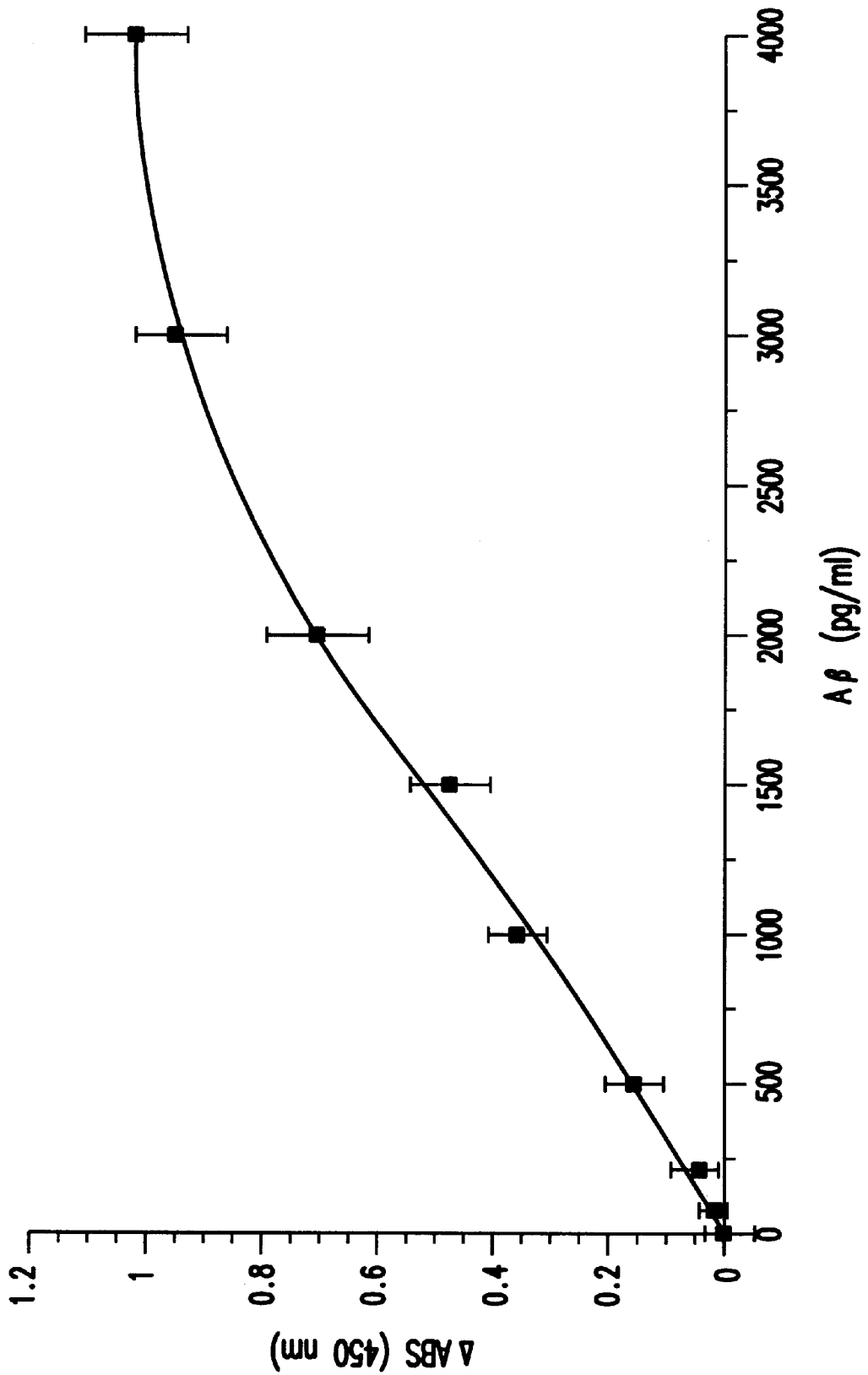

FIG. 11 depicts a standard curve graph for increasing Aβ concentration on an ELISA using a copper coated 96-well plate for solid phase capture. Values are shown±S.D. n=3. Increasing concentrations of Aβ were prepared in coating buffer (Tris 20 mM, pH 7.4 and NaCl 150 mM). Aliquots (200 μl) were transferred to the wells of a copper-treated 96-well plate ((copper (II) was immobilized on the well surface with nitriloacetic acid) and incubated for 2 h at 37° C. The solution in the wells was removed and replaced with 300 μl per well of blocking buffer (2% gelatin in Tris 20 mM, pH 8 and NaCl 150 mM) and the plate incubated at 37° C. for a further 2 h. The wells were washed two times with 300 μl aliquot's of washing buffer (Tris 20 mM, pH 8 and NaCl 150 mM) before being incubated (2 h at 37° C.) with a primary antibody (200 μl per well of antibody diluted ¹⁄₁₀₀₀ with blocking buffer containing a reduced gelatin concentration (0.2%)) directed at the N-terminus of Aβ (a now commercially available mouse monoclonal antibody supplied by Dr. S. K. Kim of the NY State Institute for Basic Research in Developmental Disabilities). The wells were washed three times with washing buffer before the addition of anti-mouse-antibody-HRPO conjugate (200 μl per well of a ¹⁄₁₀₀₀ dilution in 0.2% gelatin blocking buffer) and a final incubation at 37° C. for 2 h. The wells were washed three times with washing buffer and one final rinse in water before the addition of 200 μl per well of HRPO substrate solution (Pierce, 34024). After a 30 minute incubation at room temperature (18–22° C.) a 25 μl aliquot of 2 M $H_2SO_4$ was added to each well and absorbance of the plate measured at 450 nm. The average background absorbance (wells containing no Aβ) was subtracted from the absorbance of Aβ standards and the resulting values plotted against peptide concentration.

Other features and advantages of the invention will be apparent from the following detailed description, and from the claims.

DETAILED DESCRIPTION OF THE PREFERRED EMBODIMENTS

β$_{1-40}$, the major component of Alzheimer's disease cerebral amyloid is relatively soluble at high concentrations (≦3.7 mM) and has been detected in CSF and blood. Physiological factors which decrease solubility and induce Aβ amyloid formation may be important in the pathogenesis of the disease. It has been discovered that human Aβ specifically and saturably binds zinc, and that concentrations of this metal ion above 300 nM rapidly destabilize human A$\beta_{1-40}$ solutions, inducing tinctorial amyloid formation. High-affinity binding ($K_A$=107 nNM) compatible with normal CSF zinc levels, and low-affinity binding ($K_A$=5.2 μM) have now been shown. In contrast, rat A$\beta_{1-40}$ binds zinc less avidly and does not aggregate in its presence, suggesting a possible explanation for lack of cerebral Aβ amyloid in these animals. Collectively, these data suggest a potentially critical role for cerebral zinc metabolism in the neuropathogenesis of Alzheimer's disease.

Further, it has been observed that abnormalities of zinc homeostasis occur in AD and DS patients. Cerebral zinc homeostasis, which has been reported to be abnormal in AD (D. Wenstrup, W. D. Ehmann, W. R. Markesbery, Brain Res. 533:125 (1990); J. Constantinidis, Encephale 16:231 (1990); F. M. Corrigan, G. P. Reynolds, N. I. Ward, Biometals 6:149 (1993); C. O. Hershey et al., *Neurology* 33:1350 (1983)) may be important for the metabolic fate of Aβ since increased concentrations of zinc promote the peptide's adhesiveness and resistance to proteolytic digestion. Moreover, oral zinc supplementation has recently been shown to have an acutely adverse effect on cognition in AD subjects, but not age-matched controls indicated that environmental or nutritional zinc exposure may be a contributing factor to AD pathophysiology.

The present findings have indicated that Aβ strongly and specifically binds zinc in a pH dependent manner. In the brain milieu, these metal ions are present in sufficient concentration to exert these effects on binding and solubility. A decrease in Aβ i solubility occurs in the presence of concentrations of zinc as low as 0.3 μM. Occupation of the zinc binding site on Aβ increases the resistance of the peptide to tryptic digestion at the α-secretase site. α-Secretase is an, as yet, unidentified protease which has been observed to cleave the precursor molecule of Aβ, the Amyloid Protein Precursor (APP) within the AdO domain, rendering Aβ incapable of accumulating. Hence, occupation of the zinc binding site on Aβ will increase the biological half-life of the peptide and so increase its availability for deposition.

The diagnostic assays of the present invention are carried out as exemplified in Example 14, below. In general, a commonly used protocol for an ELISA is followed. The Aβ peptide acts as the antigen of a conventional direct ELISA. The plates used are coated with zinc (II) or copper (II), hence, enabling the relatively stable binding of the Aβ peptide to the surface of the plate. Preferably, the zinc (II) or copper (II) is complexed to a ligand which is immobilized on the plate. Examples of such ligands include nitriloacetic acid and iminodiacetic acid. The complexes are prepared by dissolving the ligand in an organic solvent such as ether, depositing the solution on a solid support, letting the solvent evaporate, and then adding an equeous solution of a zinc (II) or copper (II) salt (such as the chloride). The solid support may then be washed with additional solution to remove unreacted ligand and metal salt. Preferred solid supports include but are not limited to nitrocellulose, diazocellulose, microtiter plates, glass, plastic, polystyrene, polyvinyl, polyvinylchloride, polypropylene, polyethylene, dextran, affinity support gels such as Sepharose or agar, starch, and nylon. Those skilled in the art will note that many other suitable carriers for binding the ligand exist, or will be able to ascertain the same by use of routine experimentation.

In a different embodiment of the diagnostic assays, the Aβ peptide in a solution can be detected by using solid support particles. The particles, beads or pieces of a solid support, are coated with zinc (II) or copper (II) form of nitriloacetic acid, thus, enabling the relatively stable binding of the Aβ peptide to the surface of the particle. The candidate solution is added to the particles and incubated as before-described to allow binding of the Aβ peptides to the surface(s) of the particles. Labelled antibodies, particularly radiolabelled ones, are used to bind to the Aβ peptides. Alternatively, antibodies specific for Aβ are added to bind to the Aβ peptides, and then labelled anti-antibodies, particularly radiolabelled ones, which are specific for the Aβ antibodies, are added to bind to the Aβ antibodies, thereby allowing detection and quantification of the Aβ peptides. The Aβ peptides are detected and/or quantified with the appropriate means, e.g., scintillation counter.

The bulk purification of Aβ from biological fluids is best achieved with copper charged chelating-Sepharose (Pharmacia, catalog no. 17-0575-01). The cysteine groups in the sample proteins are first methylated with N-methyl maleimide, about 1–20 mM, preferrably, about 10–20 mM, and most preferrably, about 10 mM for about 1–2 hours, preferrably about 1 hour, (other appropriate compounds, such as, iminodiacetic acid, may be used instead of maleimide in simillar concentrations and for simillar periods of time), then acidified by titrating pH to about 4.9–5.0, preferrably to about 5.0, using about 1–2 M, preferrably about lM, sodium acetate, pH about 3–4, preferrably about 3.5, and the total NaCl concentration increased by about 450–550 mM, preferrably by about 500 mM, with about 4–5 M, preferrably about SM NaCl. The sample is then applied to a copper-charged chelating-Sepharose column (e.g., 250 μl bed volume for about 15 ml of CSF) or free copper-charged chelating-Sepharose slurry (about 50–60 μl, preferrably about 50 μl of about 50% v/v) is added to the sample if the volume is less than about 4 ml. Equilibration buffer is about 450–550 mM, preferrably about 500 mM NaCl about 25–100 mM, preferrably about 50 mM MES, pH about 4.0–5.1, preferrably about 5.0 and is used to wash the column or the Sepharose pellet following centrifugation (preferably, low speed centrifugation (about 1,200–1,800 g, preferrably about 1,500 g, for about 2–4 minutes, preferrably about 3 minutes)). It should be noted that as the speed of centrifugation increases, the centrifugation time decreases. The Sepharose pellet is developed with SDS sample buffer containing 50 mM EDTA if the sample is to be applied in entirety to western blot analysis. Alternatively, the Sepharose can be developed with about 450–550 mM, preferrably about 500 mM NaCl, 50 mM EDTA, pH about 7.0–9.0, preferrably about 8.0, alone and the eluate sampled for western blot analysis. The treatment of 15 ml of CSF by this method enriched both soluble APP as well as 4.3 and 3.6 kDa species of Aβ (identified by an antibody that identifies an epitope in the first 16 residues of Aβ; commercially available). In order to bind copper or zinc, the peptide requires an intact domain from residues 6–28. 4G8 only recognized the two Aβ species and not APP, confirming that the APP captured by the Sepharose was post-secretase cleaved soluble APP. The use of specific anti-Aβ antibodies as described above on western blot analysis of these products can confirm the specificity of the ELISA immunoreactivity.

DEFINITIONS

Aβ peptide is also known in the art as Aβ, β protein, β-A4 and A4.

Amyloid as is commonly known in the art, and as is intended in the present specification, is a form of aggregated protein.

Similarly, Aβ Amyloid is an aggregated Aβ peptide. It is found in the brains of patients afflicted with AD and DS and may accumulate following head injuries and in Guamanian amyotrophic lateral sclerosis/Parkinson's dementia (GALS/PDC).

Tinctorial amyloid is referred to amyloid that in addition to being insoluble in aqueous buffer can be stained with Congo Red, and has positive birefringence in polarized light.

Anti-amyloidotic agent refers to a compound that inhibits formation of amyloid.

Zinc-induced Aβ aggregates are, like tinctorial amyloid, insoluble in aqueous buffer and stain with Congo Red.

Aβ amyloidosis, as is commonly known in the art and intended in the present specification, refers to the pathogenic condition in humans and other animals which is characterized by formation of Aβ amyloid in neural tissue such as brain.

Pre-filtering and pre-filtered as used in the present specification means passing a solution, e.g. Aβ peptide in aqueous solution, through a porous membrane by any method, e.g. centriftigation, drip-through by gravitational force, or by application of any form of pressure, such as gaseous pressure.

Physiological solution as used in the present specification means a saline solution which comprises compounds at physiological pH, about 7.4, which closely represents a bodily or biological fluid, such as CSF, blood, plasma, et cetera.

Heavy metal chelating agent refers to any agent, e.g., compound or molecule, which chelates heavy metals, i.e., binds the heavy metal very tightly and can inhibit or stop interaction with other agents. Examples of such heavy metal chealating agents are EDTA or Desferrioxamine.

In the present invention, the heavy metal salts are of any heavy metal or any transition metal, in any form, soluble or insoluble, e.g. the chloride, bromide, or iodide salts.

A blocker of heavy metal cations as used in the present invention refers to any compound that binds to all exposed metal binding sites remaining on the heavy metal cations, which are conjugated to the solid support, after Aβ capture. Examples of such blockers are, but are not limited to, gelatin (Biorad, catalog no. 170-6537) and SuperBlock (Pierce, catalog no. 375–35).

In the present specification, unless otherwise indicated, zinc means salts of zinc, i.e., $Zn^{2+}$ in any form, soluble or insoluble.

Biological fluid means fluid obtained from a person or animal which is produced by said person or animal. Examples of biological fluids include but are not limited to cerebrospinal fluid (CSF), blood, serum, urine, and plasma. In the present invention, biological fluid includes whole or any fraction of such fluids derived by purification by any means, e.g., by ultrafiltration or chromatography.

Neat sample of a biological fluid means that the biological fluid has not been altered by, for example, dilution.

Control human subject refers to a healthy person who is not afflicted with amyloidosis.

Synthetic peptide standard in the present invention means an assembly of amino acids linked by peptide bonds that is synthesized in a laboratory. Methods for making synthetic peptides include, although are not restricted to, such procedures as solid phase $P_{moc}$ chemistry.

A candidate solution in the present invention means a solution which is suspected of containing Aβ peptide.

An anti-antibody in the present invention means an antibody that binds specifically to another antibody. Generally such antibodies are obtained by immunizing an animal with the antibody from another animal. Thus, one can obtain goat anti-IgG polyclonal antibodies in this way.

A solid support in the present invention means any solid material to which the heavy metal cations can be complexed, and which can be used to make and use the invention. Examples of such solid support are, but not limited to, microtitre plates, petri dishes, bottles, slides, and other such containers made of plastic, glass, polyvinyl, polystyrene, and other solid materials which do not interfere with the formation of complexes and allow detection of labelled antibodies.

More specifically, solid support particles which may be used in the present invention are irregular shaped solid supports such as beads, particles, and pieces of the aforementioned solid materials which may be used for the practice of the present invention.

Persons skilled in the art are able to screen for and determine the usefulness of a solid support material by parallel testing and comparison between the material in question and a known solid support material such as polyvinyl or polystyrene.

In the present invention, the Aβ peptide may be comprised of any sequence of the Aβ peptide as long as it contains at least the amino acids corresponding to positions 6 through 28 of Aβ peptide which comprise the binding site for zinc, the most preferred heavy metal cation capable of binding to a polypeptide comprising at least amino acids 6 to 28 of Aβ. The preferred embodiments of the invention make use of peptides $A\beta_{1-39}$, $A\beta_{1-40}$, $A\beta_{1-41}$, $A\beta_{1-42}$, and $A\beta_{1-43}$. The most preferred embodiment of the invention makes use of $A\beta_{1-40}$. However, any of the Aβ peptides which comprises at least amino acids 6 to 28 of Aβ may be employed according to the present invention. The sequence of Aβ peptide, including amino acids 6 to 28, is found in FIG. 10 (C. Hilbich et al., *J. Mol. Biol.* 228:460–473 (1992)).

In the present method, the Aβ peptide is directly detected by using optical spectrophotometry. This is possible because a direct correlation exists between concentration of the peptide and $OD_{214}$ measurements. Although the preferred wave length for the OD measurements is about 214 nm, the measurements may be carried out for the purpose of the present invention at wave lengths from about 190 to about 500 nm. Preferred wave lengths are, however, from about 208 to about 280 nm.

Further, the Aβ peptide may be detected by radiolabelling the peptide and measuring the compounds per minute (CPM) of the filtrates and/or the pellets. A preferred radiolabelled Aβ peptide in the present invention is $^{3}$H-Aβ. Other radiolabels which can be used in the present invention are $^{14}$C and $^{35}$S.

The labelled antibodies and anti-antibodies are detected by using visible-light microwell plate reader (for chromogenic enzymes), fluorescence microwell plate reader (for fluorescence-generating enzymes), and scintillation counter (for radioisotopes). The types of labels and the appropriate means for detection of the labels, however, are not limited to those specifically mentioned herein.

Other heavy metal cations capable of binding to a polypeptide comprising at least amino acids 6 to 28 of Aβ which may be used in the practice of the invention include metallochloride salts, preferably of zinc, copper, or mercury. The most preferred embodiment of the invention, however, makes use of zinc chloride.

In the preferred embodiments of the invention, the antibodies specific to Aβ protein are labelled with a radioisotope (radioactive isotope), which can then be determined by such means as the use of a gamma counter or a scintillation counter. Isotopes which are particularly useful for the purpose of the present invention are: $^{3}$H, $^{125}$I, $^{131}$I, $^{32}$P, $^{35}$S, $^{14}$C, $^{51}$Cr, $^{36}$Cl, $^{57}$Co, $^{58}$Co, $^{59}$Fe and $^{75}$Se.

Another way in which the antibody of the present invention can be detectably labeled is by linking or conjugating the same to an enzyme. This enzyme, in turn, when later exposed to its substrate, will react with the substrate in such a manner as to produce a chemical moiety which can be detected as, for example, by spectrophotometric, fluorometric or visual means. Examples of enzymes which can be used to detectably label the antibody of the present invention include malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase. Avidin-biotin binding may be used to facilitate the enzyme labeling.

It is also possible to label the antibody with a fluorescent compound. When the fluorescently labeled antibody is exposed to light of the proper wave length, its presence can then be detected due to the fluorescence of the dye. Among the most commonly used fluorescent labelling compounds are fluorescein isothiocyanate, rhodamine, phycoerytherin, phycocyanin, allophycocyanin, o-phthaldehyde and fluorescamine.

The antibody of the invention can also be detectably labeled using fluorescent emitting metals such as $^{152}$Eu, or others of the lanthanide series. These metals can be attached to the antibody molecule using such metal chelating groups as diethylenetriaminepentaacetic acid (DTPA) or ethylenediaminetetraacetic acid (EDTA).

The antibody of the present invention also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent antibody is determined by detecting the presence of luminescence. Important bioluminescent compounds for purposes of labeling are luciferin, luciferase and aequorin.

Another technique which may also result in greater sensitivity when used in conjunction with the present invention consists of coupling the antibody of the present invention to low molecular weight haptens. The haptens can then be specifically detected by means of a second reaction. For example, it is common to use such haptens as biotin (reacting with avidin) or dinitrophenyl, pyridoxal and fluorescamine (reacting with specific anti-hapten antibodies) in this manner.

In addition, the sensitivity of the assay may be increased by use of amplification strategies including substrate cycling and enzyme channeling as taught by Mosbach (Lindbladh et al., *Trends in Biochem. Sci.* 18:279–283 (1993).

The pH of the reaction mixtures for Aβ capture to immobilized metal ions is, unless otherwise indicated, preferably close to neutral (about 7.4). The pH, therefore, may range from about 6.8 to about 8.5, preferably from about 7 to about 7.8, and most preferably about 7.4. The pH of other incubations, including antibody and anti-antibody incubations is between 7–9, preferably at 8.

Buffers which can be used in the methods of the present invention include, but are not limited to, Tris-chloride and Tris-base, MOPS, HEPES, bicarbonate, Krebs, and Tyrode's. The concentration of the buffers may be between about 10 mM and about 500 mM. However, considering that these buffers chelate zinc, the concentration of the buffers should be kept as low as possible without compromising the results.

The present invention permits use of very low concentrations of Aβ peptide, e.g. from about 0.1 nM to 3.7 mM (upper limit of solubility). A preferred embodiment of the invention employs about 0.8 nM concentration of Aβ peptide, the lowest detectable concentration of Aβ previously reported for an ELISA type assay was 0.5 nM (Schubert et al., *Nature* 359:325–327 (1992)).

The present invention may be practiced at temperatures ranging from about 1 degree centigrade to about 99 degrees centigrade. The preferred temperature range is from about 4 degrees centigrade to about 40 degrees centigrade. The most preferred temperature for the practice of the present invention is about 37 degrees centigrade. Therefore, an advantage of the present invention is the greatest sensitivity over previous detection systems.

The Aβ peptide is trapped by the free coordination sites on the zinc or copper atoms (binds to the zinc or copper atoms) at near-instantaneous rate. However, defusion rates are a limiting factor in the absorption of the peptide and antibodies to the solid phase. In a preferred embodiment of the invention, the incubations are carried out for about 90–240, preferably about 120, minutes to maximize capture.

Figure 1A:
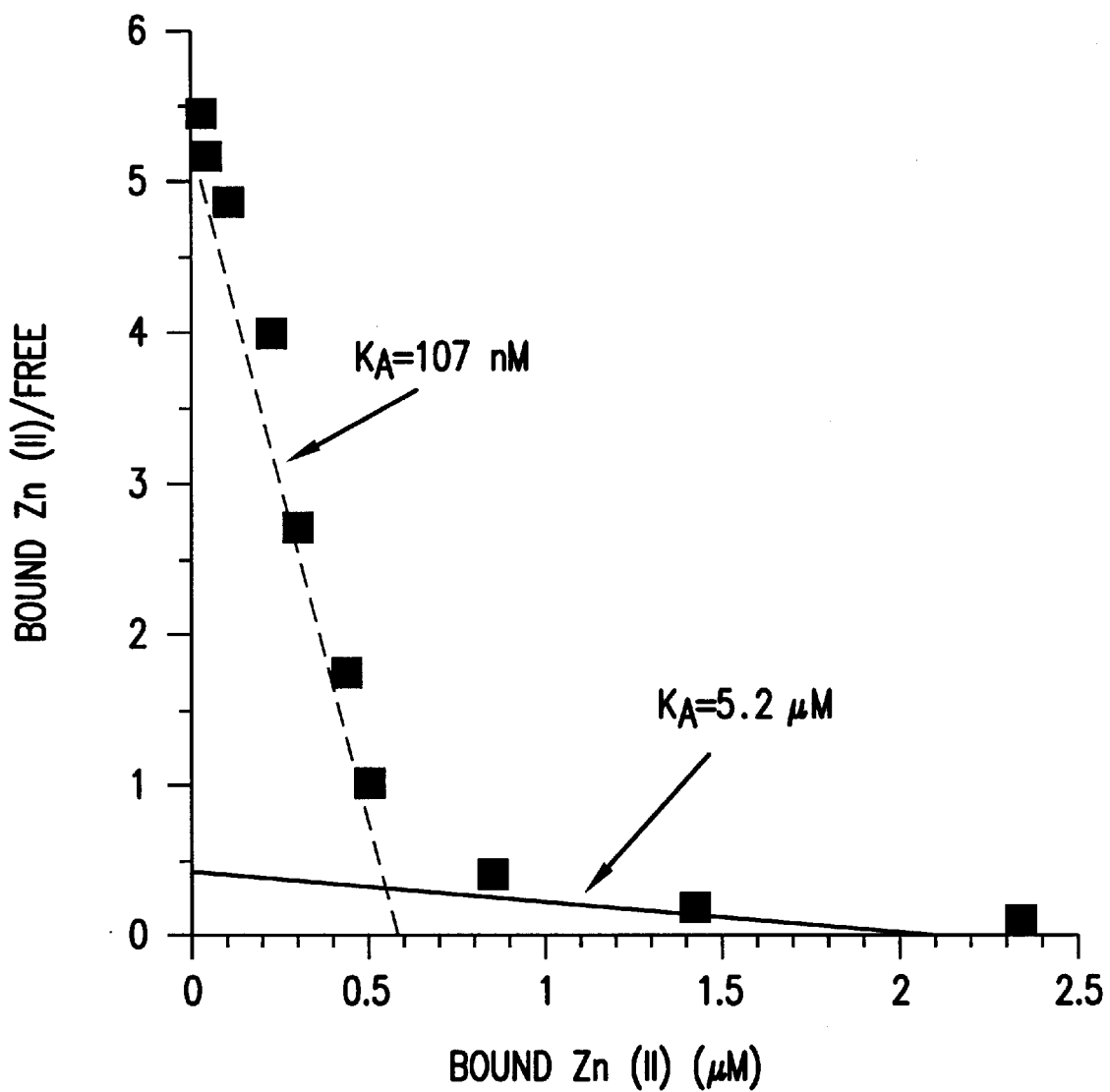
FIGS. 1a, 1b, 1c, 1d and 1e depict graphs showing analyses of $^{65}Zn^{2+}$ binding to Aβ. Values shown are means±S.D., n≧3. (1a) Scatchard plot. Aliquots of Aβ were incubated (60 min) with $^{65}Zn^{2+}$ in the presence of varying concentrations of unlabeled $Zn^{2+}$ (0.01–50 μM total). The proportion of $^{65}Zn^{2+}$ binding to immobilized peptide (1.0 nmol) described two binding curves as shown. The high-affinity binding curve has been corrected by subtracting the low-affinity component, and the low-affinity curve has had the high-affinity component subtracted. (1b) Bar graph showing the specificity of the $Zn^{2+}$ binding site for metals. Aβ was incubated (60 min) with $^{65}Zn^{2+}$ (157 nM, 138,000 cpm) and competing unlabeled metal ions (50 μM total). (1c) Bar graph showing $^{65}Zn^{2+}$ (74 nM, 104,000 cpm) binding to negative (aprotinin, insulin a-chain, reverse peptide 40-1) and positive (bovine serum albumin (BSA)) control proteins and Aβ fragments (identified by their residue numbers within the Aβ sequence, gln11 refers to $Aβ_{1-28}$ where residue 11 is glutamine). Percent binding of total counts $^{65}Zn^{2+}$/min added is corrected for the amounts (in nanomoles) of peptides adhering to the membrane. (1d) Scatchard plot. Aβ for (1a), with $Aβ_{1-28}$ peptide substituting for $Aβ_{1-40}$. 157 nM $^{65}Zn$ (138,000 cpm) is used in this experiment to probe immobilized peptide (1.6 nmol). (1e) Graph showing the pH dependence of $^{65}Zn^{2+}$ binding to $Aβ_{1-40}$.

To determine whether Aβ binds zinc, a synthetic peptide representing secreted Aβ$_{1-40}$ was incubated with $^{65}$Zn$^{2+}$. Rapid binding (60% B$_{max}$ at 1 min), which plateaued at 1 h, was observed. Scatchard analysis of $^{65}$Zn$^{2+}$ binding describes two saturable binding curves, a high affinity curve ($K_a$<107 nM), and a lower affinity curve ($K_a$<5.2 μM) (FIG. 1a). The affinity constant estimates might be skewed by assuming that the Tris buffer does not bind zinc. In fact, Tris-HCl binds zinc and copper with stability constants of 4.0 and 2.6, respectively (Dawson et al., *Data for Biochemical Research*, Oxford University Press (1986)). Incubating Aβ in the presence of higher concentrations of Tris (150 and 500 mM) abolishes $^{65}$Zn$^{2+}$ binding to Aβ (≈50% and ≈95%, respectively), indicating that Tris-induced Zn$^{2+}$ chelation cannot be excluded. Our calculated affinity constants are therefore upper limit estimates.

Figure 1B:
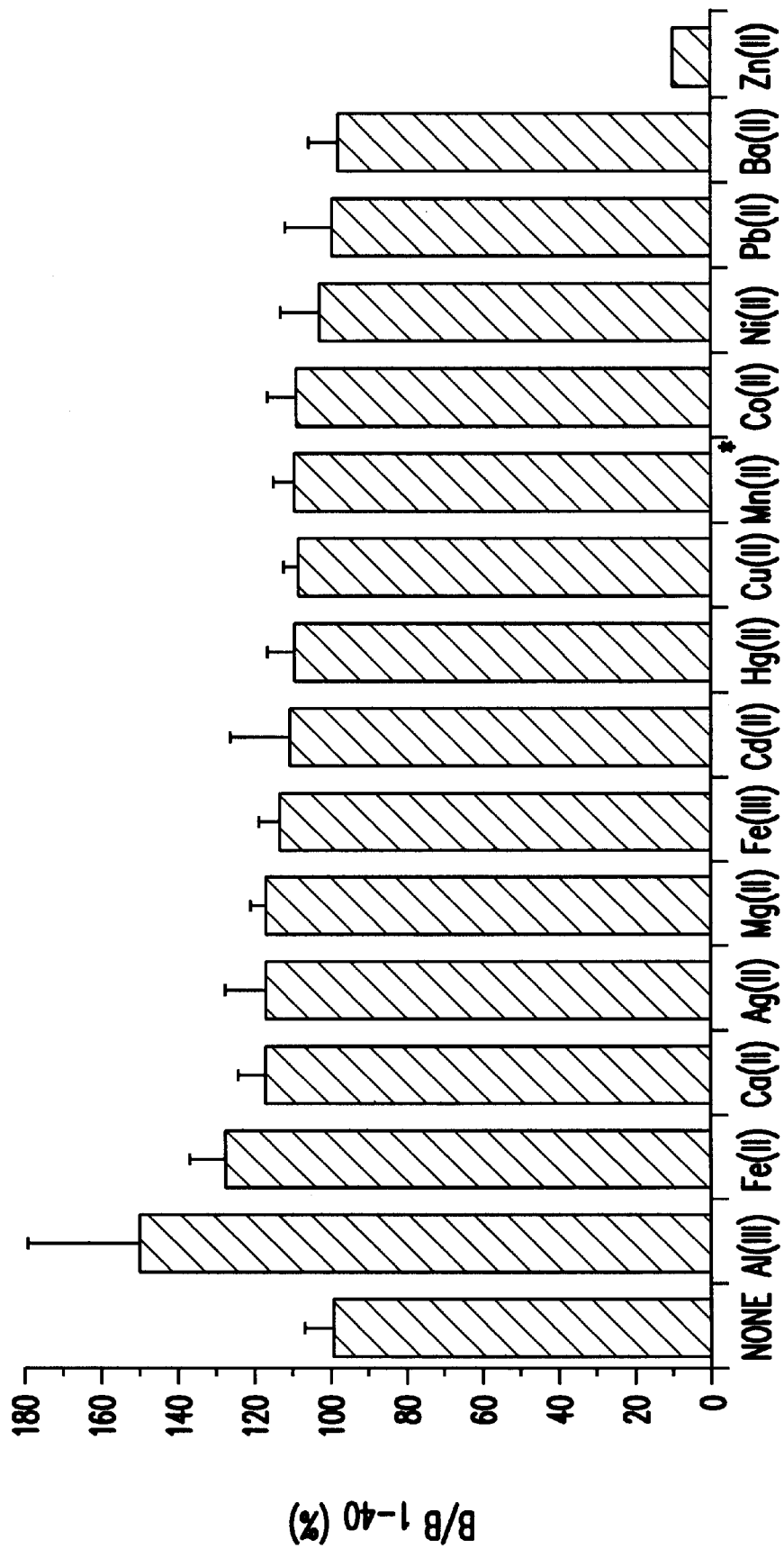
Figure 1C:
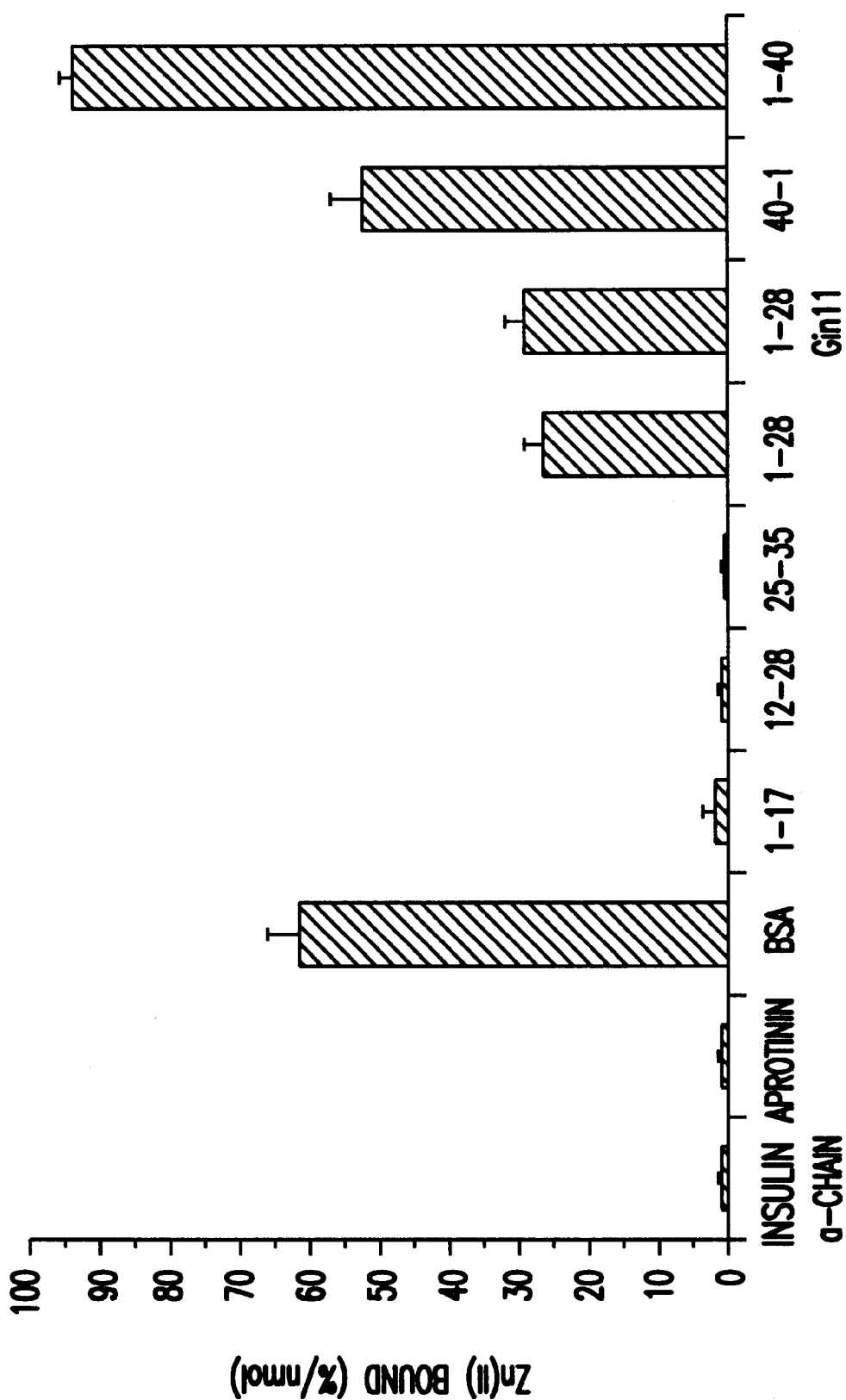
Figure 1D:
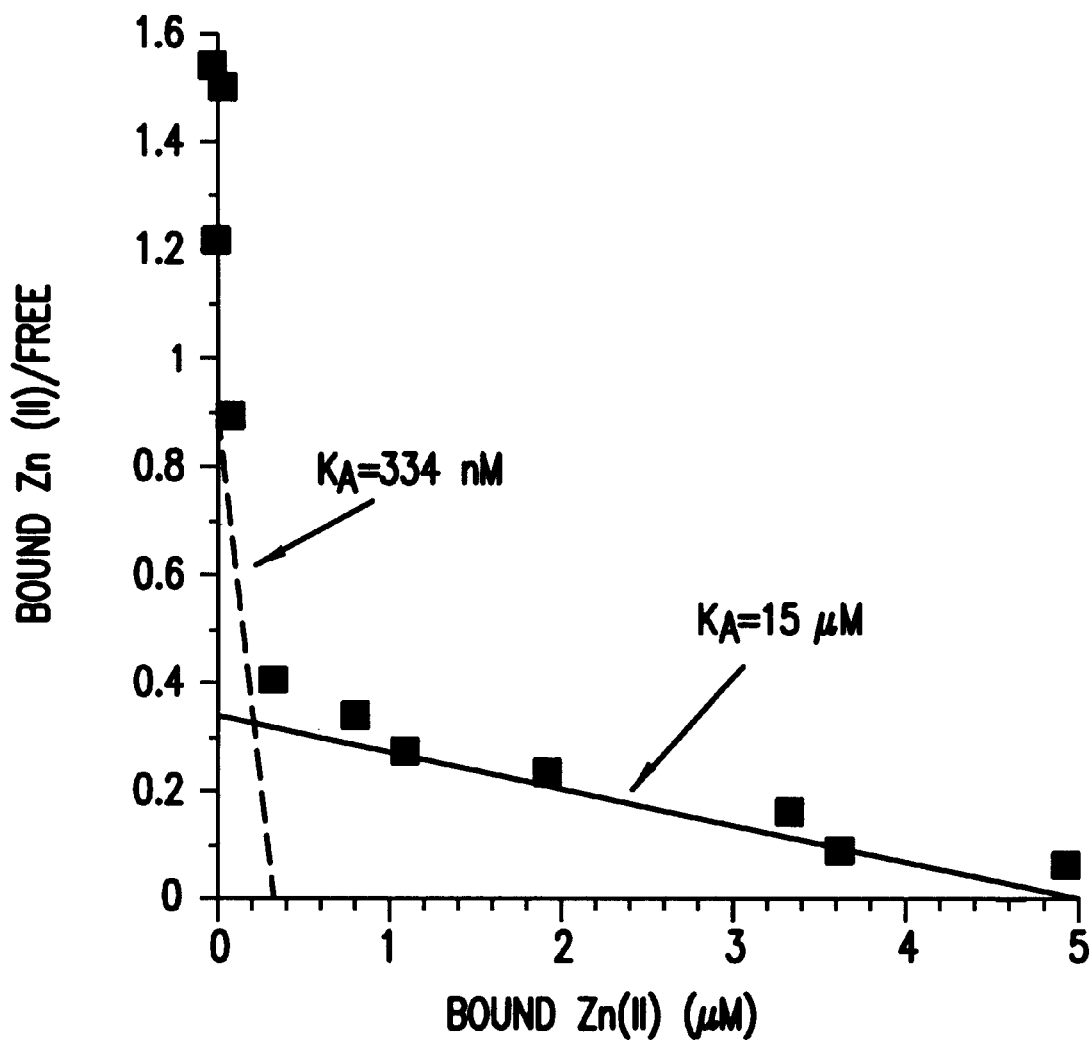
Figure 1E:
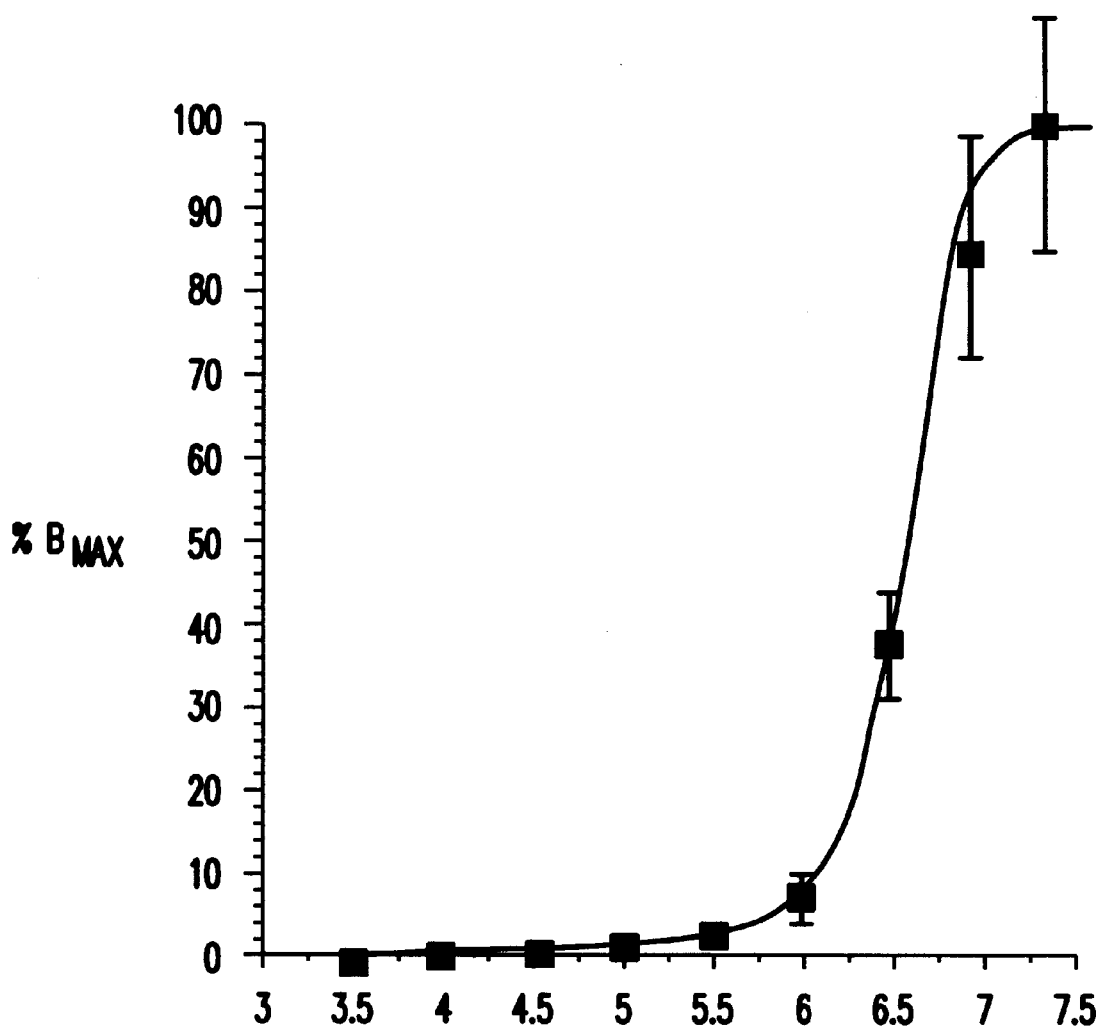

$^{65}$Zn$^{2+}$ binding is very specific, with Zn$^{2+}$ being the only unlabeled metal ion tested that is capable of competing off the label (FIG. 1b). To determine the specific region of Aβ involved in zinc binding and to validate the dot-blot binding system, equivalent amounts of various peptides representing fragments of Aβ$_{1-40}$ and peptide controls were assayed for $^{65}$Zn$^{2+}$ binding in this system (FIGS. 1c and 1d).

The reverse sequence (40-1) control peptide only binds 50% of B$_{max}$ compared with Aβ$_{1-40}$ (FIG. 1c), indicating that zinc binding is not merely a consequence of the presence of favorable residues. Aβ$_{1-28}$ bound 30% of B$_{max}$, indicating that the carboxyl terminus plays an important role in promoting zinc binding. Glutamine substitution for the glutamate at position 11 of Aβ$_{1-28}$, in accordance with the Down's syndrome Aβ sequence reported by Glenner and Wong, *Biochem. Biophys. Res. Commun.* 120:885–890 (1984), does not interfere with $^{65}$Zn$^{2+}$ binding. The Scatchard plot of $^{65}$Zn$^{2+}$ binding to Aβ$_{1-28}$ reveals similar low-affinity ($K_a$<15 μM) and high-affinity ($K_a$<334 nM) binding associations (FIG. 1d) to those of Aβ$_{1-40}$, but overall the Aβ$_{1-28}$ peptide binds zinc less avidly. Although the Aβ$_{1-28}$ peptide clearly binds zinc, peptides overlapping this region (1-17 and 12-28) do not individually bind zinc. Additionally, a peptide covering a region of the carboxyl terminus (25–35) also is unable to bind zinc (FIG. 1c).

The calculated stoichiometry of high-affinity Zn$^{2+}$-binding to Aβ, derived from the x-intercepts on the Scatchard plots (FIG. 1, a and d), is 0.7:1 (Aβ$_{1-40}$) and 1:4 (Aβ$_{1-28}$). For low-affinity binding, the Zn$^{2+}$:Aβ ratio is 2.5:1 (Aβ$_{1-40}$) and 4:1 (Aβ$_{1-28}$).

$^{65}$Zn$^{2+}$ binding of sequenced tryptic digest products of Aβ (FIG. 4b) indicates that the 6-40 fragment binds zinc, but that the other visible digest fragment 17-40 (FIG. 4b), equivalent to the post-secretase (Esch et al., *Science* 248:1122–1124 (1990); Sisodia et al., *Science* 248:492–495 (1990)) carboxyl-terminal product produced in vivo, does not bind zinc. The contribution of histidines (residues 6, 13, and 14) to Zn$^{2+}$ binding is indicated by the deterioration of binding with lower pH (30% of $B_{max}$ at pH 6.0, FIG. 1e). Taken together, these data indicate that zinc coordination requires the contiguous sequence between residues 6 and 28, a region containing all 3 histidine residues, and that optimal zinc binding also requires the presence of the carboxyl-terminal domain.

Figure 2A:
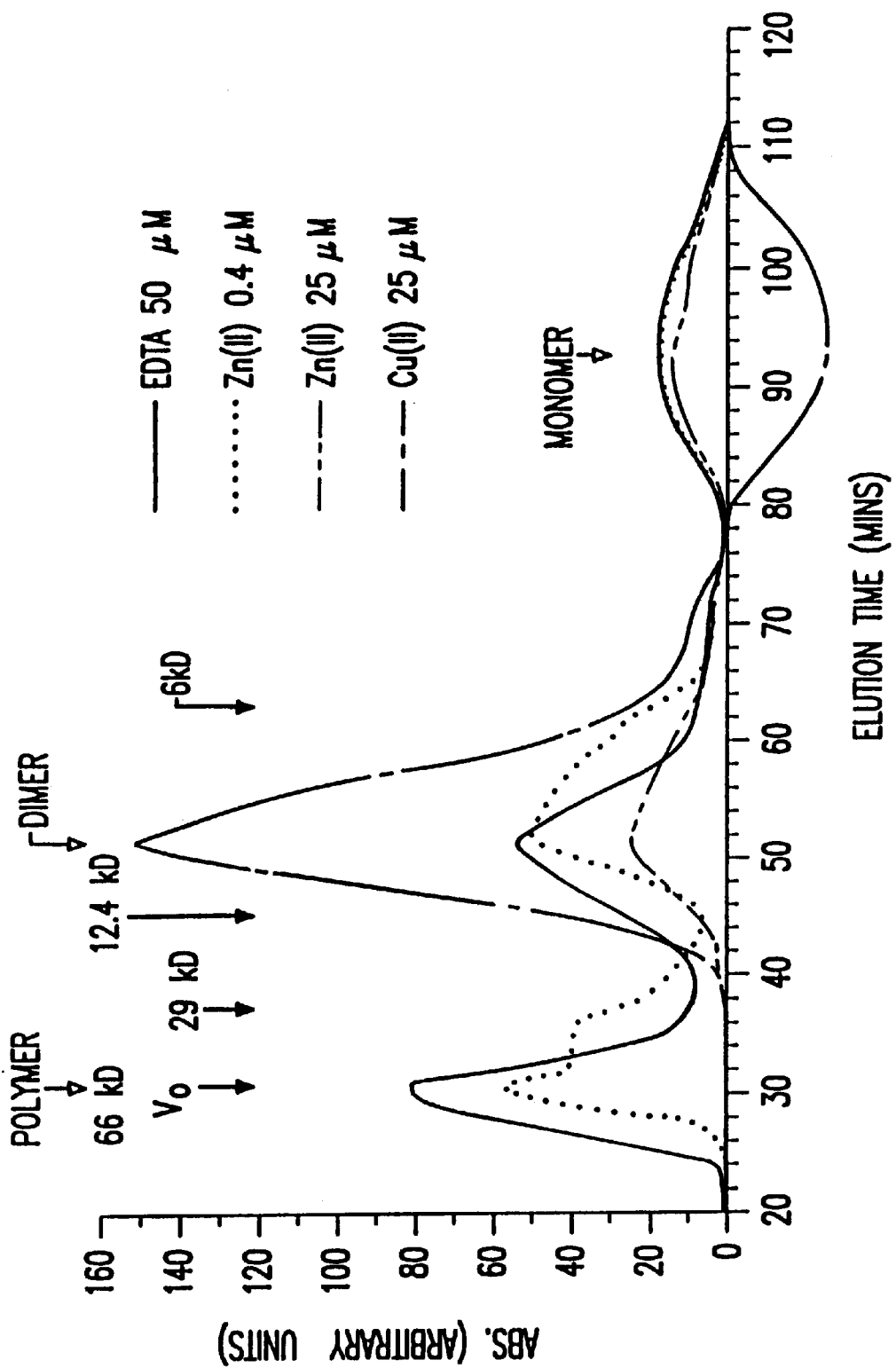
FIGS. 2a, 2b and 2c depict graphs showing effect of $Zn^{2+}$ and other metals on Aβ polymerization using G50 gel filtration chromatography. Results shown are indicative of n≧3 experiments where 55 μg of Aβ is applied to the column and eluted in 15 ml, monitored by 254 nm absorbance. (2a) A graph showing the chromatogram of Aβ in the presence of EDTA, 50 μM; $Zn^{2+}$, 0.4 μM; $Zn^{2+}$, 25 μM; and $Cu^{2+}$, 25 μM. The elution points of molecular mass standards and relative assignments of Aβ peak elutions are indicated. Mass standards were blue dextran (2×10$^6$ daltons, $V_0$=void volume), BSA (66 kDa), carbonic anhydrase (29 kDa), cytochrome c (12.4 kDa), and aprotinin (6.5 kDa). The mass of Aβ is 4.3 kDa. (2b) Bar graph showing the relative amounts (estimated from areas under the curve) of soluble Aβ eluted as monomer, dimer, or polymer in the presence of various metal ions (25 μM), varying concentrations of $Zn^{2+}$ or $Cu^{2+}$ (the likelihood of Tris chelation is indicated by upper limit estimates), and EDTA. Data for experiments performed in the presence of copper were taken from 214 nm readings and corrected for comparison. (2c) Bar graph showing the effects of pre-blocking the chromatography column with BSA upon the recovery of Aβ species in the presence of zinc (25 μM), copper (25 μM), or chelator.
Figure 2B:
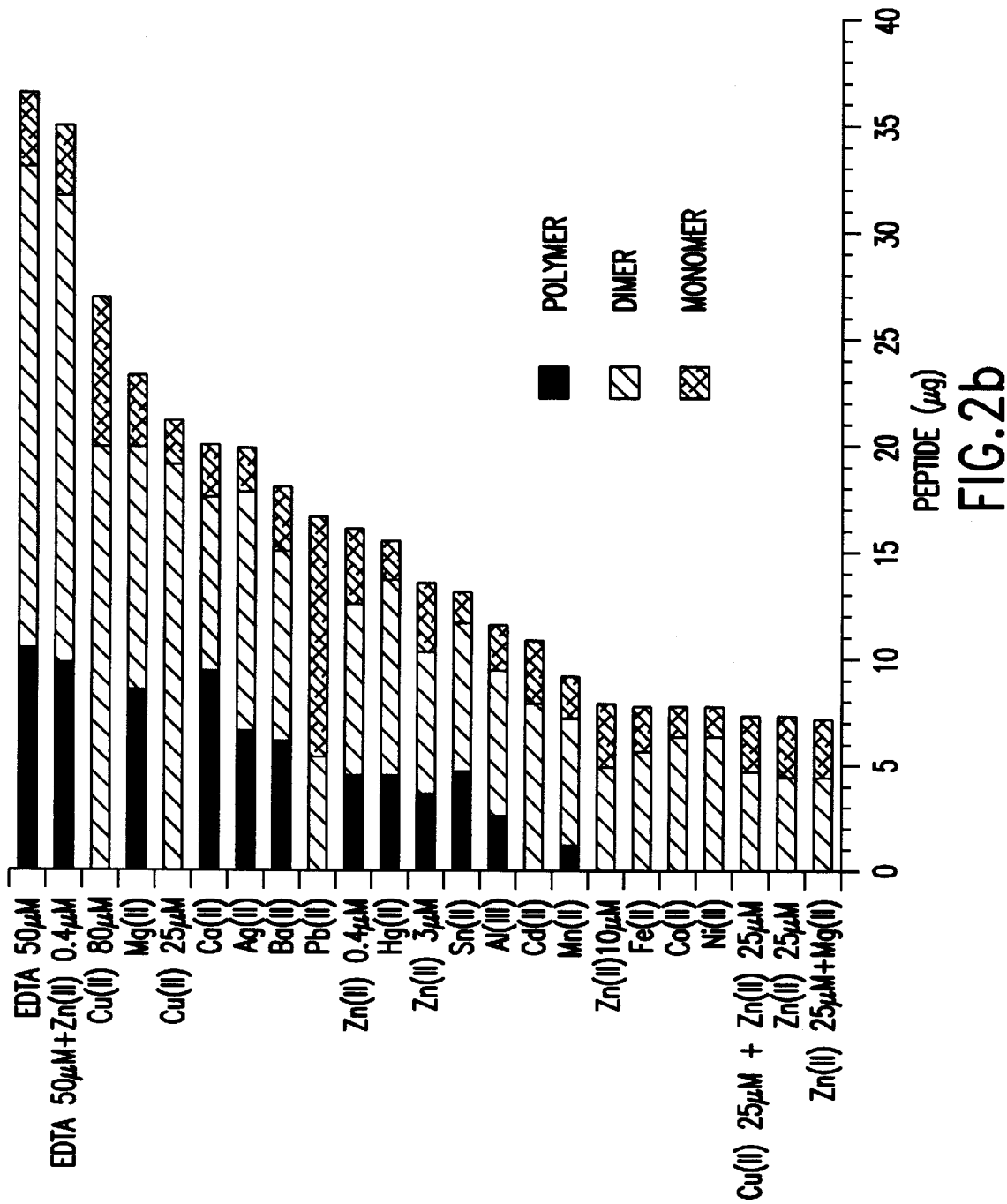

Further experiment investigated whether zinc binding could affect Aβ conformation as assayed by migration on gel-filtration chromatography. Major Aβ species believed to correspond to monomeric, dimeric, and polymeric forms were observed (FIG. 2a). Total concentrations of $Zn^{2+}$ as low as 0.4 μM decrease recovery of Aβ compared with elution profiles obtained in the presence of EDTA and other metals (FIGS. 2a and 2b). At 25 μM total $Zn^{2+}$, <20% of the Aβ applied to the column is eluted. The greatest loss occurred among high order polymer and dimeric species. The relative amount of monomeric Aβ is less affected. A systematic assessment of several metals indicates that the reduction of Aβ recoverable by chromatography is most sensitive to $Zn^{2+}$, with related transition metals $Co^{2+}$, $Ni^{2+}$, and $Fe^{2+}$ (at 25 μM) displaying similar effects on chromatography to those obtained with only 10 μM $Zn^{2+}$ (FIG. 2b). Other transition metals, heavy metals, and $Al^{3+}$ (25 μM) have partial effects on Aβ solubility comparable with 3 μM total $Zn^{2+}$. Meanwhile, $Ba^{2+}$, $Ag^{2+}$, $Mg^{2+}$, and $Ca^{2+}$ (25 μM) have the least effect on Aβ compared with the EDTA profile, although a 60% reduction in eluted peptide was observed in the presence of these metal ions. $Pb^{2+}$ (25 μM) most strongly promotes the elution of the monomeric peptide, abolishing high order polymers; overall recovery is similar to that obtained with 0.4 μM total $Zn^{2+}$. In making comparisons of the effects of these metal ions, it is again important to consider the differential metal ion chelating effects of Tris previously mentioned.

A dramatic increase in Aβ dimerization is observed with Cu2+ (25 μM total). This metal also induces exaggerated Aβ absorbance (4-fold) at 254 nm when compared with 214 nm absorbance and induces the monomeric species to apparently fluoresce at 254 nm causing negative readings (FIG. 2a) which are proportionally positive at 214 nm (FIG. 2b). A higher concentration of $Cu^{2+}$ (80 μM total) promotes increased recovery of Aβ, indicating that the presence of $Cu^{2+}$ at relatively low concentrations (less than 25 μM) favors solubility in this system.

The metal ions which most favored Aβ solubility ($Mg^{2+}$, 25 μM and total $Cu^{2+}$, 25 μM) were tested for their ability to stabilize Aβ in a soluble state in the presence of 25 μM total $Zn^{2+}$. These combinations neither rescue nor worsen $Zn^{2+}$-induced loss of Aβ recovery (FIG. 2b). Overall, these data suggest that $Zn^{2+}$ reduces the recovery of Aβ, whereas a chelating agent attenuates this effect.

Figure 2C:
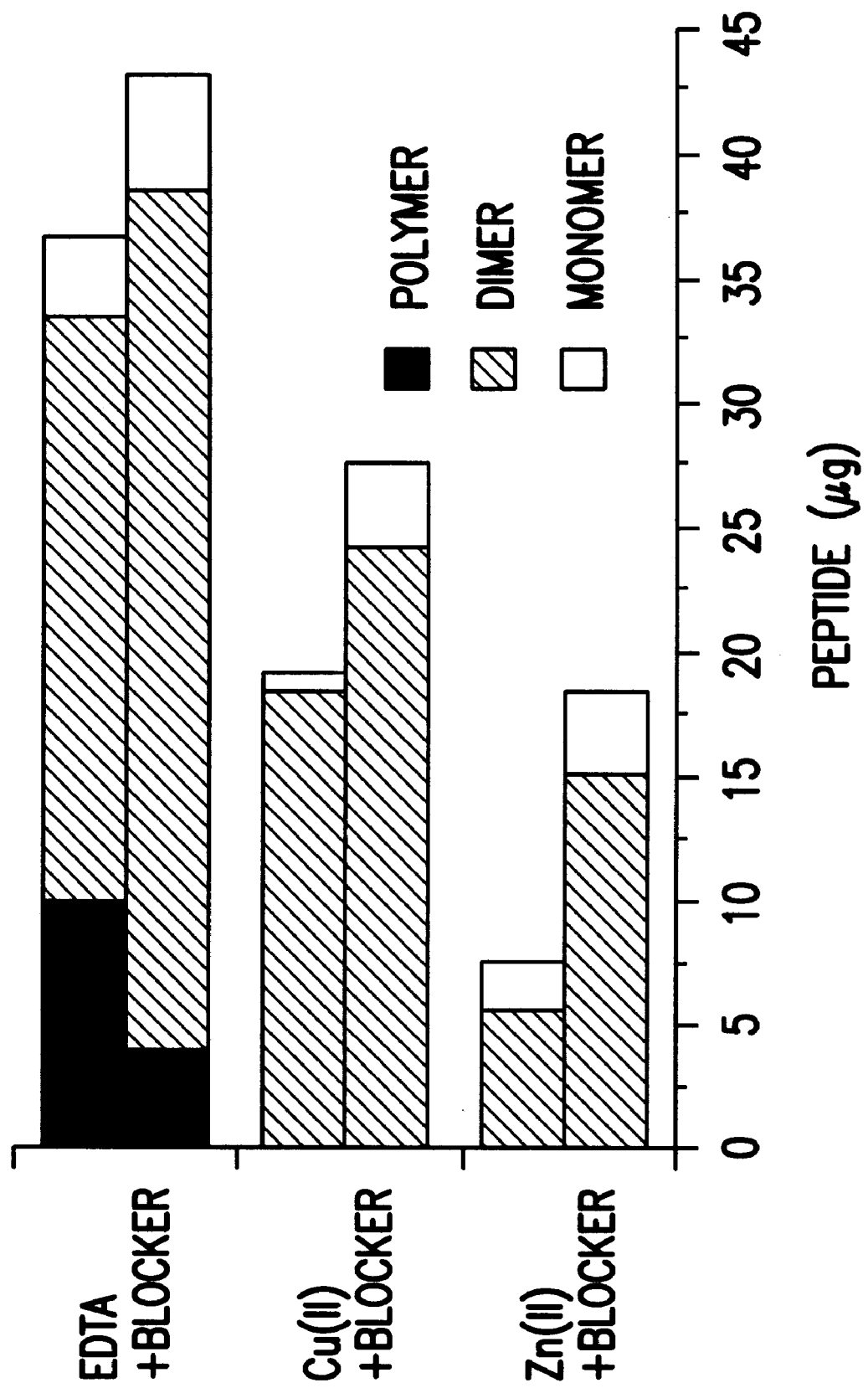

Chromatography of Aβ was performed under various conditions to determine if zinc-induced loss of Aβ could be blocked. Pretreating the column with 3% BSA as an adsorption blocker significantly increased the amounts of Aβ recovered from the column, and suggest that on untreated apparatus the peptide precipitates onto a column component (FIG. 2c). Blocking the column results in a 200% increase in the recovery of Aβ in the presence of $Zn^{2+}$ (25 μM total), a 75% increase in recovery in the presence of $Cu^{2+}$ (25 μM total), but only a 10% increase in the presence of EDTA (50 μM). This indicates that precipitation onto the column is most specifically accelerated by zinc.

To determine the part of the column onto which Aβ was precipitating, Aβ solutions were incubated with various column components and assayed by UV absorption before and after incubation. Replicating the chromatography experimental conditions, Aβ (100 μM in equilibration buffer) was incubated for 1 h in plastic reaction vessels with or without the presence of Sephadex. Loss to the plastic accounts for<5% of the observed precipitation, to siliconized plastic<1%, and binding to Sephadex<1%. Hence, Aβ precipitates are unlikely to be adsorbing to the Sephadex or plastic support. However, similar incubations in borosilicate glass test tubes result in 20% adsorption, which increase to 35% in the presence of zinc (25 JM).

Figure 3A:
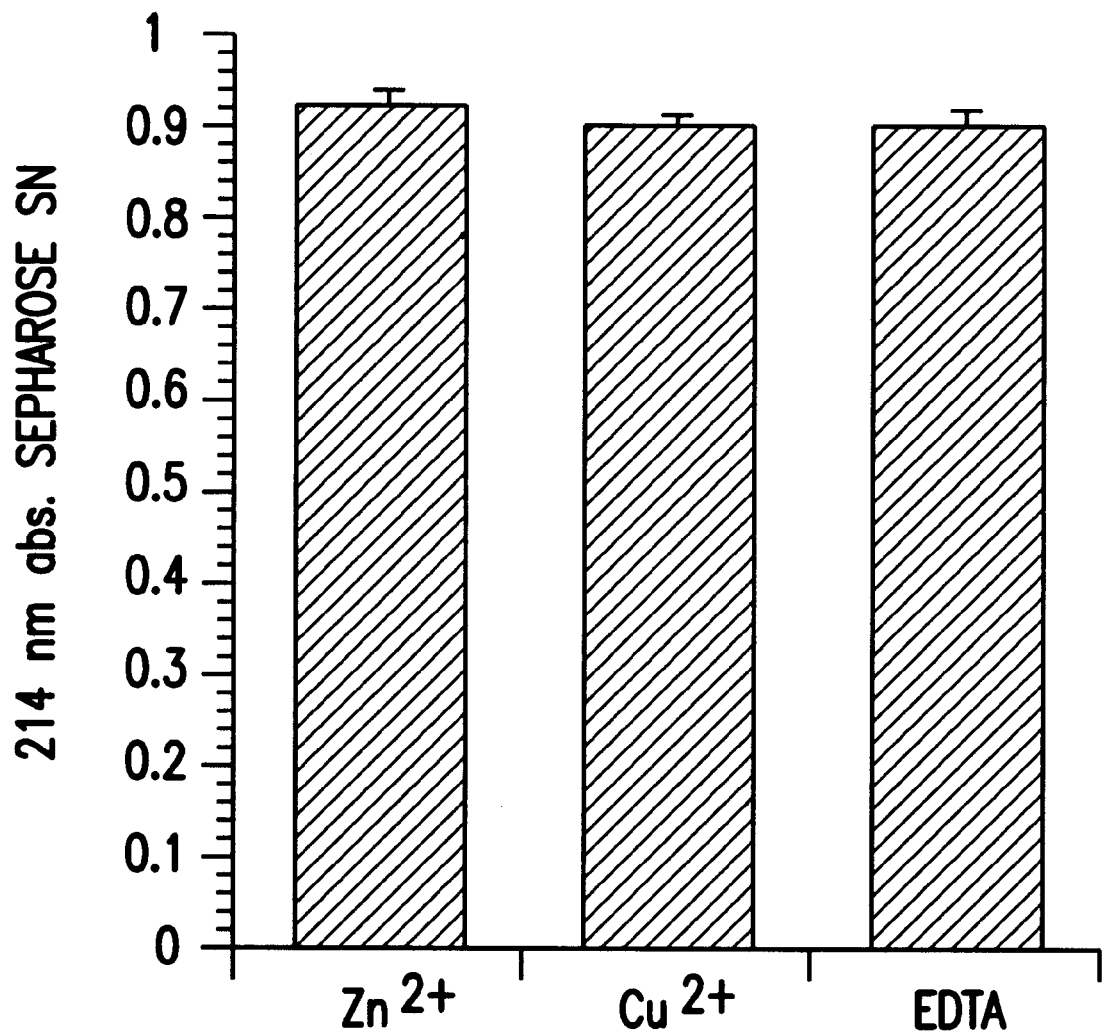
FIGS. 3a and 3b depict bar graphs showing Aβ binding to kaolin (aluminum silicate): effects of zinc (25 μM), copper (25 μM), and EDTA (50 μM). (3a) Bar graph showing the concentration (by 214 nm absorbance) of Aβ remaining in supernatant after incubation with 10 mg of G50 Sephadex. (3b) Bar graph showing the concentration (by 214 nm absorbance) of Aβ remaining in supernatant after incubation with 10 mg of kaolin, expressed as percent of the starting absorbance.
Figure 3B:
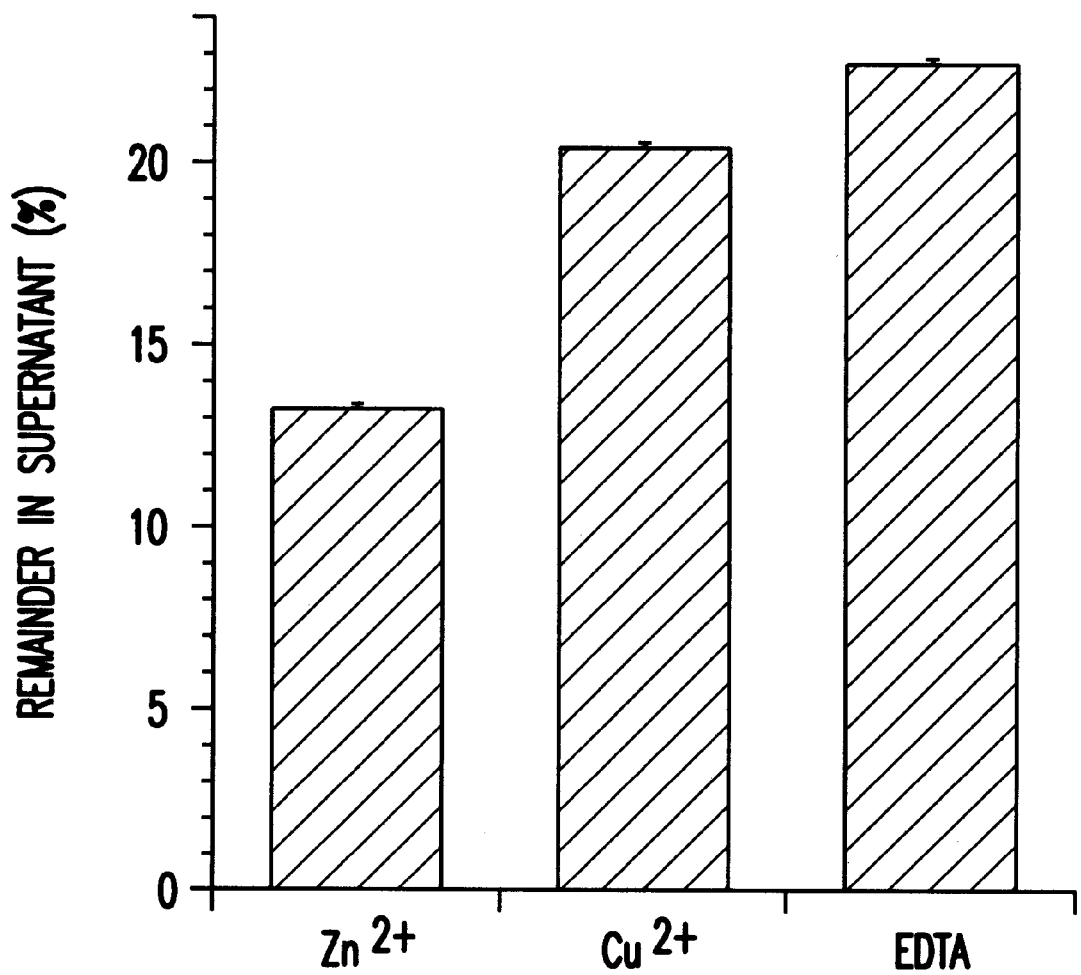

The glass in the Bio-Rad Econo Columns is made of 7740 Pyrex (Corning, Park Ridge, Ill.) and is composed of $SiO_2$, 80.6%; $B_2O_3$, 13.0%; $Na_2O$, 4.0%; and $Al_2O_3$, 2.3%. Previous workers have found evidence linking aluminosilicates with β-amyloid deposition (Masters et al., *EMBO J.* 4:2757–2763 (1985a); Candy et al., *Lancet* 1:354–357 (1986)). In light of these reports, experiments were performed to further investigate the phenomena which were observed for precipitation of Aβ on 7740 Pyrex glass. Rapid and extensive binding of Aβ to kaolin, an insoluble hydrated aluminum silicate was observed. Moreover, incubation of Ai (0.4 mg/ml) with Sephadex (5%, v/v) in the presence of zinc, copper, or EDTA causes only small changes in solubility, some of which is probably due to binding of the peptide to the plastic reaction vessels (FIG. 3a). Incubation of Aβ (0.4 mg/ml) with kaolin (5%, v/v, 5 min, room temperature), causes precipitation of up to 87% of the peptide present. This precipitation is greatest in the presence of zinc (25 μM) where the amount of Aβ recovered from the zinc incubation supernatant is nearly half of the amount recovered from the EDTA incubation supernatant (FIG. 3b). The effect of copper (25 μM) upon kaolin-induced Aβ precipitation is similar to the effect of EDTA (FIG. 3b). The binding of Aβ to kaolin is not reversible to subsequent treatment with 10 mM EDTA, but can be eluted by 2 M NaOH.

To further test whether zinc induces irreversible precipitation of Aβ in the absence of kaolin, Aβ incubated with $Zn^{2+}$ (200 μM, 1-24 h, 20° C.) was subjected to SDS Tris/Tricine gel electrophoresis. The monomeric species was the major band detected on Coomassie-stained gels and migrated identically to unincubated Aβ, indicating that zinc does not induce covalent or SDS-resistant polymerization of Aβ.

Figure 4A:
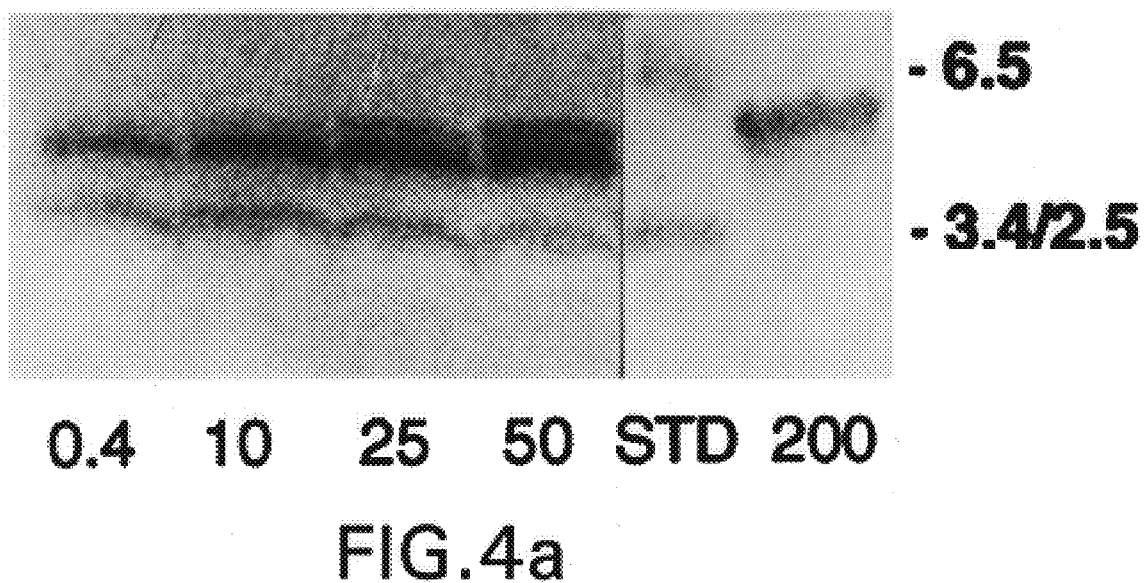
FIGS. 4a and 4b depict a blot and a bar graph showing the effect of $Zn^{2+}$ upon Aβ resistance to tryptic digestion. (4a) A blot of tryptic digests of Aβ (13.9 μg) after incubation with increasing concentrations of zinc (lane labels, in micromolar), stained by Coomassie Blue. Digestion products of 3.6 kDa ($Aβ_{6-40}$), and 2.1 kDa ($Aβ_{17-40}$), as well as undigested $Aβ_{1-40}$ (4.3 kDa), are indicated on the left. The migration of the low molecular size markers (STD) are indicated (in kilodaltons) on the right. (4b) A bar graph showing $^{65}Zn^{2+}$ binding to Aβ tryptic digestion products. The blot was incubated with $^{65}Zn^{2+}$, the visible bands excised, and the bound counts for each band determined. These data are typical of n=3 replicated experiments.
Figure 4B:
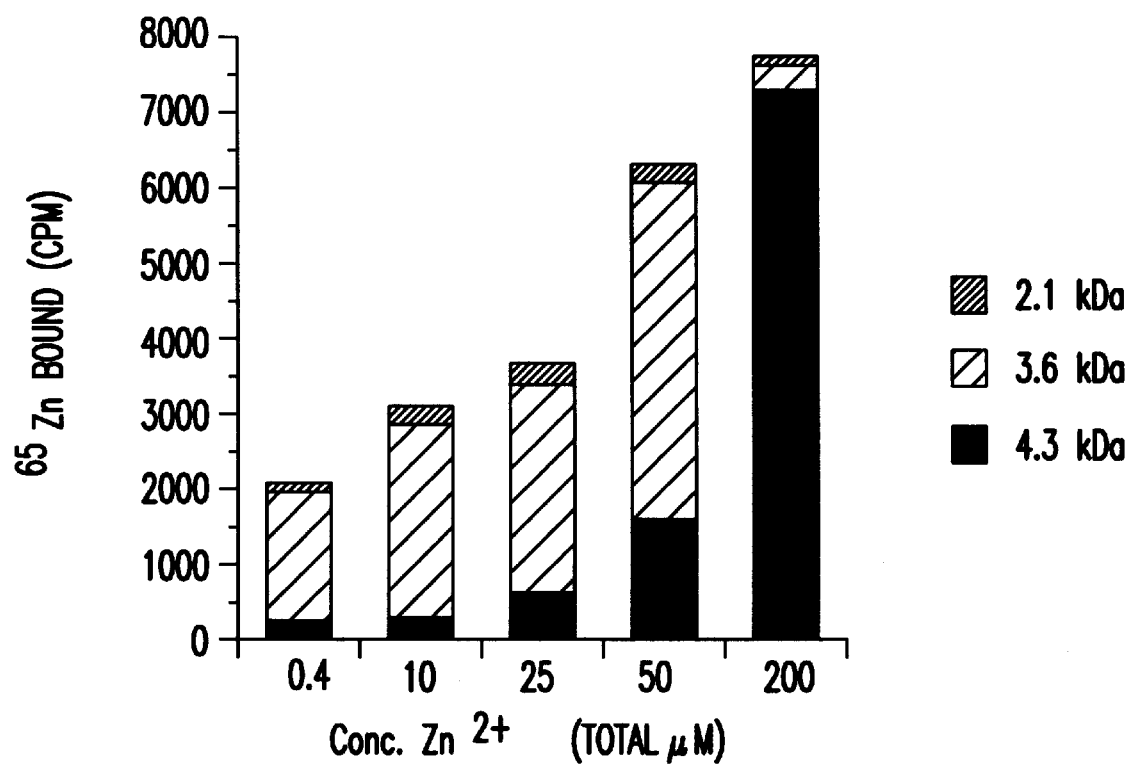

The APPα-secretase site at Lys-16 (Esch et al., *Science* 248:1122–1124 (1990); Sisodia et al., *Science* 248:492–495 (1990)) in Aβ is within the obligatory zinc binding region. The ability of $Zn^{2+}$ to protect Aβ from secretase-type cleavage was investigated using the serine-protease trypsin, whose activity is unaffected by zinc. Amino-terminal sequence on Aβ tryptic digestion products transferred to polyvinylidene difluoride membrane following SDS-polyacrylamide gel electrophoresis indicated two detectable fragments corresponding to residues 6–40 and 17–40 (FIG. 4a). The predicted tryptic cleavage product representing residues 29–40 did not appear on the blot and may not be retained by the polyvinylidene difluoride membrane during transfer and treatment. Digestion is inhibited by the presence of increasing concentrations of $Zn^{2+}$. At 200 μM, $Zn^{2+}$ causes complete inhibition of Aβ hydrolysis; however, at this zinc level, tryptic activity is also slightly inhibited. Probing the blot with $^{65}Zn^{2+}$ confirmed the zinc binding identity of the peptide fragments and facilitated quantification of the hydrolysis of the zinc binding site (FIG. 4b). The rate of digestion of $A\beta_{1-40}$ and the $A\beta_{6-40}$ fragment is inhibited by the presence of zinc, whereas the digestion of the $A\beta_{17-40}$ fragment is not inhibited by increasing zinc concentrations. Hence, only the peptides possessing the intact zinc binding domain of Aβ (residues 6–28), and therefore capable of binding $Zn^{2+}$ (FIG. 4b), have their rates of digestion inhibited by zinc in this experiment. These data indicate that secretase-type cleavage of Aβ can be inhibited by $Zn^{2+}$ binding to the Aβ substrate. The results of the preceding experiments can be summarized as follows.

Firstly, the data indicates that soluble $Aβ_{1-40}$ possesses high and low affinity zinc binding sites. Secondly, the zinc binding site on Aβ maps to residues 6–28, with possibly conformational- and histidine-dependent properties. Thirdly, the affinity constants for zinc binding indicate that both binding associations are within physiological zinc concentrations. The binding of zinc may inhibit the action of a-secretase type cleavage of the peptide. Furthermore, occupancy of the low affinity binding site may be associated with accelerated precipitation of Aβ by aluminum silicate (kaolin). Occupancy of the high affinity site appears to have little effect on Aβ precipitation and is very highly specific, although the data cannot exclude the possibility of specific binding sites for alternative metals elsewhere on Aβ. Finally, copper's strong conformational interaction (dimerization and fluorescence) with Aβ indicates that it may also directly interact with the peptide and may have a role in preventing Aβ precipitation onto aluminum silicate.

Extracellular zinc may modify the adhesiveness of APP to extracellular matrix elements (Bush et al., *J. Biol. Chem.* 268:16109–16112 (1993)) and thus be an important factor in the physiology of the protein. Although the physiological function of APP remains unclear, the protein is thought to play a role in cell adhesiveness (Shivers et al., *EMBO J.* 7:1365–1370 (1988)) and neurite outgrowth (Milward et al., *Neuron* 9:129–137 (1992)). Physiological function of the Aβ-zinc interaction is also unclear, however, increased resistance of Aβ to proteolytic cleavage in the presence of zinc would increase the peptide's biological half-life, and the resulting increase in adhesiveness may also promote its binding to extracellular matrix elements. It has been reported recently that Aβ also promotes neurite outgrowth by complexing with laminin and fibronectin in the extracellular matrix (Koo et al., *Proc. Natl. Acad. Sci. USA* 90:4748–4752 (1993)). Hence, both APP and Aβ may interact with the extracellular matrix to modulate cell adhesion. The possibility that zinc is a local environmental cofactor modulating this interaction merits further investigation.

APP is abundant in platelets and brain (Bush et al., *J. Biol. Chem.* 265:15977–15983 (1990)) where zinc is also highly concentrated (Baker et al., *Thromb. Haemostasis* 39:360–365 (1978); Frederickson, C. J., *Int. Rev. Neurobiol.* 31:145–328 (1989)). Although APP is concentrated in vesicles in both of these tissues (Bush et al., *J. Biol. Chem.* 265:15977–15983 (1990); Schubert et al., *Brain Res.* 563:184–194 (1991)), and zinc is actively taken up (Wolf et al., *Neurosci. Lett.* 51:277–280 (1984)) and stored in synaptic vesicles in nerve terminals throughout the telencephalon (Perez-Clausell and Danscher, *Brain Res.* 3371:91–98 (1985), the colocalization of APP with zinc in these vesicles has yet to be demonstrated. Vesicular zinc storage is thought to play a role in stabilizing functional molecules such as nerve growth factor (NGF) and insulin as insoluble intravesicular precipitates (Frederickson et al., *J. Histochem. Cytochem.* 35:579–583 (1987)). Zinc may similarly play a role in stabilizing APP and Aβ.

The well characterized interaction between insulin and zinc has several striking parallels to the interaction of Aβ and zinc. Like Aβ, insulin exhibits histidine-dependent high-affinity ($K_a=5$ μM) and low-affinity ($K_a=140$ μM) zinc binding with stoichiometries of 1:1 (insulin:zinc) and 1:2, respectively (Goldman and Carpenter, *Biochemistry* 13:4566–4574 (1974)). Additionally, metal-free insulin exhibits a pH-dependent polymerization pattern consisting of monomer, dimer, tetramer, hexamer, and higher aggregation states, in dynamic equilibrium. At neutral pH, zinc and other divalent metal ions shift the equilibrium toward the higher aggregation states. At stoichiometric ratios of $Zn^{2+}$:insulin in excess of 0.33, the peptide precipitates (Fredericq, E., *Arch. Biochem. Biophys.* 65:218–228 (1956)), reminiscent of zinc's effects upon Aβ observed in the current studies.

Aβ chelates zinc with such high affinity that reports of its neurotoxic effects in neuronal cultures (Yankner et al., *Science* 250:279–282 (1990); Koh et al., *Brain Res.* 533:315–320 (1990)) might be explained by a disturbance of zinc homeostasis. Aβ accumulates most consistently in the hippocampus, where extreme fluctuations of zinc concentrations occur (0.15–300 μM) (Frederickson, C. J., *Int. Rev. Neurobiol.* 31:145–328 (1989)), e.g., during synaptic transmission (Assaf and Chung, *Nature* 308:734–736 (1984; Howell et al., *Nature* 308:736–738 (1984); Xie and Smart, *Nature* 349:521–524 (1991)). Choi and co-workers (Weiss et al., *Nature* 338:212 (1989)) have proposed that this trans-synaptic movement of zinc may have a normal signaling function and may be involved in long term potentiation. The hippocampus is the region of the brain that both contains the highest zinc concentrations (Frederickson et al., *Brain Res.* 273:335–339 (1983)) and is most severely and consistently affected by the pathological lesions of Alzheimer's disease (Hyman et al., *Ann. Neurol.* 20:472481 (1986)). One of the prominent neurochemical deficits in Alzheimer's disease is cholinergic deafferentation of the hippocampus, which has been shown to raise the concentration of zinc in this region (Stewart et al., *Brain Res.* 290:43–51 (1984)).

The rapid zinc-accelerated precipitation of Aβ by aluminum silicate (kaolin) is significant because of the candidacy of aluminum as a pathogenic agent in AD (Perl and Brody, *Science* 208:297–299 (1980)). Recent reports of $Zn^{2+}$-and $Al^{3+}$-induced sedimentation of Aβ (Mantyh et al., *J. Neurochem.* 61:1171–1174 (1993)), and the nucleation of Aβ precipitation by aluminosilicate (Candy et al., *Biochem. Soc. Trans.* 21:53S (Abstract) (1992)) also support these observations.

Evidence for altered zinc metabolism in AD includes decreased temporal lobe zinc levels (Wenstrup et al., *Brain Res.* 533:125–131 (1990); Constantinidis, *Encephale* 16:231–239 (1990); Corrigan et al., *Biometals* 6:149–154 (1993)), elevated (80%) cerebrospinal fluid levels (Hershey et al., *Neurology* 33:1350–1353 (1983)), increased hepatic zinc with reduced zinc bound to metallothionein (Lui et al., *J. Am. Geriatr. Soc.* 38:633–639 (1990)), a $Zn^{2+}$-modulated abnormality of APP in AD plasma (Bush et al., *Ann. Neurol.* 32:57–65 (1992)), an increase in extracellular $Zn^{2+}$-metalloproteinase activities in AD hippocampus (Backstrom et al., *J. Neurochem.* 58:983–992 (1992)), and decreased levels of astrocytic growth inhibitory factor, a metallothionein-like protein which chelates zinc (Uchida et al., *Neuron* 7:337–347 (1991)). Collectively, these reports indicate that there may be an abnormality in the uptake or distribution of zinc in the AD brain causing high extracellular concentrations and low intracellular concentrations. Meanwhile, environmentally induced elevations of brain concentrations of both zinc (Duncan et al., *J. Neurosci.* 12:1523–1537 (1992)) and aluminum (Garruto et al., *Proc. Natl. Acad. Sci. USA* 81:1875–1879 (1984); Perl et al., *Science* 217:1053–1055 (1982)) have been implicated in the pathogenesis of GALS/PDC complex, a disease also characterized by neurofibrillary tangles (Guiroy et al., *Proc.*

Natl. Acad. Sci. USA 84:2073–2077 (1987)). Interestingly, a pervasive abnormality of zinc metabolism manifested by immunological and endocrine dysfunction has been described as a common complication of Down's syndrome (Franceschi et al., *J. Ment. Defic. Res.* 32:169–181 (1988); Bjorksten et al., *Acta. Pediatr. Scand.* 69:183–187 (1980)), a condition characterized by the invariable onset of presenile Aβ deposition and Alzheimer's disease (Rumble et al., *N. Engl. J. Med.* 320:1446–1452 (1989)).

These results indicate that abnormally high zinc concentrations increase Aβ resistance to secretase-type cleavage and also accelerate Aβ precipitation onto aluminosilicates. Zinc-induced accumulation of Aβ in the neuropil may, in turn, invoke a glial inflammatory response, free radical attack, and oxidative cross-linking to form an, ultimately, "mature" amyloid. Collectively, these findings support the biochemical rationale for the chelation approach in the therapy of Alzheimer's disease (Crapper McLachlan et al., *Lancet* 337:1304–1308 (1991)), since reduction of cerebral concentrations of both aluminum and zinc could potentially decelerate the precipitation of Aβ. The assay of the present invention is ideally suited for the preparation of a kit. Such a kit may comprise a carrier means being compartmentalized to receive in close confinement therein one or more container means, such as vials, tubes, and the like, each of said container means comprising one of the separate elements of the assay to be used in the method. For example, there may be provided a container means containing standard solutions of the Aβ peptide or lyophilized Aβ peptide and a container means containing a standard solution or varying amounts of a heavy metal cation capable of binding to the peptide comprising at least amino acids 6 to 28 of Aβ peptide, in any form, i.e., in solution or dried, soluble or insoluble, in addition to further carrier means containing varying amounts and/or concentrations of reagents used in the present methods, e.g., standard solutions or varying amounts of chealators of heavy metal cations in any form, in solution or dried. Standard solutions of Aβ peptide preferably have concentrations above about 10 $\mu$M, more preferably from about 10 to about 25 $\mu$M or if the peptide is provided in its lyophilized form, it is provided in an amount which can be solubilized to said concentrations by adding an aqueous buffer or physiological solution. Standard solutions of heavy metal cations preferably have concentrations above 300 nM, more preferably about 25 $\mu$M. The standard solutions of analytes may be used to prepare control and test reaction mixtures for comparison, according to the methods of the present invention for determining whether a compound inhibits formation of Aβ amyloid.

These studies show that Aβ binds zinc in a saturable and specific manner. Moreover, they demonstrate that physiological concentrations of $Zn^{2+}$ increase the resistance of the peptide to proteolytic catabolism and promote Aβ precipitation by aluminosilicate. Based on these findings, it is possible that excessive zinc concentrations accelerate Aβ deposition in AD and related pathological conditions.

Further, the effects of physiological concentrations of zinc upon the stability of synthetic human Aβ$_{1-40}$ in solution were studied, using the rat/mouse species of the peptide ("rat Aβ") for comparison. Soluble Aβ$_{1-40}$ is produced by rat neuronal tissue (C. Haass and D. J. Selkoe, personal communication), however, Aβ amyloid deposition is not a feature of aged rat brains (D. W. Vaughan and A. Peters, *J. Neuropathol. Exp. Neurol.* 40:472 (1981)). β-amyloidogenesis occurs in other aged mammals possessing the human Aβ sequence, which is strongly conserved in all reported animal species, except rat and mouse (E. M. Johnstone, M. O. Chaney, F. H. Norris, R. Pascual, S. P. Little, *Mol. Brain Res.* 10:299 (1991)). The rat/mouse Aβ substitutions (Arg→Gly, Tyr→Phe and His→Arg at positions 5, 10 and 13, respectively [B. D. Shivers et al., *EMBO J.* 7:1365 (1988)]) appear to cause a specific change in the peptide's physicochemical properties sufficient to confer upon the peptide its relative immunity to amyloid formation. Since zinc binding to human Aβ$_{1-40}$ is histidine-mediated, the altered zinc binding properties of rat Aβ are entirely consistent with the proposed mechanism and binding site of the human peptide.

Figure 5:
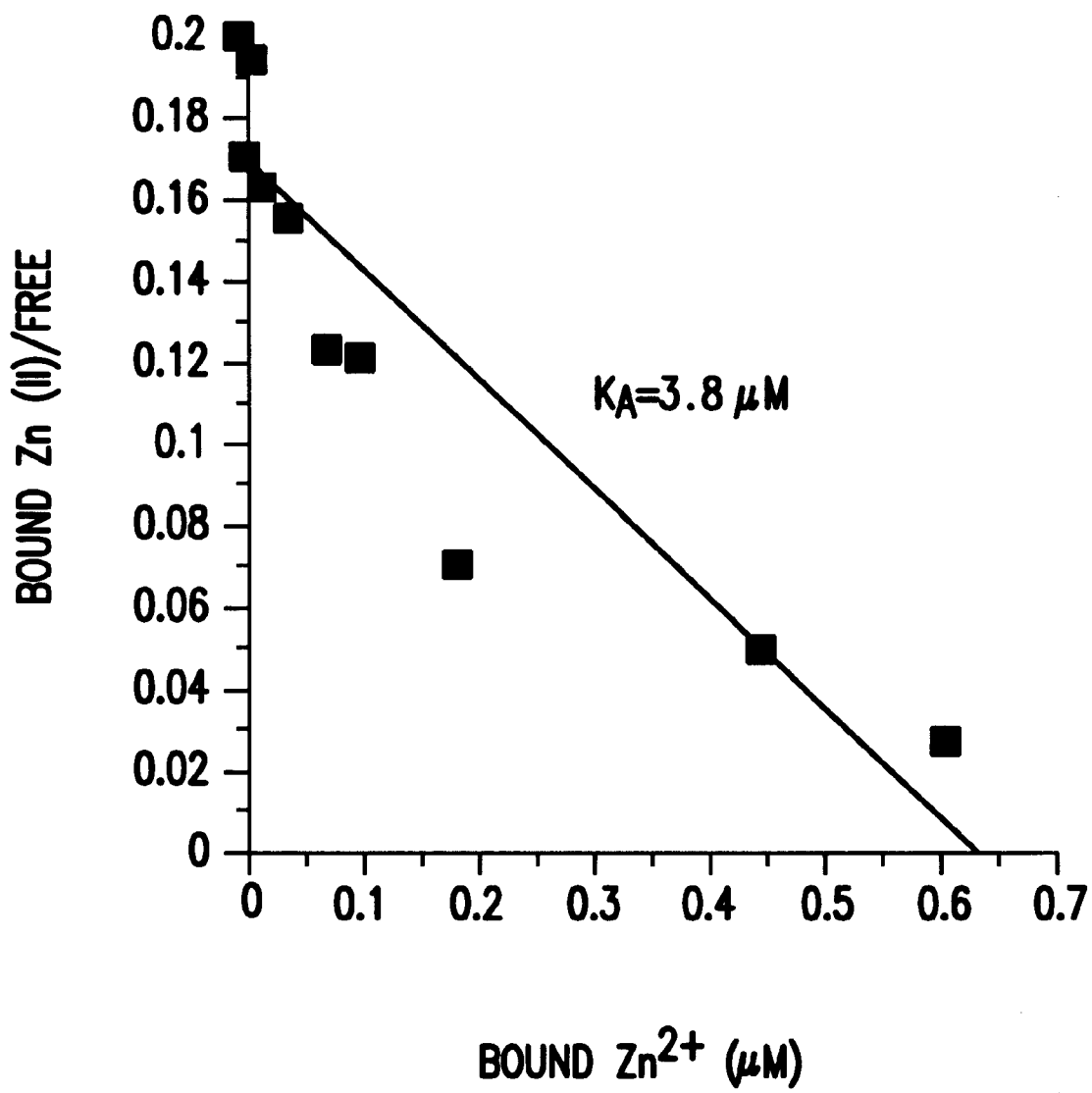
FIG. 5 depicts a graph showing a scatchard analysis of $^{65}Zn$ binding to rat $Aβ_{1-40}$. Dissolved peptides (1.2 nMol) were dot-blotted onto 0.20μ PVDF membrane (Pierce) and competition analysis performed as described in Example 1 (FIG. 1). Rat $Aβ_{1-40}$ and human $Aβ_{1-40}$ were synthesized by solid-phase Fmoc chemistry. Purification by reverse-phase HPLC and amino acid sequencing confirmed the synthesis. The regression line indicates a $K_A$ of 3.8 μM. Stoichiometry of binding is 1:1. Although the data points for the Scatchard curve are slightly suggestive of a biphasic curve, a biphasic iteration yields association constants of 2 and 9 μM, which does not justify an interpretation of physiologically separate binding sites.

The binding affinity of zinc to rat Aβ$_{1-40}$ was studied in a $^{65}$Zn competitive assay system as described in Example 1 (FIG. 1), to measure the $K_A$ of zinc binding to human Aβ$_{1-40}$. In contrast to human Aβ$_{1-40}$, the Scatchard analysis of zinc binding to rat Aβ$_{1-40}$ reveals only one binding association ($K_A$=3.8 $\mu$M), with 1:1 stoichiometry (FIG. 5).

Figure 6A:
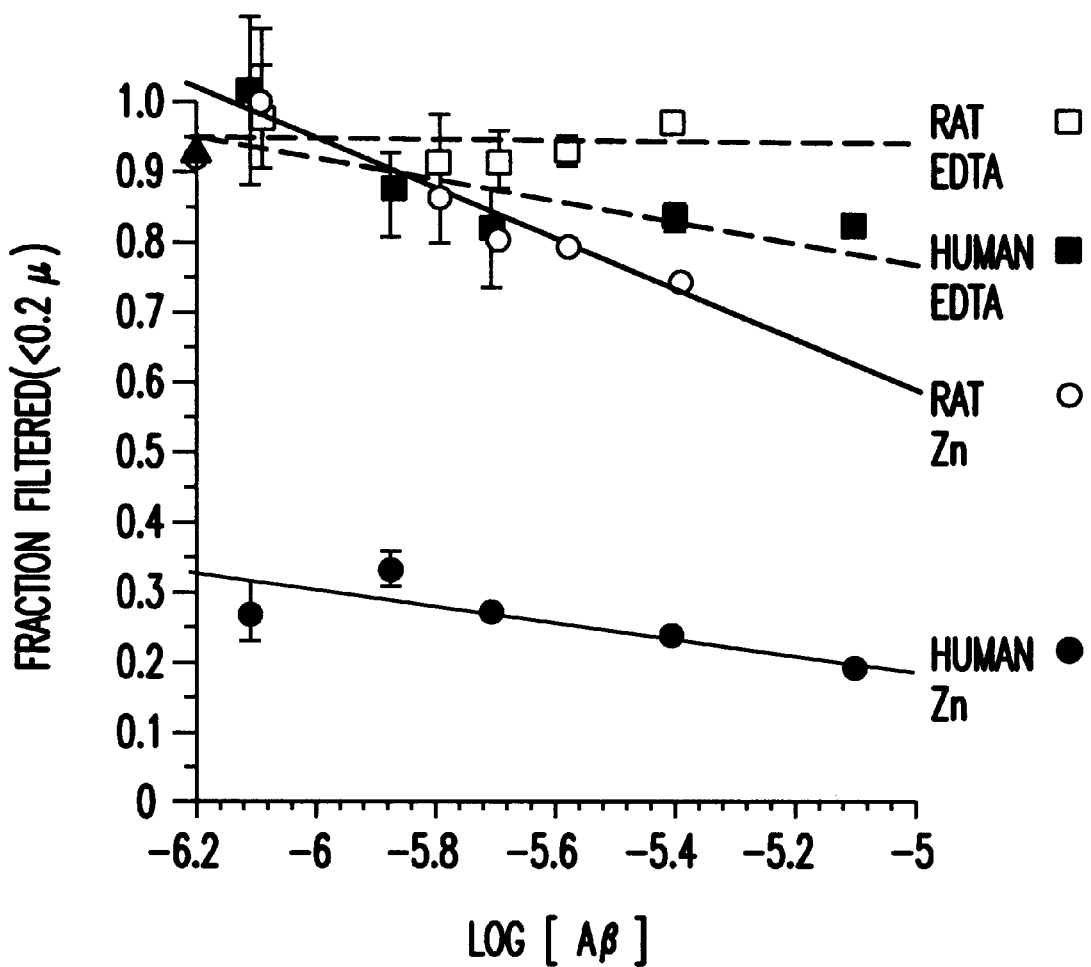
FIGS. 6a, 6b, 6c and 6d depict graphs showing the effect of zinc upon human, $^{125}$I-human and rat $Aβ_{1-40}$ aggregation into >0.2μ particles. Stock human and rat $Aβ_{1-40}$ peptide solutions (16 μM) in water were pre-filtered (Spin-X, Costar, 0.2μ cellulose acetate, 700 g), brought to 100 mM NaCl, 20 mM Tris-HCl, pH 7.4 (buffer 1)±EDTA (50 μM) or metal chloride salts, incubated (30 minutes, 37° C.) and then filtered again (700 g, 4 minutes). The fraction of the $Aβ_{1-40}$ in the filtrate was calculated by the ratio of the filtrate $OD_{214}$ (the response of the $OD_{214}$, titrated against human and rat $Aβ_{1-40}$ concentrations (up to 20 μM in the buffers used in these experiments), was determined to be linear) relative to the $OD_{214}$ of the unfiltered sample. All data points are in triplicate, unless indicated. (6a) A graph showing the proportions of $Aβ_{1-40}$, incubated±$Zn^{2+}$ (25 μM) or EDTA (50 μM) and then filtered through 0.2μ, titrated against peptide concentration. (6b) A graph showing the proportion of $Aβ_{1-40}$ (1.6 μM) filtered through 0.2μ, titrated against $Zn^{2+}$ concentration. $^{125}$I-human $Aβ_{1-40}$($^{125}$I-human $Aβ_{1-40}$ was prepared according to the method in Mantyh et al., J.

It was observed that the recovery of human Aβ$_{1-40}$ in filtration chromatography is dramatically reduced in the presence of zinc, due, in part, to increased adhesiveness of Aβ. To determine whether the aggregation of human Aβ$_{1-40}$ is also enhanced in the presence of zinc, the peptide was incubated with various concentrations for 30 minutes with $Zn^{2+}$ (25 $\mu$M) or EDTA and then filtered the solutions through 0.2$\mu$ filters. Zinc caused up to 80% of the available peptide to aggregate into >0.2$\mu$ particles (FIG. 6A). (Incubation of Aβ$_{1-40}$ solutions in the filter devices, without actual filtration, indicated that there was no non-specific loss of peptide to the plastic or membrane surfaces.) There appears to be a shallow negative log-linear relationship between human Aβ peptide concentration and the proportion of filterable peptide in 25 $\mu$M $Zn^{2+}$, but even at the lowest concentration tested (0.8 $\mu$M), >70% of the human Aβ$_{1-40}$ solution aggregated. In contrast, the effect of $Zn^{2+}$ on rat Aβ$_{1-40}$ was unremarkable, with no aggregation of a 0.8 $\mu$M peptide solution detected under the same conditions, and only 25% aggregation of a 4 $\mu$M solution. Meanwhile, in the presence of EDTA, human and rat Aβ$_{1-40}$ solutions behaved indistinguishably, with no detectable aggregation observed at 0.8 $\mu$M, and≈15% aggregation at higher peptide concentrations.

Next, the formation of >0.2$\mu$ Aβ particles was titrated against increasing zinc concentrations (FIG. 6B), and a shallow response curve for human Aβ$_{1-40}$ (1.6 $\mu$M) was observed until the zinc concentration reached 300 riM, corresponding to the saturation of high-affinity binding. At zinc concentrations above 300 nM, corresponding to low-affinity binding, human Aβ$_{1-40}$ dramatically aggregates. In contrast, rat Aβ$_{1-40}$ remains stable in the presence of up to 10 $\mu$M zinc, and only at 25 $\mu$M zinc was aggregation observed.

Figure 6B:
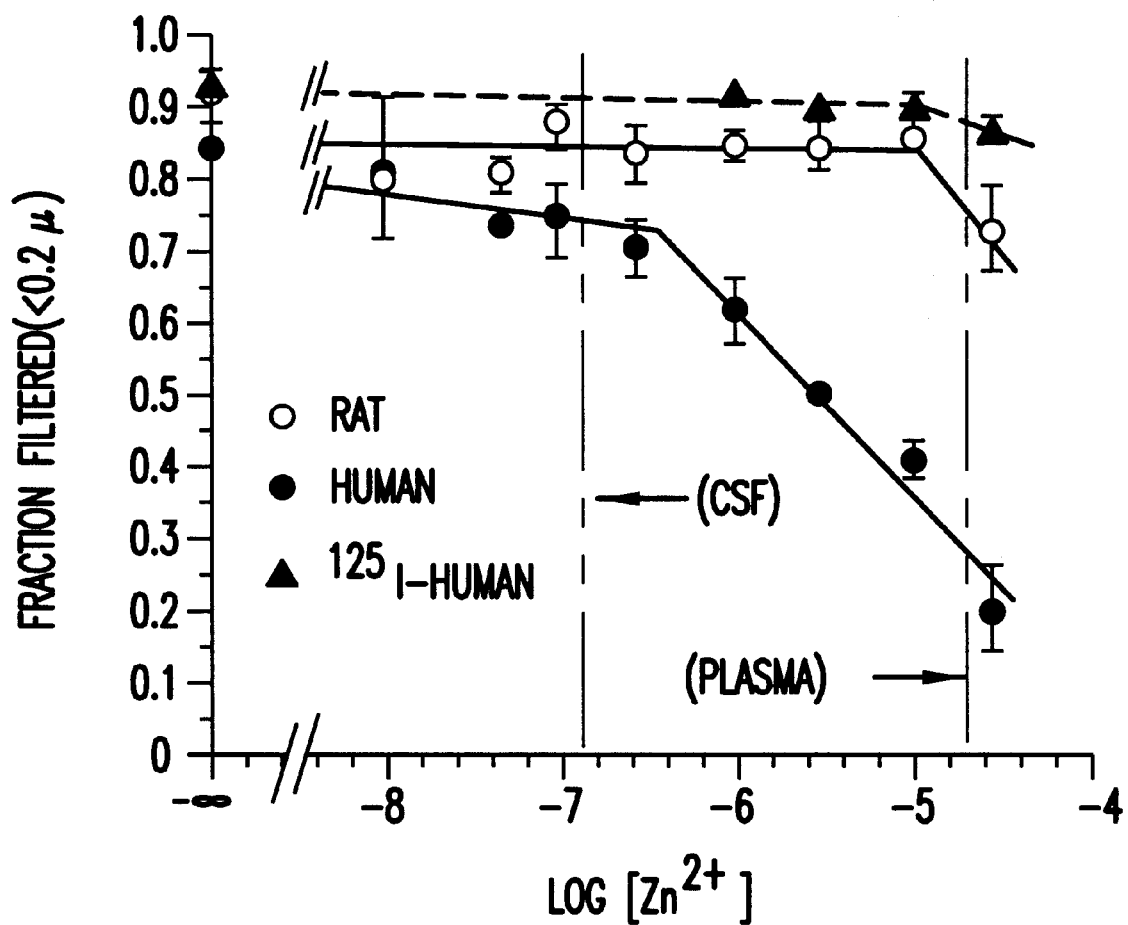

To determine the effects of zinc on Aβ$_{1-40}$ at physiological peptide concentrations requires an assay more sensitive than spectroscopy. (Human Aβ$_{1-40}$ at 0.8 $\mu$M in buffer 1 corresponds to 0.090 absorbance units at 214 nm. Aggregation studies of peptides at lower starting concentrations would involve readings at the limits of sensitivity). Thus, the effects of zinc on $^{125}$I-human Aβ$_{1-40}$ used as a tracer in the presence of unlabeled peptide was characterized. Unlike its unlabeled precursor, $^{125}$I-Aβ$_{1-40}$ (at 1.6 $\mu$M total peptide) remained stable in the presence of increasing zinc concentrations, indicating that $^{125}$I-Aβ$_{1-40}$ is not a suitable tracer (FIG. 6B). The tracer is iodinated on the tyrosine residue at position 10, which is a phenylalanine in the rat peptide. Thus, the tyrosine residue may be critical to the stability of the human peptide. These data may also explain why a recent report required relatively high concentrations of $Zn^{2+}$ (1 mM) to precipitate $^{125}$I-human Aβ$_{1-40}$ in centrifugation studies (P.

Figure 6C:
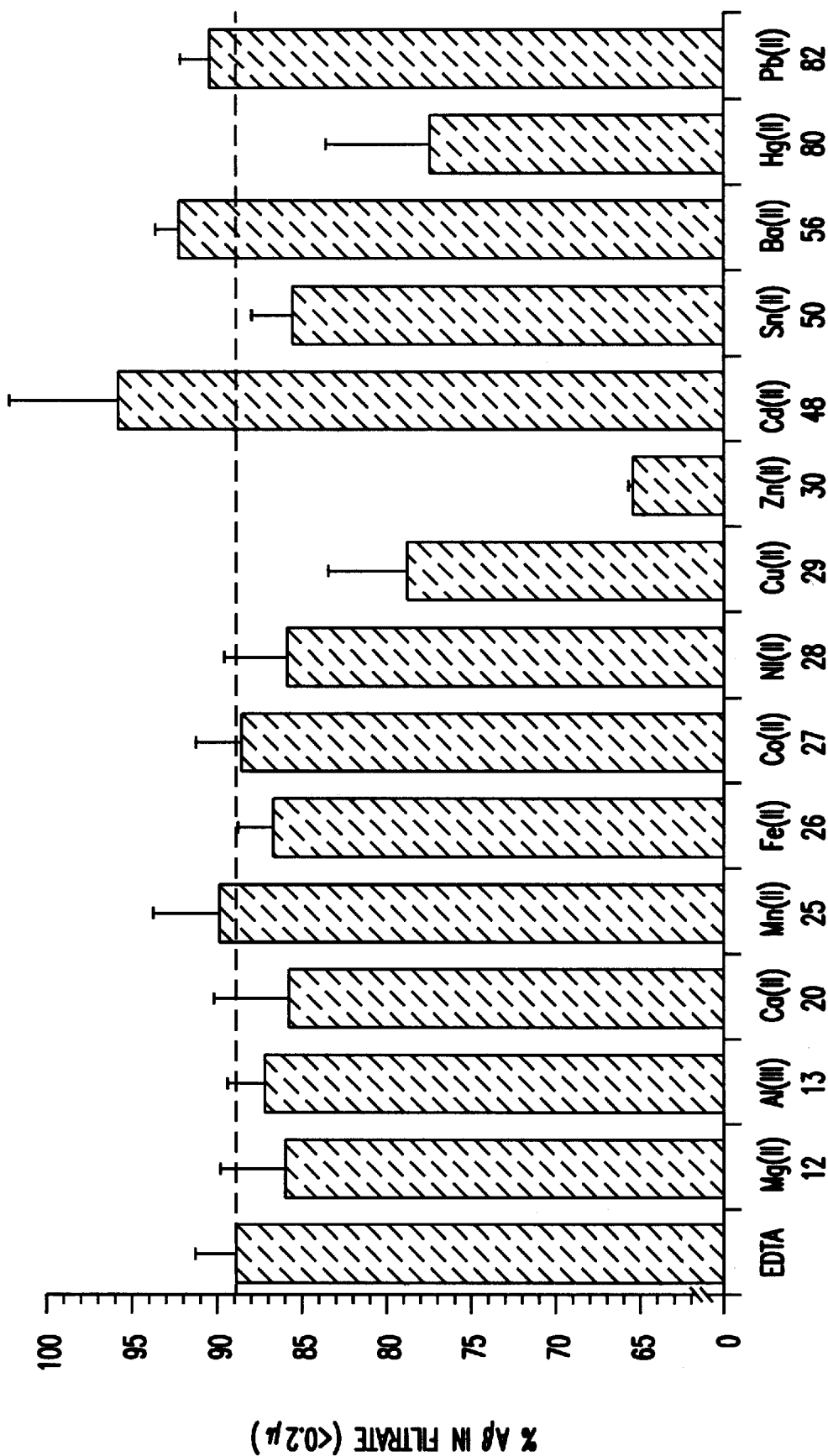
Figure 6D:
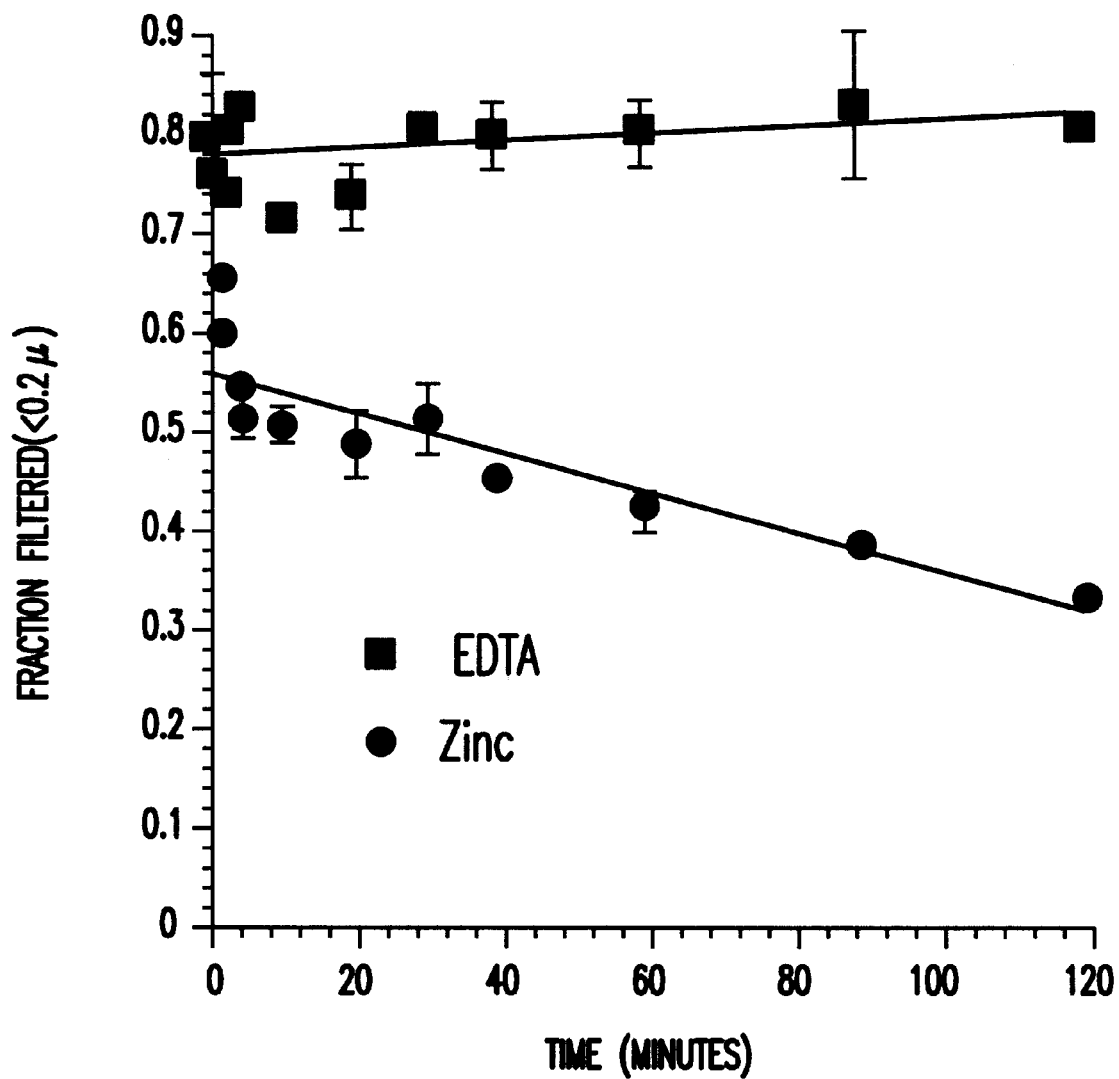

W. Mantyh et al., *J. Neurochem.* 61:1171 (1993)). Extrapolating the curve in FIG. 6A to 0.6 nM currently provides the best estimate of the effect of zinc upon physiological Aβ concentrations (M. Shoji et al., *Science* 258:126 (1992); P. Seubert et al., *Nature* 359:325 (1992)), and indicates that 25% of the peptide would aggregate into >0.2μ particles under these conditions. The specific vulnerability of human Aβ$_{1-40}$ for Zn$^{2+}$ is indicated by the observation that Zn$^{2+}$ is the only one of several metal ions tested on an equimolar basis, including Al$^{3+}$, to induce significant aggregation of human Aβ$_{1-40}$ in this system (FIG. 6C).

Next, the kinetics of the assembly of zinc-induced human Aβ$_{1-40}$ aggregates (FIG. 6D) was investigated. (In order to achieve time point measurements of less than 1 minute, the procedure was modified so that samples were centrifuged at 2500 g, allowing the sample volume to be completely filtered in 40 seconds.) The data obtained indicate that following the addition of stock Aβ$_{1-40}$ in water (15.9 μM, pH 5.6) to Zn$^{2+}$ (25 μM) in saline buffer (pH 7.4) there is a near-instantaneous aggregation of the peptide (1.6 μM final concentration) into filterable particles with two phases observed over two hours. The initial phase is rapid, with a half-maximal assembly rate of≈0.4 μM/min. The steady state of the second phase is achieved within about 2 minutes, whereupon particle assembly proceeds at a rate of 3.2 nM/min with no evidence of saturation within 2 hours. At this rate, the available peptide is exhausted within five hours of initiation. Although the addition of EDTA buffer caused the near-instantaneous aggregation of 20% of the 1.6 μM Aβ$_{1-40}$ solution into >0.2μ particles, no further particle assembly was observed over the time course of the experiment. In comparison, human Aβ$_{1-40}$ (20 μM in PBS, pH 7.4) has been reported to be stable for 10 days (J. T. Jarrett, E. P. Berger, P. T. Lansbury, *Biochemistry* 32:4693 (1993)), and seeding the solution with Aβ$_{1-42}$ (2 μM), the more amyloidogenic Aβ species, induced aggregation of this solution which was half-maximal only after 4–5 days. Thus, the results presented here represent a major advance among attempts to induce amyloid formation in vitro using the wild-type form of the main species of secreted Aβ (Aβ$_{1-40}$).

Figure 7B:
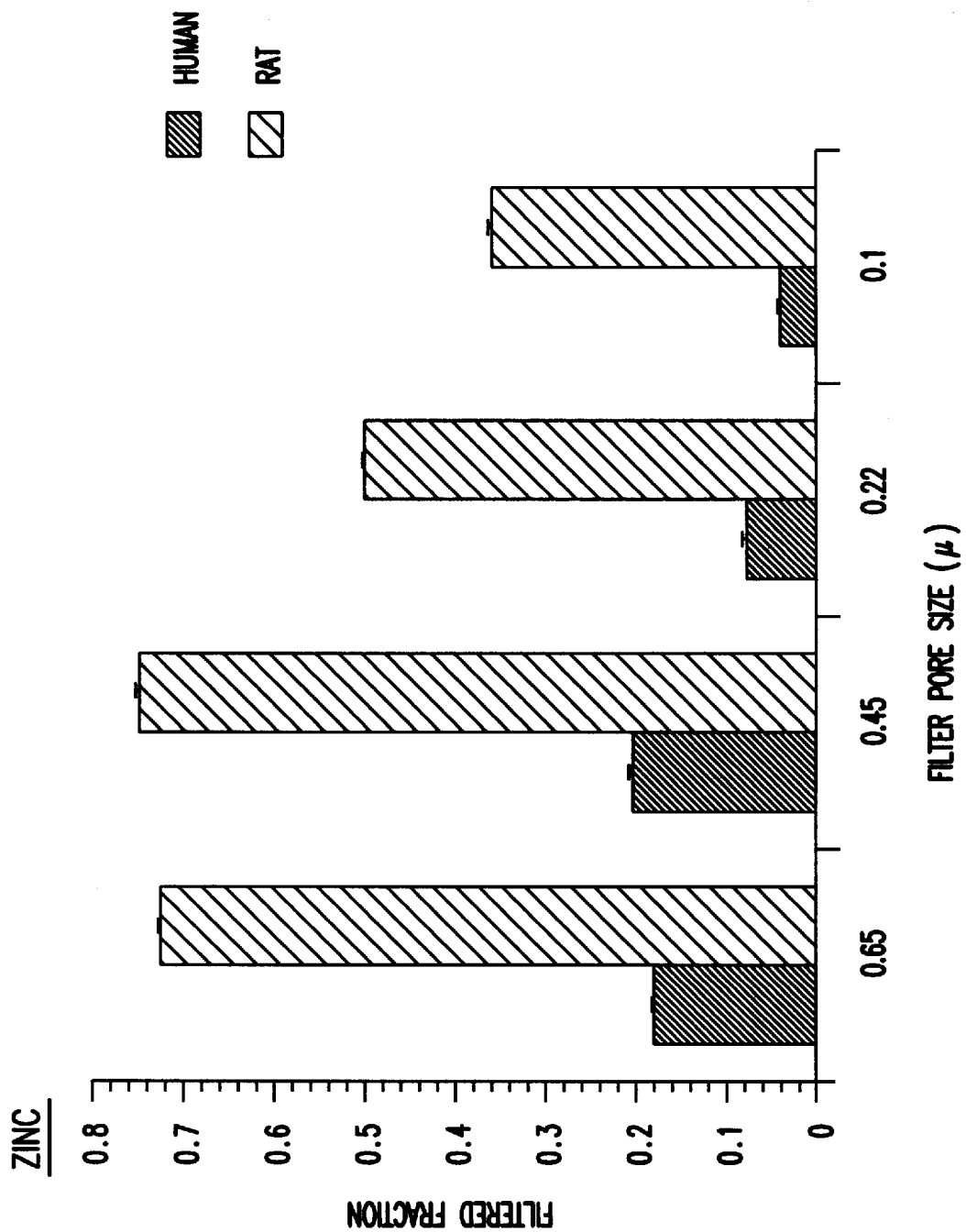
Figure 7C:
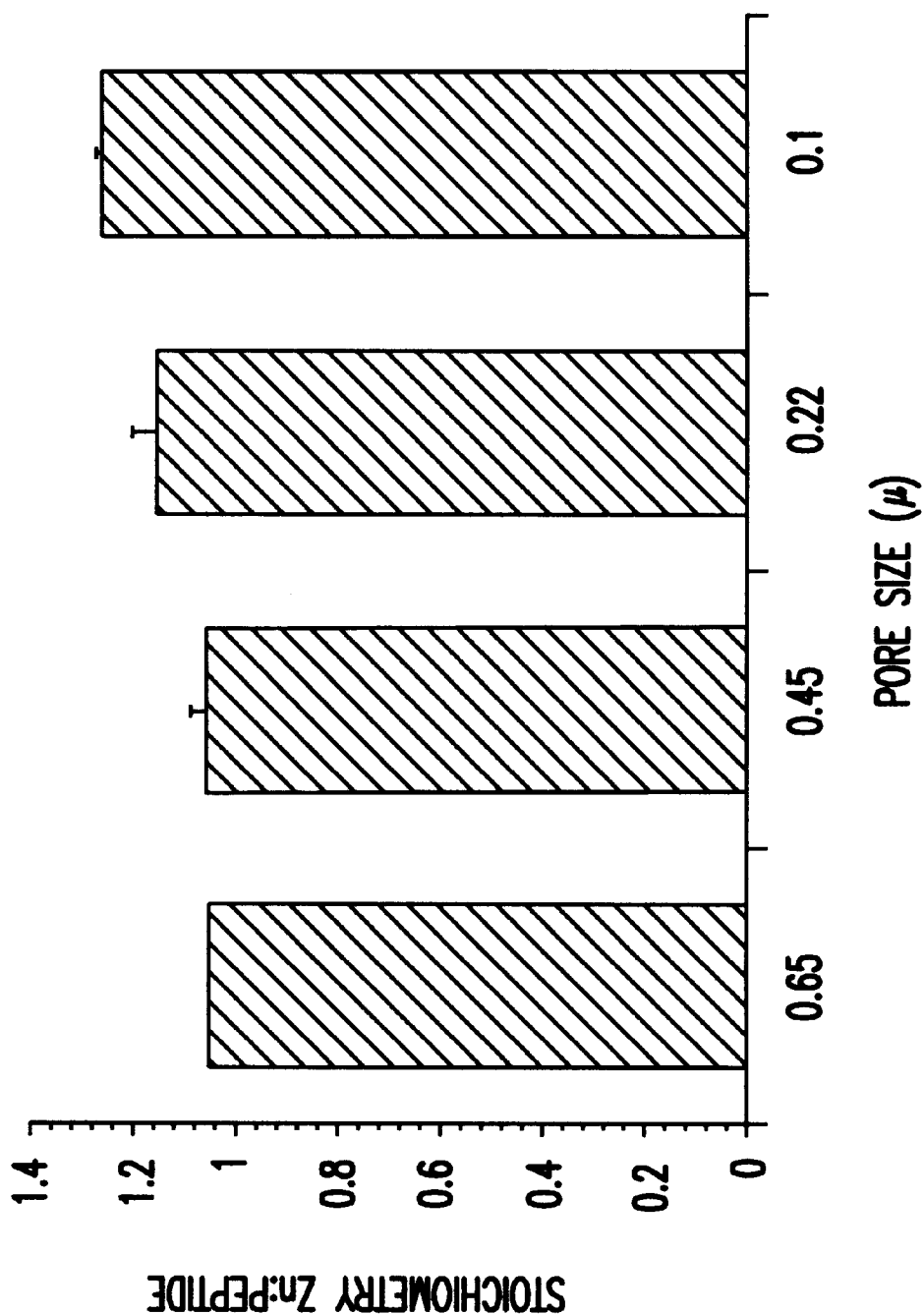

To estimate the size of the Aβ aggregates formed in the presence of zinc, Aβ$_{1-40}$ (1.6 μM) was incubated with Zn$^{2+}$ (25 μM) or EDTA and then passed through filters with various pore sizes (FIGS. 7a and 7b). Following incubation in EDTA, human Aβ$_{1-40}$ assembled into populations of heterogeneous particle sizes, >0.1/μ: 47%, >0.22μ: 40%, >0.65μ: 32%. The comparable proportions of filtered rat Aβ$_{1-40}$ particles were, >0.1μ: 36%, >0.22μ: 27%, >0.65μ: 25%. Upon incubation with Zn$^{2+}$ (25 μM), the proportion of >0.65μ rat peptide particles increased only slightly, however the proportion of >0.65μ human peptide particles dramatically increased, recruiting 82% of the available peptide. Interestingly, the proportions of >0.1μ and >0.22μ particles formed from the human Aβ$_{1-40}$ also increased by 50 and 55%, respectively, following incubation with Zn$^{2+}$, however, the same reaction induced only a 20% and 30% increase, respectively, in the amounts of these particles assembled from rat peptide. Remarkably, only 4% of the human Aβ $1_{40}$ incubated with Zn$^{2+}$ remained in solution following 0.1β filtration. Collectively, these data indicate that the human species of Aβ$_{1-40}$ differs from the rat species both in the extent and size of zinc-induced particle formation.

Figure 7D:
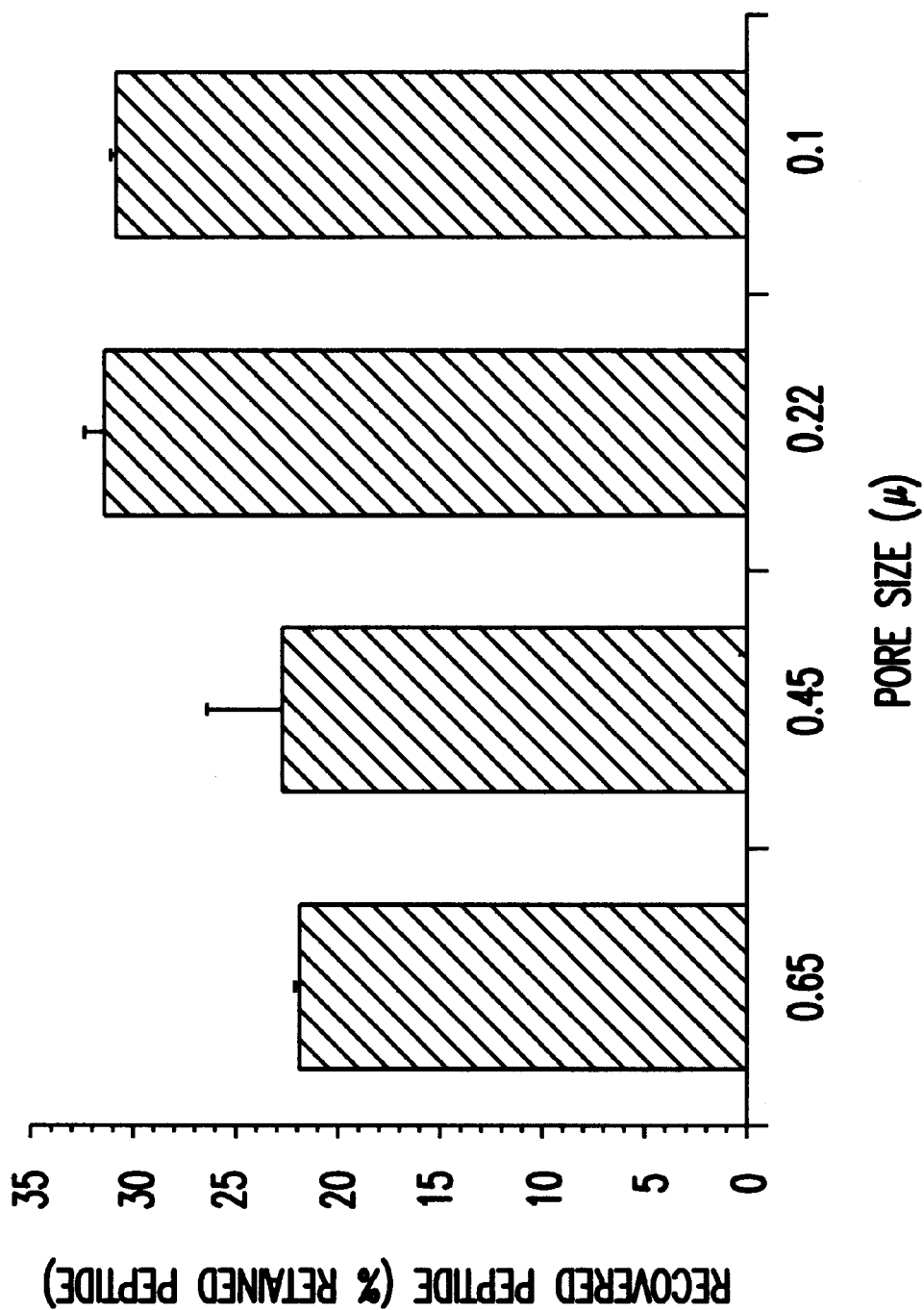

The stoichiometry of zinc:human Aβ in these aggregates is at least 1:1 (FIG. 7c), but increases to 1.3:1 with the smaller (0.1μ) pore size filters. Because the stoichiometries for high- and low-affinity Zn:Aβ binding are ≈1:1 and≈2:1 respectively, these data indicate that formation of >0.65μ Aβ aggregates is mediated by high-affinity zinc interaction, whereas low-affinity zinc interaction most likely contributes to the formation of smaller (<0.22μ) aggregates. Interestingly, when the retained aggregates are washed with EDTA, only 22% of the peptide is recovered from >0.65 aggregates, although the complexed zinc (using $^{65}$Zn as tracer) is completely recovered (FIG. 7d). This indicates that zinc-induced Aβ aggregation is largely irreversible by chelation. The amount of≦0.22μ peptide resolubilized by EDTA treatment is 7% greater, which may reflect the increased contribution of low-affinity zinc binding to the smaller, chelation-reversible, Aβ particle formation.

Sedimentation of zinc-induced Aβ particles by centrifugation resulted in an abundant precipitate of human Aβ$_{1-40}$ which stained with Congo Red (FIG. 8a) and manifested green birefringence under polarized light (FIG. 8b), meeting the criteria for tinctorial amyloid formation. However, following incubation with Zn$^{2+}$ under the same conditions, the rat peptide formed significantly fewer and smaller particles, with minimal birefringence. No rat Aβ amyloid was induced by Zn$^{2+}$ concentrations of less than 10 μM, whereas, by tinctorial criteria, human Aβ amyloid was induced by Zn$^{2+}$ concentrations as low as 3 μM. In neither case was Congo Red-stained material detected following incubation with EDTA-containing buffer.

Taken together, these data indicate that soluble human Aβ$_{1-40}$ has a dramatically greater propensity than rat Aβ$_{1-40}$ to form amyloid in the presence of physiological zinc concentrations. The tinctorial amyloid aggregates are frequently as large as the amorphous amyloid plaque cores purified from AD brain tissue (C. L. Masters et al., *Proc. Natl. Acad. Sci. USA* 82:4245 (1985)). Meanwhile, the small degree (10–20%) of >0.2μ Aβ$_{1-40}$ particle assembly observed following the incubation of Aβ$_{1-40}$ with EDTA probably reflects the relatively slow aggregation which occurs in the presence of neutral pH (S. Tomski and R. M. Murphy, *Arch. Biochem. Biophys.* 294:630 (1992)) and NaCl (C. Hilbich, B. Kisters-Woike, J. Reed, C. L. Masters, K. Beyreuther, *J. Mol. Biol.* 218:149 (1991)). Hence, the specific vulnerability of human Aβ to zinc-induced amyloid formation is a promising explanation for aspects of the pathology of AD and related pathological conditions.

The cerebral cortex, and especially the hippocampus, contains the highest concentrations of zinc in the body (C. J. Frederickson, M. A. Klitenick, W. I. Manton, J. B. Kirkpatrick, *Brain Res.* 273:335 (1983)), and is exposed to extreme fluctuations of extracellular zinc levels (0.15 to 300 μM, C. J. Frederickson, *Int. Rev. Neurobiol.* 31:145 (1989)), e.g. during synaptic transmission (S. Y. Assaf and S.-H. Chung, *Nature* 308:734 (1984); G. A. Howell, M. G. Welch, C. J. Frederickson, *Nature* 308:736 (1984)). The cortical vasculature contains an intraluminal zinc concentration of 20 μM (I. J. T. Davies, M. Musa, T. L. Dormandy, *J. Clin. Pathol.* 21:359 (1968)), but the perivascular interstitial zinc concentration is 0.15 μM (C. J. Frederickson, *Int. Rev. Neurobiol.* 31:145 (1989)). Both sites of high zinc concentration gradients are severely and consistently affected by the pathological lesions of AD (B. T. Hyman, G. W. Van Hoesen, L. J. Kroner, A. R. Damasio, *Ann. Neurol.* 20:472 (1986); G. G. Glenner and C. W. Wong, *Biochem. Biophys. Res. Commun.* 120:885 (1984)). Interestingly, a prominent neurochemical deficit in AD is cholinergic deafferentation of the hippocampus, which raises the concentration of zinc in this region (G. R. Stewart, C. J. Frederickson, G. A. Howell, F. H. Gage, *Brain Res.* 290:43 (1984)). Additional evidence for altered cerebral zinc metabolism in AD include decreased temporal lobe zinc levels (D. Wenstrup, W. D. Ehmann, W. R. Markesbery, *Brain Res.* 533:125 (1990); J. Constantinidis, *Encephale* 16:231 (1990); F. M. Corrigan, G. P. Reynolds, N. I. Ward, *Biometals* 6:149 (1993)), elevated (80%) CSF levels (C. O. Hershey et al., *Neurology* 33:1350 (1983)), an increase in extracellular $Zn^{2+}$-metalloproteinase activities in AD hippocampus (J. R. Backstrom, C. A. Miller, Z. A. Tökés, *J. Neurochem.* 58:983 (1992)), and decreased levels of astrocytic growth-inhibitory factor, a metallothionein-like protein which chelates zinc (Y. Uchida, K. Takio, K. Titani, Y. Ihara, M. Tomonaga, *Neuron* 7:337 (1991)). Recently, a clinical study assayed the effects of oral zinc supplementation (6.7-fold the recommended daily allowance, a dose commonly found in nutritional supplements) upon cognition and plasma APP levels in AD subjects and age-matched controls. Five sequentially-studied AD subjects each experienced an acute decline in cognition within forty-eight hours of ingesting the zinc dose. Under the same conditions, age-matched control subjects remained unaffected by the dose. Among the abnormal changes of neuropsychological measurements taken of the AD group was a 31% drop in Mini-Mental State Examination (M. F. Folstein, S. E. Folstein, P. R. McHugh, *J. Psychiatr. Res.* 12:189 (1975)) scores, after four days of zinc supplementation. This represented a deterioration which, in the ordinary course of the disease, would only be expected after two to four years (Galasko et al., *JAGS* 39:932 (1991)). Plasma APP levels also rose significantly in response to zinc in both the AD and the control groups. All changes were rapidly reversible following cessation of the four day supplementation. Collectively, these reports indicate that there may be an abnormality in the uptake or distribution of zinc in the AD brain. Pervasive abnormalities of zinc metabolism, and premature AD pathology, are also common clinical complications of Down's syndrome (C. Franceschi et al., *J. Ment. Defic. Res.* 32:169 (1988); B. Rumble et al., *N. Engl. J. Med.* 320:1446 (1989)).

The data presented here indicate that stability in the presence of physiological concentrations of zinc clearly differentiates the propensity of human and rat $A\beta_{1-40}$ peptide species to form amyloid. The rapid induction of tinctorial human $A\beta$ amyloid, under physiologically relevant conditions, at peptide concentrations more than an order of magnitude lower than the lowest levels achieved previously for $A\beta_{1-40}$ aggregation, and within two minutes of incubation, establishes a novel assay system for the study of $A\beta$ amyloidosis. More importantly, these findings can have profound implications for the potential role of zinc in Alzheimer-associated neuropathogenesis.

The following examples are provided by way of illustration to further describe certain preferred embodiments of the invention, and are not intended to be limiting of the present invention, unless specified.

EXAMPLES

Experimental Procedures

Unless otherwise indicated, the following experimental procedures, materials, and reagents were used in the present invention:

Reagents—Precautions taken to avoid zinc contamination included using analytical-grade reagents, electrophoresis-grade Tris-HCl (Bio-Rad), and highly deionized water. $A\beta_{1-17}$ was synthesized by the Biopolymers Laboratory, MIT. $A\beta_{40-1}$ (reverse peptide) was purchased from Bachem (Torrance, Calif.). Other reagents were from Sigma. $A\beta_{1-40}$ and $A\beta_{1-28}$ results were replicated with peptides from Bachem and Sigma. $A\beta_{1-40}$ results were also replicable with peptide synthesized by W. M. Keck Foundation Biotechnology Resource Laboratory, Yale University. $^{65}Zn$ was purchased from Amersham Corp.

$^{65}Zn^{2+}$ Binding Studies—Dissolved peptides (1.2 nMol, unless otherwise stated) were dot-blotted onto polyvinylidene difluoride membrane (0.2-µm pore size; Pierce Chemical Co.), washed twice with chelating buffer (200 µl×100 mM NaCl, 20 mM Tris-HCl, 1 mM EDTA, pH 7.4), then five times with blocking buffer (200 µl×100 mM NaCl, 20 mM Tris-HCl, 1 mM $MnCl_2$, pH 7.4), and then incubated (60 min, 20° C.) with $^{65}Zn$ (unless otherwise stated 130,000 cpm, 74 mM $^{65}ZnCl_2$ in 200 µl of blocking buffer±competing metal ion chloride). The dot-blot was then washed with blocking buffer (5×200 µl), the dot excised, placed in a test tube, and assayed by γ-counting (11% efficiency). The equilibration volume for stoichiometry estimates was regarded as 6×200 µl. The 214 nm UV absorbance of the unbound flow-through was assayed to determine the total amount of peptide remaining bound onto the membrane. Peptide stock concentrations were confirmed by amino acid analysis. To alter the pH, the $^{65}Zn$ incubation was carried out in the presence of 100 mM buffer: MOPS (pH 6.5–7.0), MES (pH 5.0–6.0), acetate (pH 3.5–4.5). The dot-blot apparatus was washed with detergent and EDTA (50 mM) then rinsed and siliconized between use.

$A\beta$ Chromatography—$A\beta$ (55 µg) was incubated with metal salt solution or EDTA in siliconized 1.5-ml plastic reaction vessels in 100 mM NaCl, 20 mM Tris-HCl, pH 7.4 ("TBS," 100 µl, 1 h, 37° C.). $A\beta$ was stored in aliquots of 0.52 mg/ml in water at −20° C., then kept at 4° C. when thawed. Reagents were mixed without vortex mixing. The incubated $A\beta$ was directly applied to a G50 SF (Pharmacia, Uppsala, Sweden) column (Bio-Rad Econo-Column, 30×0.7 cm) pre-equilibrated with metal salt solution or EDTA (50 µM) in TBS at 20° C. and eluted at 8 ml/h (Wiz peristaltic pump, Isco, Lincoln, Nebr.). Absorbance was measured at 254 and 214 nmn (Type 6 optical unit, Isco). The amount of $A\beta$ eluting at various peaks was estimated from the area under the curve. This was possible because the relationship of UV absorbance was determined to be linear over the range of $A\beta$ dilutions used in these studies, indicating that absorbance is proportional to the amount of peptide present despite polymerization state (see below). The maximum recovery of $A\beta$ occurs in the presence of EDTA. Because the sample eluted in a volume of approximately 15 ml, the average concentration of the peptide on the column was 0.8 µM.

To study the effects of protein blocking upon adsorption of $A\beta$ to the chromatography column, a Sephadex G50 SF column which had been characterized previously for $A\beta$ behavior was eluted with 3% bovine serum albumin (BSA) in TBS (50 ml) and equilibrated with non-BSA-containing buffer, subsequent to repeating the $A\beta$ experiments.

Spectroscopic Assay—Measurements were performed on a Hewlett-Packard 8452A diode array spectrophotometer using a 1-cm path length quartz cuvette. Concentration versus absorbance curves were performed at 214 nm, 254 nm, 280 nm, and full spectrum. 214 nm readings were 50-fold more sensitive in detecting the peptide than 254 nm readings, whereas the 280 nm readings of low micromolar $A\beta$ solutions were below sensitivity limits and hence could not be used in these studies. The standard curves generated were linear at concentrations below 0.1 mg/ml. In addition, the effects of $Cu^{2+}$, $Zn^{2+}$, EDTA, and TBS upon absorbance were examined. At concentrations below 0.1 mg/ml, adjusting the peptide in water to TBS caused ≈15% quenching.

Cu$^{2+}$-, Zn$^{2+}$-, and EDTA-containing Aβ solutions were studied for artifactual absorbance over the linear range of the 214 nm absorbance curve. 1 mM EDTA caused 60% quenching, hence 50 iM EDTA was employed, contributing a similar degree of quenching to that observed with Cu2+ and Zn$^{2+}$.

Aβ Binding to Kaolin (Aluminum Silicate)—Kaolin suspension was prepared in high performance liquid chromatography water (Fisher), defined, and adjusted to 50% (v/v). Aβ (40 µg) was incubated in siliconized reaction vessels with either kaolin or Sephadex G50 SF (10 µl×50% (v/v)) in Cu$^{2+}$, Zn$^{2+}$, or EDTA (100 µl in TBS, 5 min, room temperature). The suspension was then pelleted (1500×g, 3 min) and the supernatant removed and diluted 20-fold with water to bring the UV absorbance readings into the linear range. Samples were assayed at 214 nm before and after incubation with kaolin or Sephadex.

Tryptic Digestion of Aβ-Aβ$_{1-40}$ (13.9 µg) was incubated with Zn$^{2+}$ (12 µl in blocking buffer, 1 h, 37° C.) and then digested with trypsin (12 ng, 3 h, 37° C.). The reaction was stopped by adding SDS sample buffer containing phenylmethylsulfonyl fluoride (1 mM), boiling the samples (5 min), and applying the samples to Tris/Tricine gel electrophoresis and transfer. The blot was washed with EDTA, Coomassie-stained, incubated with $^{65}$Zn$^{2+}$, individual bands were excised, assayed for $^{65}$Zn$^{2+}$ binding, and N-terminal sequenced to confirm the identity of the digestion products. The effects of Zn$^{2+}$ (up to 100 µM in TBS) on the activity of trypsin, itself, were assayed by assay of Z-Arg-amido-4-methylcoumarin (Sigma) fluorescent cleavage product and determined to be negligible. It was found that 200 µM Zn$^{2+}$, however, inhibited tryptic activity by 12%.

Zinc- or Copper-treated microwell plate

Any standard microtitre plate, for example a Costar catalog no. 9017, can be used for making the heavy metal cation substrate which can trap Aβ protein. The plate is coated with a solvated nitrilotriacetic acid. Next, the divalent metal ion of choice, for example, zinc or copper metal cation, is added, which complexes to the surface of the plate. A preferred metal cation microtiter plate is available from Xenopore, Saddle Brook, N.J. (catalog number for zinc plates: ZCP00100, catalog number for copper plates: CCP00100). It is preferred that like the zinc and copper plates made by Xenopore, there be at least two free coordination sites available for binding to Aβ protein. In this way, the Aβ protein can competitively attach to and stay bound to the substrate via the heavy metal cation.

Chelating-Sepharose Chromatography

The chelating-Sepharose resin (250 µl) was poured into a disposable polystyrene column (Pierce, 29920) and packed between two porous polyethylene discs. In the following steps solutions were allowed to drain through the gel bed by gravity. The gel was first pre-equilibrated with 5 ml of equilibration buffer (MES 50 mM, pH 5.0 and NaCl 500 mM). The sample (10–15 ml) was then loaded on to the column. The gel was washed with 5 ml of equilibration buffer before bound protein was recovered by applying 1 ml of elution buffer to the gel (EDTA 50 mM, MES 50 mM, pH 5.0 and NaCl 500 mM) and collecting the eluate.

Example 1

Analyses of $^{65}$Zn$^{2+}$ binding to, Aβ

Aliquots of Aβ were incubated (60 min) with $^{65}$Zn$^{2+}$ in the presence of varying concentrations of unlabeled Zn$^{2+}$ (0.01–50 µM total). The proportion of $^{65}$Zn$^{2+}$ binding to immobilized peptide (1.0 nmol) described two binding curves as shown in FIG. 1a (Scatchard plot). Values shown are means±S.D., n≧3. The high-affinity binding curve has been corrected by subtracting the low-affinity component, and the low-affinity curve has had the high-affinity component subtracted. (FIG. 1b) depicts specificity of the Zn$^{2+}$ binding site for various metals. Aβ was incubated (60 min) with $^{65}$Zn$^{2+}$ (157 nM, 138,000 cpm) and competing unlabeled metal ions (50 µM total). (FIG. 1c) depicts $^{65}$Zn$^{2+}$ (74 nM, 104,000 cpm) binding to negative (aprotinin, insulin α-chain, reverse peptide 40-1) and positive (bovine serum albumin (BSA)) control proteins and Aβ fragments (identified by their residue numbers within the Aβ sequence, gln11 refers to Aβ$_{1-28}$ where residue 11 is glutamine). Percent binding of total counts $^{65}$Zn$^{2+}$/min added is corrected for the amounts (in nanomoles) of peptides adhering to the membrane. (FIG. 1d) depicts as for 1a, except with Aβ$_{1-28}$ peptide substituting for Aβ$_{1-40}$. 157 nM $^{65}$Zn (138,000 cpm) is used in this experiment to probe immobilized peptide (1.6 nmol). (FIG. 1e) depicts pH dependence of $^{65}$Zn$^{2+}$ binding to Aβ$_{1-40}$.

Example 2

Effect of Zn$^{2+}$ and other metals on Aβ polymerization using G50 gel filtration chromatography Results shown are indicative of n≧3 experiments where 55 µg of Aβ is applied to the column and eluted in 15 ml, monitored by 254 nm absorbance. (FIG. 2a) depicts chromatogram of Aβ in the presence of EDTA, 50 µM, Zn$^{2+}$, 0.4 µM; Zn$^{2+}$, 25 µM; and Cu$^{2+}$, 25 µM. The elution points of molecular mass standards and relative assignments of Aβ peak elutions are indicated. Mass standards were blue dextran (2×10$^6$ kDa, V$_0$=void volume), BSA (66 kDa), carbonic anhydrase (29 kDa), cytochrome c (12.4 kDa), and aprotinin (6.5 kDa). The mass of Aβ is 4.3 kDa. (FIG. 2b) depicts relative amounts (estimated from areas under the curve) of soluble Aβ eluted as monomer, dimer, or polymer in the presence of various metal ions (25 µM), varying concentrations of Zn$^{2+}$ or Cu$^{2+}$ (the likelihood of Tris chelation is indicated by upper limit estimates), and EDTA. Data for experiments performed in the presence of copper were taken from 214 nm readings and corrected for comparison. (FIG. 2c) depicts effects of pre-blocking the chromatography column with BSA upon the recovery of Aβ species in the presence of zinc (25 µM), copper (25 µM), or chelator.

Example 3

Aβ binding to kaolin (aluminum silicate): effects of zinc (25 µM), copper (25 µM), and EDTA (50 µM)

(FIG. 3a) depicts concentration (by 214 nm absorbance) of Aβ remaining in supernatant after incubation with 10 mg of G50 Sephadex. (FIG. 3b) depicts concentration (by 214 nm absorbance) of Aβ remaining in supernatant after incubation with 10 mg of kaolin, expressed as percent of the starting absorbance.

Example 4

Effect of Zn$^{2+}$ upon Aβ resistance to tryptic digestion (FIG. 4a) depicts a blot of tryptic digests of Aβ (13.9 µg) after incubation with increasing concentrations of zinc (lane labels, in micromolar), stained by Coomassie Blue. Digestion products of 3.6 kDa (Aβ$_{6-40}$), and 2.1 kDa (Aβ$_{17-40}$), as well as undigested Aβ$_{1-40}$ (4.3 kDa), are indicated on the left. The migration of the low molecular size markers (STD) are indicated (in kilodaltons) on the right. (FIG. 4b) depicts $^{65}$Zn$^{2+}$ binding to Aβ tryptic digestion products. The blot in 4a was incubated with $^{65}$Zn$^{2+}$, the visible bands excised, and the bound counts for each band determined. These data are typical of n=3 replicated experiments.

Example 5
Scatchard analysis of $^{65}$Zn binding to rat A$\beta_{1-40}$

Dissolved peptides (1.2 nmol) were dot-blotted onto 0.20$\mu$ PVDF membrane (Pierce) and competition analysis performed as described in Example 1 to measure the $K_A$ of zinc binding to human A$\beta_{1-40}$ (FIG. 1).

In the present invention, rat A$\beta_{1-40}$ and human A$\beta_{1-40}$ were synthesized by solid-phase Fmoc chemistry. Purification by reverse-phase HPLC and amino acid sequencing confirmed the synthesis. The tabulated results are presented in FIG. 5. The regression line indicates a $K_A$ of 3.8 $\mu$M. Stoichiometry of binding is 1:1. Although the data points for the Scatchard curve are slightly suggestive of a biphasic curve, a biphasic iteration yields association constants of 2 and 9 $\mu$M, which does not justify an interpretation of physiologically separate binding sites.

Example 6
Effect of zinc upon human, $^{125}$I-human and rat A$\beta_{1-40}$ aggregation into >0.2$\mu$ particles Stock human and rat A$\beta_{1-40}$ peptide solutions (16 $\mu$M) in water were prefiltered (Spin-X, Costar, 0.2$\mu$ cellulose acetate, 700 g), brought to 100 mM NaCl, 20 mM Tris-HCl, pH 7.4 (buffer 1)±EDTA (50 $\mu$M) or metal chloride salts, incubated (30 minutes, 37° C.) and then filtered again (700 g, 4 minutes). The fraction of the A$\beta_{1-40}$ in the filtrate was calculated by the ratio of the filtrate $OD_{214}$ (the response of the $OD_{214}$, titrated against human and rat A$\beta_{1-40}$ concentrations (up to 20 $\mu$M in the buffers used in these experiments), was determined to be linear relative to the $OD_{214}$ of the unfiltered sample. The results are tabulated in FIG. 6. All data points are in triplicate, unless indicated. (FIG. 6a) Proportions of A$\beta_{1-40}$, incubated±Zn$^{2+}$ (25 $\mu$M) or EDTA (50 $\mu$M) and then filtered through 0.2$\mu$, titrated against peptide concentration. (FIG. 6b) Proportion of A$\beta_{1-40}$ (1.6 $\mu$M) filtered through 0.2$\mu$, titrated against Zn$^{2+}$ concentration. $^{125}$I-human A$\beta_{1-40}$ ($^{125}$I-human A$\beta_{1-40}$ was prepared according to the method in J. E. Maggio, *PNAS USA* 89:5462–5466 (1992) (15,000 CPM, the kind gift of Dr. John Maggio, Harvard Medical School) was added to unlabeled A$\beta_{1-40}$ (1.6 $\mu$M) as a tracer, incubated and filtered as described above. The CPM in the filtrate and retained on the excised filter were measured by a $\gamma$-counter. (FIG. 6c) Proportion of A$\beta_{1-40}$ (1.6 $\mu$M) filtered through 0.2$\mu$ following incubation with various metal ions (3 $\mu$M). The atomic number of the metal species is indicated. (FIG. 6d) Effects of Zn$^{2+}$ (25 $\mu$M) or EDTA (50 $\mu$M) upon kinetics of human A$\beta_{1-40}$ aggregation measured by 0.2$\mu$ filtration. Data points are in duplicate.

Example 7
Size estimation of zinc-induced A$\beta$ aggregates (FIGS. 7a and 7b) Proportion of A$\beta_{1-40}$ (1.6 $\mu$M in buffer 1 (100 mM NaCl, 20 mM Tris-HCl, pH 7.4)), was incubated±Zn$^{2+}$ (25 $\mu$M) or EDTA (50 $\mu$M) and was then filtered through filters of indicated pore sizes (Durapore filters (Ultrafree-MC, Millipore) were used for this study, hence there is a slight discrepancy between the values obtained with the 0.22$\mu$ filters in this study compared to values obtained in FIG. 2 using 0.2$\mu$ Costar filters). (FIG. 7e) $^{65}$ZnCl$_2$ (130,000 CPM, 74 nM) was used as a tracer of the assembly of the zinc-induced aggregates of human A$\beta_{1-40}$ produced in FIG. 3A. By determining the amounts of A$\beta_{1-40}$ and $^{65}$Zn in the filtrate, the quantities retarded by the filters could be determined, and the stoichiometry of the zinc: A$\beta$ assemblies estimated. (FIG. 7d) Following this procedure, the filters, retaining Zn: A$\beta$ assemblies, were washed with buffer 1 (100 mM NaCl, 20 mM Tris-HCl, pH 7.4)+EDTA (50 $\mu$M×300 $\mu$l, 700 g, 4 minutes). The amounts of zinc-precipitated A$\beta_{1-40}$ resolubilized in the filtrate fraction were determined by $OD_{214}$, and expressed as a percentage of the amount originally retained by the respective filters. $^{65}$Zn released into the filtrate was measured by $\gamma$-counting.

Example 8
Zinc-induced tinctorial amyloid formation (FIG. 8a) depicts Zinc-induced human A$\beta_{1-40}$ precipitate stained with Congo Red. The particle diameter is 40$\mu$. A$\beta_{1-40}$ (200 $\mu$l×25 $\mu$M in buffer 1 (100 mM NaCl, 20 mM Tris-HCl, pH 7.4)) was incubated (30 minutes, 37° C.) in the presence of 25 $\mu$M Zn$^{2+}$. The mixture was then centrifuged (16,000 g×15 minutes), the pellet washed in buffer 1 (100 mM NaCl, 20 mM Tris-HCl, pH 7.4)±EDTA (50 $\mu$M), pelleted again and resuspended in Congo Red (1% in 50% ethanol, 5 minutes). Unbound dye was removed, the pellet washed with buffer 1 (100 mM NaCl, 20 mM Tris-HCl, pH 7.4) and mounted for microscopy. (FIG. 8b) The same aggregate visualized under polarized light, manifesting green birefringence. The experiment was repeated with EDTA (50 $\mu$M) substituted for Zn$^{2+}$ and yielded no visible material.

Example 9
Effect of zinc and copper upon human, $^{125}$I-human and rat A$\beta_{1-40}$ aggregation into >0.2$\mu$ particles Stock human and rat A$\beta_{1-40}$ peptide solutions (16 $\mu$M) in water were pre-filtered (Spin-X, Costar, 0.2$\mu$ cellulose acetate, 700 g), brought to 100 mM NaCl, 20 mM Tris-HCl, pH 7.4 (buffer 1)±EDTA (50 $\mu$M) or metal chloride salts, incubated (30 minutes, 37° C.) and then filtered again (700 g, 4 minutes). The fraction of the A$\beta_{1-40}$ in the filtrate was calculated by the ratio of the filtrate $OD_{214}$ (the response of the $OD_{214}$, titrated against human and rat $\beta_{1-40}$ concentrations (up to 20 $\mu$M in the buffers used in these experiments), was determined to be linear) relative to the $OD_{214}$ of the unfiltered sample. All data points are in triplicate, unless indicated. (FIG. 9) A graph showing the proportions of A$\beta_{1-40}$, incubated±Zn$^{2+}$ (25 $\mu$M) or Cu$^{2+}$ or EDTA (50 $\mu$M) and then filtered through 0.2$\mu$, titrated against peptide concentration.

Example 10
Effect of zinc upon A$\beta$ produced in cell culture

A cell culture, preferably mammalian cell culture, expressing, preferably overexpressing, human APP is established according to well-known methods in the art, e.g. N. Suzuki et al., *Science* 264:1336–1340 (1994); X-D Cai et al., *Science* 259:514–516 (1993); F. S. Esch et al., *Science* 248:1122–1124 (1990). Next, zinc is added to the culture medium to final concentration from about 200 nM to about 5 $\mu$M. Then the cell cultures, containing zinc, are incubated from about 15 minutes to as long as they can survive in the culture. Preferably, the cells are incubated for 3 to 4 days. While fresh media may be added to the cultures, no spent medium should be taken out since it contains amyloid or zinc-induced A$\beta$ aggregates.

The media which can be used are isotonic or physiological media, at physiological pH (about 7.4). Preferably Tyrode's buffer is used with calcium, magnesium, and potassium, as well as glucose. Any medium used must be devoid of cysteine, glutamate, aspartate, and histidine since these amino acids chelate zinc. Basically, any isotonic buffer or physiological medium which minimizes constituents which chelate zinc may be used. For example, Krebs Mammalian Ringer Solutions, in *Data for Biochemical Research*, 3d Edition by Dawson et al., Oxford Science Publications, pp.446 (N.Y. 1986), and page 447 for Balanced Salt Solutions, provide recipes for making various useful media. The constituents that should be left out are serum and the four amino acids mentioned above.

The cell culture should be incubated at about 37 degrees centigrade with air or $O_2/CO_2$ (the maximum concentration of $CO_2$ is 5%).

Next, the cells and the medium are harvested together. A detergent such as Triton (at concentrations of about 1–2% v:v) is added and the mixture is incubated for about 3 minutes to overnight. Preferably, however, it is incubated for about 1 to 2 hours.

After incubation, the cell debris as well as amyloid and zinc-induced Aβ aggregates are pelleted by centrifugation. The pellet is suspended in pepsin (about 2%) or in any other peptidase, and it is incubated from about 1 hour to overnight to allow digestion of the cell debris.

Again, it is pelleted, washed with PBS or any other appropriate salt solution, stained with Congo Red, washed again, pelleted to remove any unbound Congo Red, and resuspended in aqueous solution. At this point, a sample can be visually inspected under a microscope. Further, it can be quantitated using a grid.

Example 11

Assay for predicting the effectiveness of candidate reagents in cell culture

The assay is set up in duplicate as described in Example 10. However, a candidate reagent is added to one of the two cell cultures and EDTA is added to the other cell culture. After the final step in Example 10, the amount of amyloid and zinc-induced Aβ aggregates are compared under the microscope. The probability and level of effectiveness of the candidate reagent is assessed based on the degree decrease in formation of amyloid and zinc-induced Aβ aggregates in the cell culture.

Example 12

Rapid assay for detection of Aβ amyloid formation in biological fluid

Cerebrospinal fluid (CSF) is obtained from a healthy human subject (control) and a human patient suspected of amyloidosis. Both samples of CSF are titrated by serial dilutions, e.g., neat, 1:2, 1:4, 1:6, . . . ; dilutions may be made up to 1:10,000.

To each of the samples, an equal amount of Aβ peptide in water is added to the final concentration of above about 10 $\mu$M, preferably about 10 to about 25 $\mu$M.

Next, a solution which contains a heavy metal cation capable of binding to a peptide comprising at least amino acids 6 to 28 of Aβ, preferably $Zn^{2+}$, plus NaCl and a buffer, e.g., Tris at pH 7.4, is added to the final heavy metal cation, e.g., $Zn^{2+}$, to a final concentration of about above 300 nM, preferably 25 $\mu$M.

Then, the samples are centrifuged to form pellets. Pellets are stained with an amyloid-staining dye, e.g., Congo Red, and observed under a microscope, thereby comparing levels of Aβ amyloid in the control versus the sample from the patient with amyloidosis. If quantification of amyloid is desired, a grid can be used.

Example 13

Rapid assay for detection of Aβ amyloid formation in biologicalfluid using $^3$H-Aβ

The assay is set up as explained in Example 12, except that the Aβ peptide added is labelled beforehand by tritium. Moreover, after centrifugation, the pellets are counted in a scintillation counter.

The preferred method of detecting the amyloid, however, is by using filtration techniques as described above instead of centrifugation. After the samples are passed through a filter, the filters are added to scintillation fluid and the counts are determined.

Comparing the CPM from control samples with samples of the suspected amyloidosis patient, it can be determined whether the patient is in fact afflicted with amyloidosis. That is, an elevated CPM count in the patient samples compared to the control samples is indicative of amyloidosis.

Example 14

ELISA for detection and/or quantification of Aβ peptides

Aβ-specific antibody of the enzyme-antibody conjugate binds to Aβ peptide bound to the heavy metal cation which is bound to the microtiter well surface. The conjugated enzyme cleaves a substrate to generate a colored reaction product that can be detected spectrophotometrically. The absorbance of the colored solution in individual microtiter wells is proportional to the amount of Aβ peptide.

This assay is optimized for detection and quantitation of Aβ peptide in neat body fluids or in a partially purified or purified Aβ peptide preparation.

Pretreatment of Samples Before ELISA

The body fluid or sample of partially purified Aβ may be treated prior to transfer to the 96-well plate to increase the efficiency of Aβ absorption to the solid-phase support. Treatments can include, but are not restricted to: pre-incubation with methylating agents such as N-methyl malemide (1–10 mM for 1–2 hr) that disrupt protein metal binding sites involving a cysteine residue (the Aβ peptide does not contain a cysteine residue); the addition of soluble metal salts such as soluble $MgCl_2$ (0.5–5 mM) that block non-specific metal binding sites on proteins; the addition of compounds such as $CUCl_2$ (0.2–2 mM) which can change the polymerization state of Aβ; and the addition of buffers to acidify the solution.

Materials

Aβ peptide (purified or partially purified) or neat body fluid and controls (synthetic peptide standard)

Coating buffer (Tris 20 mM, pH 7.4, 150 mM NaCl)

Diluting buffer (Tris 20 mM, pH 7.4, 150 mM NaCl)

Blocking buffer (2% gelatine, Tris 20 mM, pH 8.0, 150 mM NaCl)

Wash buffer (Tris 20 mM, pH 8.0, 150 mM NaCl)

Normal saline (150 mM NaCl)

10 mM diethanolamine, pH 9.5, containing 0.5 mM $MgCl_2$

Urease-, HRPO-, or alkaline phosphatase-Aβ peptide conjugate (prepared as described in UNIT 11.1 of *Current Protocols in Molecular Biology*, Vol. 2, Ausubel et al., editors, (Greene Publishing Associates and Wiley-Interscience, publishers), New York.

Urease substrate solution (Allelix #1001 100), peroxidase substrate solution (Kirkegaard and Perry #50-62-00), or alkaline phosphatase substrate solution Zinc (Xenopore ZCP 00100) or Copper (Xenopore CCP 00100) 96-well microtiter plates (or other heavy metal cation bound plates as described in Materials and Methods)

Multichannel pipet

Adhesive covers or tape for covering microtiter plates

Microtiter plate spectrophotometer with 590-nm and/or 405-run filters

1. Dissolve purified or partially purified Aβ peptide and controls in coating buffer at about 0.2–2.0 Ig/ml.

Depending on the affinity of the antibody for the Aβ peptide, it may be necessary to increase or decrease the amount of Aβ peptide or neat body fluid in coating buffer.

For specificity testing, include closely related control antigens which the antibody should not recognize.

2. Fill columns 2 through 12 of a 96-well microtiter plate with 0.1 ml coating buffer.

A 96-well plate is divided into 12 columns (labeled 1–12) and 8 rows (labeled A–H).

3. Starting in column 1 of a 96-well microtiter plate, serially dilute Aβ peptide in coating buffer. Place 0.2 ml of Aβ peptide solution in each well in column 1. Remove 0.1 ml from each well with a multichannel pipet and transfer to each well in column 2, which contains 0.1 ml of coating buffer. Pipet material in column 2 five times up and down. Remove 0.1 ml from each well in column 2 and transfer to column 3. Repeat this procedure through column 11. Remove 0.1 ml from column 11 and discard. Leave column 12 blank. Prepare two identical plates for duplicate assays. For controls prepare plates as per steps 2 and 3, using control material in place of Aβ solution. An example of a control material is a coating buffer without Aβ peptide.

This will give a range of dilutions in each of 8 rows (A to H) from 1:1 through 1:1,024 [i.e., column number (dilution);

1 (1:1), 2 (1:2), 3 (1:4), 4 (1:8), 5 (1:16), 6 (1:32), 7 (1:64), 8 (1:128), 9 (1:256), 10 (1:512), and 11 (1:1,024)].

4. Cover the plates with adhesive covers or tape and incubate for 2 hours at 37° C.

5. Remove Aβ peptide solution by shaking into a sink and fill all wells with 0.3 ml blocking buffer. Incubate for 2 h at 37° C.

HRPO is inactivated by sodium azide. Do not use buffers containing sodium azide with HRPO-antibody conjugates.

Filter sterilize buffers used routinely (i.e., diluting buffer) and store at 4° C.

6. Remove blocking buffer by shaking into a sink and add 0.3 ml of washing buffer. Empty wells and refill with washing buffer. Repeat one more time.

7. Remove washing buffer by shaking into a sink and then fill rows B to H with 0.1 ml diluting buffer.

8. Add 0.2 ml of enzyme-antibody conjugate diluted in diluting buffer to row A of each plate. Recommended starting dilution of conjugate is 1:100. Serially dilute conjugate from row A to row H by transferring 0.1 ml to the well in the next row, as described in step 3. Final volume of conjugate in each well should be 0.1 ml.

This will give a range of dilution from 1:100 through 1:12,800 [row (dilution): A (1:100, B (1:200), C (1:400), D (1:800), E (1:1,600), F (1:3,200), G (1.6,400), and H (1:12,800)].

9. Cover the plates with adhesive covers or tape and incubate for a set length of time at a controlled temperature.

Time and temperature of incubation are determined empirically.

Generally, 30 to 90 min at 37° C. is sufficient. Longer times of incubation may increase sensitivity, but nonspecific binding may also increase. An example is the monoclonal mouse antibody 6E10. For example, the mouse nAb 6E10 has an optimal incubation of 2 h at 37° C. or overnight at room temperature (18–20° C).

10. Shake out the plates into a sink. Wash plates with wash buffer twice (0.3 ml each time) for urease- or alkaline phosphatase-antibody conjugates and four times for HRPO-antibody conjugates by filling well and shaking out the wash buffer into a sink. If an urease-antibody conjugate was used, rinse plates an additional three times with normal saline. If an alkaline phosphatase-antibody conjugate was used, rinse plates twice with 10 mM diethanolamine, pH 9.5, containing 0.5 mM $MgCl_2$. Pat plates dry by inverting on a paper towel.

11. Add 0.2 ml of either urease, peroxidase, or alkaline phosphatase substrate solution, depending on the enzyme-antibody conjugate used. For example, a high sensitivity substrate for HRPO is a TMB solution (Pierce catalog no. 34024) and that is measured at 450 nm. Appropriate absorbances include 590 nm (urease), 405 nm (HRPO or alkaline phosphatase), and 450 (HRPO when TMB is used as the substrate) using a microtiter plate spectrophotometer.

For alkaline phosphatase-based assays, add 100 μl of 0.1 M EDTA to each well at the end of the incubation in order to stop the reaction. For HPRO assays using TMB substrate solutions, the reaction is terminated after incubation by the addition of 25 μl of sulfuric acid (1-3 M).

12. Plot absorbance versus (Aβ) antigen concentration [Ag] on semilog paper for analysis of each dilution of enzyme-antibody conjugate. For working dilution of conjugate, choose a concentration that provides maximum sensitivity over a linear range of [Ag] and minimum binding (below 0.05 absorbance units) to control antigens (synthetic peptide standards).

13. Serially dilute individual body fluid and controls or partially purified or purified Aβ peptide preparations, as described in step 3. Use two columns per sample.

14. Repeat steps 4–6.

15. Shake out diluting buffer into a sink and add 0.1 ml per well of enzyme-antibody conjugate diluted in diluting buffer at the concentration determined in step 12.

16. Cover the plates with adhesive covers and incubate under the same conditions as used in step 9.

17. Repeat steps 10 and 11.

18. Compare the absorbance of the unknown to the standard curve for the enzyme-antibody conjugate concentration that was plotted in step 12 in order to determine the quantity of antigen expressed per volume of a body fluid or a sample of partially purified Aβ peptide.

Example 15

A method for bulk purification of Aβ peptide from biological fluids

The bulk purification of Aβ from biological fluids is best achieved with copper charged chelating-Sepharose (Pharmacia catalog no. 17-0575-01). The cysteine groups in the sample proteins are first methylated with a maleimide compound (e.g., N-methyl maleimide (Sigma catalog no. 930-88-1), about 1–10 mM, about 1 hour; also see Yomomote and KeKine, *Anal. Biochem.* 90:300–308 (1978)).

The methylated sample is then acidified by titrating pH to about 5.0 using about 1M sodium acetate, pH about 3.5, and the total NaCl concentration increased by about 500 mM with about 5M NaCl. The pH of the sample is monitored with a glass pH detector or pH indicator paper while sodium acetate is added dropwise with gentle stirring until the required pH is obtained.

The sample is then applied to a copper-charged chelating-Sepharose column (e.g., about 250 μl bed volume for about 15 ml of CSF) as described above, in the section entitled Experimental Procedures. Equilibration buffer is about 500 mM NaCl about 50 mM MES pH about 5.0 and is used to wash the column. The Sepharose can be developed with about 500 mM NaCl, 50 mM EDTA, pH 8.0 alone and the eluate sampled for western blot analysis. The treatment of 15 ml of CSF by this method enriched both soluble APP as well as 4.3 and 3.6 kD a species of Aβ (identified by an antibody that identifies an epitope in the first 16 residues of Aβ; commercially available).

In order to bind copper or zinc, the peptide requires an intact domain from residues 6–28. 4G8 only recognized the two Aβ species and not APP, confirming that the APP captured by the Sepharose was post-secretase cleaved soluble APP. The use of specific anti-Aβ antibodies as described above on western blot analysis of these products can confirm the specificity of the ELISA immunoreactivity.

Example 16

A method for purification of Aβ peptide when the volume of the biological material is less than about 4 ml The cysteine groups in the sample proteins are first methylated with a maleimide compound (e.g., N-methyl maleimide (Sigma catalog no. 930-88-1) about 1–10 mM, about 1 hour; also see Yomomote and KeKine, Anal. Biochem. 90:300–308 (1978)).

The methylated sample is then acidified by titrating pH to about 5.0 using about 1M sodium acetate, pH about 3.5, and the total NaCl concentration increased by about 500 mM with about 5M NaCl. The pH of the sample is monitored with a glass pH detector or pH indicator paper while sodium acetate is added dropwise with gentle stirring until the required pH is obtained.

Free copper-charged chelating-Sepharose slurry (about 60 μl of about 50% v/v) is added to the sample.

Following centrifugation (preferably, low speed centrifugation (about 1,500 g, for about 3 minutes, equilibration buffer is used to wash the Sepharose pellet. Equilibration buffer is about 500 mM NaCl about 50 mM MES, pH about 5.0.

The Sepharose can be developed (protein is eluted by the addition of the eluting buffer) with about 500 mM NaCl, 50 mM EDTA, pH 8.0 alone and the eluate sampled for western blot analysis.

Having now fully described this invention, it will be understood by those of skill in the art that it can be performed within any wide range of equivalent modes of operation as well as other parameters without affecting the scope of the invention or any embodiment thereof.

All patents and publications cited in the present specification are incorporated by reference herein in their entirety.

What is claimed is:

1. An assay for detecting and/or quantifying Aβ peptide which may be present in a candidate solution, comprising:

(a) contacting the candidate solution with a solid support with a heavy metal cation immobilized thereon to capture Aβ peptide on the surface of the solid support, thereby forming a first complex which comprises solid support/heavy metal cation/Aβ peptide;

(b) blocking all exposed metal binding sites remaining after Aβ capture with a blocker;

(c) contacting the first complex, which has been passed through step (b), with an antibody specific for Aβ peptide to form a second complex which comprises solid support/heavy metal cation/Aβ peptide/antibody specific for Aβ peptide;

(d) labelling the second complex to form a detectable third complex which comprises solid support/heavy metal cation/Aβ peptide/antibody specific for Aβ peptide/label; and (e) detecting the third complex, and quantifying Aβ peptide which may be present in the candidate solution.

2. An assay for detecting and/or quantifying Aβ peptide which may be present in a candidate solution, comprising:

(a) contacting the candidate solution with a solid support with a heavy metal cation immobilized thereon to capture Aβ peptide on the surface of the solid support, thereby forming a first complex which comprises solid support/heavy metal cation/Aβ peptide;

(b) blocking all exposed metal binding sites remaining after Aβ capture with a blocker;

(c) contacting the first complex, which has been passed through step (b), with an antibody specific for Aβ peptide, called Aβ antibody, to form a second complex which comprises solid support/heavy metal cation/Aβ peptide/Aβ antibody;

(d) contacting said second complex with one or more anti-antibodies specific to the Aβ antibody to form a third complex which comprises solid support/heavy metal cation/Aβ peptide/Aβ antibody/one or more anti-antibodies;

(e) labelling said third complex to form a detectable fourth complex which comprises solid support/heavy metal cation/Aβ peptide/Aβ antibody/one or more anti-antibodies/label; and (f) detecting the fourth complex, thereby quantifying Aβ peptide which may be present in the candidate solution.

3. The assay as claimed in claim 1, wherein said heavy metal cation is selected from the group consisting of zinc (II) and copper (II) complexed to nitriloacetic acid.

4. The assay as claimed in claim 2, wherein said heavy metal cation is selected from the group consisting of zinc (II) and copper (II) complexed to nitriloacetic acid.

5. The assay as claimed in claim 3, wherein said antibody at step (c) is a monoclonal antibody specific to $A\beta_{1-42}$ and does not cross react with $A\beta_{1-40}$.

6. The assay as claimed in claim 3, wherein said antibody at step (c) is a monoclonal antibody specific to $A\beta_{1-40}$ and does not cross react with $A\beta_{1-42}$.

7. The assay as claimed in claim 4, wherein said antibody at step (c) is a monoclonal antibody specific to $A\beta_{1-42}$ and does not cross react with $A\beta_{1-40}$.

8. The assay as claimed in claim 4, wherein said antibody at step (c) is a monoclonal antibody specific to $A\beta_{1-40}$ and does not cross react with $A\beta_{1-42}$.

9. The assay as claimed in claim 5, wherein said antibody is labelled with a radioisotope.

10. The assay as claimed in claim 6, wherein said antibody is labelled with a radioisotope.

11. The assay as claimed in claim 7, wherein said antibody is labelled with a radioisotope.

12. The assay as claimed in claim 8, wherein said antibody is labelled with a radioisotope.

13. The assay as claimed in claim 5, wherein said enzyme is horseradish peroxidase.

14. The assay as claimed in claim 6, wherein said enzyme is horseradish peroxidase.

15. The assay as claimed in claim 7, wherein said enzyme is horseradish peroxidase.

16. The assay as claimed in claim 8, wherein said enzyme is horseradish peroxidase.

17. A kit for carrying out the assay of claim 1 or 2, which comprises a carrier means compartmentalized in close confinement therein to receive one or more container means which comprises a first container means containing a solid support having a heavy metal cation immobilized thereon and a second container means containing an antibody specific for Aβ peptide.

18. The kit as claimed in claim 17, wherein said heavy metal cation is selected from the group consisting of zinc (II) and copper (II) complexed to nitriloacetic acid.

19. The kit as claimed in claim 17, wherein said antibody is labelled with a radioisotope.

20. The kit as claimed in claim 17, wherein said enzyme is horseradish peroxidase.

21. The kit as claimed in claim 17, wherein said carrier means further comprises a third container means containing an anti-antibody which is specific for the Aβ antibody.

22. The kit as claimed in claim 21, wherein said anti-antibody is labelled with a radioisotope.

23. A kit for carrying out the assay of claim 1 or 2, which comprises a carrier means compartmentalized in close confinement therein to receive one or more container means which comprises a first container means containing a solid support having a heavy metal cation immobilized thereon and a second container means containing a labelled antibody specific for Aβ peptide.

24. The kit as claimed in claim 23, wherein said heavy metal cation is selected from the group consisting of zinc (II) and copper (II) complexed to nitriloacetic acid.

25. The kit as claimed in claim 23, wherein the labelled antibody is labelled by a radioisotope.

26. The kit as claimed in claim 23, wherein said enzyme is horseradish peroxidase.

27. The kit for carrying out the assay of claim 1 or 2, which comprises a carrier means compartmentalized in close confinement therein to receive one or more container means which comprises a first container means containing a solid support having a heavy metal cation immobilized thereon and a second container means containing an antibody specific for Aβ peptide bound to a labelled anti-antibody.

28. The kit as claimed in claim 27, wherein said heavy metal cation is selected from the group consisting of zinc (II) and copper (II) completed to nitriloacetic acid.

29. The kit as claimed in claim 27, wherein the labelled antibody is labelled by a radioisotope.

30. The kit as claimed in claim 27, wherein said enzyme is horseradish peroxidase.

\* \* \* \* \*